(12) United States Patent
Ronayne et al.

(10) Patent No.: US 11,110,242 B2
(45) Date of Patent: Sep. 7, 2021

(54) PATIENT INTERFACE

(71) Applicant: Fisher & Paykel Healthcare Limited, Auckland (NZ)

(72) Inventors: Michael Paul Ronayne, Auckland (NZ); Riki Zane Shearer, Auckland (NZ); Daniel Charles Wilson, Auckland (NZ); Robert Andrew David Milne, Auckland (NZ); Caroline Geraldine Hopkins, Auckland (NZ); Craig Karl White, Auckland (NZ); Puqing Zhang, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 705 days.

(21) Appl. No.: 15/028,924

(22) PCT Filed: Oct. 16, 2014

(86) PCT No.: PCT/NZ2014/000217
§ 371 (c)(1),
(2) Date: Apr. 12, 2016

(87) PCT Pub. No.: WO2015/057083
PCT Pub. Date: Apr. 23, 2015

(65) Prior Publication Data
US 2016/0235937 A1 Aug. 18, 2016

Related U.S. Application Data

(60) Provisional application No. 61/891,697, filed on Oct. 16, 2013, provisional application No. 61/919,579, filed on Dec. 20, 2013.

(51) Int. Cl.
*A61M 16/06* (2006.01)
*A61M 16/08* (2006.01)

(52) U.S. Cl.
CPC ........ *A61M 16/0666* (2013.01); *A61M 16/06* (2013.01); *A61M 16/0605* (2014.02);
(Continued)

(58) Field of Classification Search
CPC .......... A61M 16/0666; A61M 16/0605; A61M 16/0672; A61M 16/0825; A61M 16/0683;
(Continued)

(56) References Cited

U.S. PATENT DOCUMENTS 2,693,800 A * 11/1954 Caldwell ........... A61M 16/0666
128/207.18
3,513,844 A * 5/1970 Smith ............... A61M 16/0666
128/207.18
(Continued)

FOREIGN PATENT DOCUMENTS

AU 2007278766 1/2018
CA 2814601 4/2013
(Continued)

OTHER PUBLICATIONS

International Search Report and Written Opinion; PCT/NZ2014/000217; dated Jan. 12, 2015; 21 pages.
(Continued)

*Primary Examiner* — Tu A Vo
(74) *Attorney, Agent, or Firm* — Knobbe, Martens, Olsen & Bear

(57) ABSTRACT

This invention relates to a patient interface, such as a nasal cannula, including a body to be positioned upon a user (preferably such as a user's face), the body including at least one (and preferably a pair of) nasal prong(s), the or each nasal prong including a lumen capable of being fluidly connected thereto for fluid communication with a supply of breathable gas, the or each nasal prong to be in a configuration either inserted into, or to direct a flow of gas toward,
(Continued)

a nare or the nares of the user's nose, wherein the body includes at least one element responsive to force(s) or movement(s), or both, experienced by at least a first region of the patient interface.

21 Claims, 28 Drawing Sheets

(52) U.S. Cl.
CPC .... *A61M 16/0672* (2014.02); *A61M 16/0825* (2014.02); *A61M 16/0683* (2013.01); *A61M 16/0688* (2014.02); *A61M 2205/0216* (2013.01)

(58) Field of Classification Search
CPC ...... A61M 2205/0216; A61M 16/0688; A61M 16/06; A61M 16/0677; A61M 2210/0618; A61M 2210/0606; A61M 2202/0208; A61M 16/0816
See application file for complete search history.

(56) References Cited

U.S. PATENT DOCUMENTS

| | | | |
|---|---|---|---|
| 3,726,275 A * | 4/1973 | Jackson | A61M 16/0672 128/207.18 |
| 3,754,552 A | 8/1973 | King | |
| 4,106,505 A | 8/1978 | Salter et al. | |
| 4,278,082 A * | 7/1981 | Blackmer | A61M 16/0666 128/207.18 |
| 4,753,233 A * | 6/1988 | Grimes | A61M 16/0666 128/203.22 |
| 7,406,966 B2 | 8/2008 | Wondka | |
| 7,614,401 B2 * | 11/2009 | Thompson | A61M 16/0666 128/204.12 |
| 8,136,527 B2 * | 3/2012 | Wondka | A61M 16/06 128/200.24 |
| 2001/0029954 A1 | 10/2001 | Palmer | |
| 2002/0046755 A1 | 4/2002 | De Voss | |
| 2003/0079749 A1 | 5/2003 | Strickland et al. | |
| 2003/0126724 A1 | 7/2003 | Kono et al. | |
| 2003/0135192 A1 | 7/2003 | Guralski et al. | |
| 2004/0226566 A1 | 11/2004 | Gunaratnam et al. | |
| 2004/0261797 A1 | 12/2004 | White et al. | |
| 2005/0028822 A1 | 2/2005 | Sleeper et al. | |
| 2005/0066976 A1 * | 3/2005 | Wondka | A61M 16/06 128/207.18 |
| 2006/0107958 A1 | 5/2006 | Sleeper | |
| 2006/0180151 A1 * | 8/2006 | Rinaldi | A61M 16/0666 128/206.11 |
| 2007/0283957 A1 | 12/2007 | Schobel | |
| 2008/0060649 A1 | 3/2008 | Veliss et al. | |
| 2008/0173305 A1 * | 7/2008 | Frater | A61M 16/08 128/204.26 |
| 2008/0190436 A1 * | 8/2008 | Jaffe | A61M 16/024 128/207.18 |
| 2009/0056711 A1 | 3/2009 | Richards et al. | |
| 2009/0095303 A1 | 4/2009 | Sher et al. | |
| 2009/0151729 A1 | 6/2009 | Judson et al. | |
| 2009/0173349 A1 | 7/2009 | Hernandez et al. | |
| 2009/0183739 A1 | 7/2009 | Wondka | |
| 2010/0000534 A1 | 1/2010 | Kooij et al. | |
| 2010/0018534 A1 | 1/2010 | Veliss et al. | |
| 2010/0113955 A1 | 5/2010 | Colman et al. | |
| 2010/0192957 A1 | 8/2010 | Hobson et al. | |
| 2010/0224196 A1 * | 9/2010 | Jablons | A61M 16/0666 128/207.18 |
| 2011/0067704 A1 | 3/2011 | Kooij et al. | |
| 2011/0214676 A1 | 9/2011 | Allum et al. | |
| 2012/0111332 A1 | 5/2012 | Gusky et al. | |
| 2012/0132209 A1 | 5/2012 | Rummery et al. | |
| 2013/0239301 A1 * | 9/2013 | Broderick | A61M 16/0666 2/410 |
| 2014/0000626 A1 | 1/2014 | O'Connor et al. | |
| 2014/0130805 A1 | 5/2014 | Tiep et al. | |
| 2014/0158127 A1 | 6/2014 | Boucher et al. | |
| 2014/0332007 A1 | 11/2014 | Znamenskiy | |
| 2017/0348500 A1 | 12/2017 | Johnson et al. | |

FOREIGN PATENT DOCUMENTS

| | | |
|---|---|---|
| CN | 1905917 A | 1/2007 |
| CN | 101653632 A | 2/2010 |
| CN | 101977656 A | 2/2011 |
| CN | 101389369 A | 3/2013 |
| EP | 2130563 | 12/2009 |
| EP | 1481702 | 9/2012 |
| EP | 2022528 | 3/2016 |
| JP | 2007/506480 | 3/2007 |
| JP | 2009/291615 | 12/2009 |
| JP | 2009-544371 | 12/2009 |
| JP | 2011/5002229 | 1/2011 |
| JP | 2011/509762 | 3/2011 |
| JP | 2011/510707 | 4/2011 |
| JP | 2012-515562 | 7/2012 |
| JP | 2012/522608 | 9/2012 |
| JP | 2013-503720 | 2/2013 |
| JP | 2013-540037 | 10/2013 |
| WO | WO 2005/010608 | 2/2005 |
| WO | WO 2005/018524 | 3/2005 |
| WO | WO 2006/130903 | 12/2006 |
| WO | WO 2008/011682 | 1/2008 |
| WO | WO 2008/060587 | 5/2008 |
| WO | WO 2008/070929 | 6/2008 |
| WO | WO 2009/109005 | 9/2009 |
| WO | WO 2011/062510 | 5/2011 |
| WO | WO 2012/053910 | 4/2012 |
| WO | WO-2012053910 A1 * | 4/2012 ............ A61M 16/00 |
| WO | WO 2013/014581 | 1/2013 |
| WO | WO 2014/142681 A1 | 9/2014 |
| WO | WO 2015/057083 | 4/2015 |

OTHER PUBLICATIONS

Examination Report dated Jun. 18, 2018 for Australian Application No. 2014335018 in 5 pages.
Japanese Office Action in 8 pages dated Aug. 13, 2018 in Japanese Application No. 2016-524416.
Chinese exam report in 11 pages dated Oct. 17, 2018 in Chinese Application No. 201480069093.1.
Extended European Search Report, PCT/NZ2015/050156; dated Feb. 20, 2018; 8 pages.
Extended European Search Report dated May 15, 2017 in EP Appl. No. 1485791.2 in 7 pages.
Chinese exam report in 10 pages dated Jun. 28, 2017 in Chinese Application No. 201480069093.1.
International Search Report, PCT/NZ2015/050156, dated Nov. 10, 2015, in 5 pages.
European Examination Report dated Jan. 25, 2019 in EP Appl. No. 1485791.2 in 3 pages.
Chinese Office Action dated Jan. 29, 2019 for Chinese Application No. 201580060077.0 in 20 pages.
Japanese Examination Report dated Mar. 6, 2019, Japanese Patent Application 2016-524416 in 9 pages.
Japanese Examination Report, Japanese Application No. 20177-515742, dated Jun. 18, 2019 in 12 pages.
China National Intellectual Property Administration, Second Office Action, Application No. 201580060077.0, dated Oct. 18, 2019, in 29 pages.
Australian Government, Examination Report No. 1 for Standard Patent Application, Application No. 2015318732, dated Aug. 9, 2019, in 4 pages.
Canadian Exam Report for Application No. 2,927,088 dated Jan. 7, 2021, 4 pages.
UK Examination Report for Patent Application No. GB2014636.1 dated Nov. 9, 2020, in 8 pages.
UK Examination Report for Patent Application No. GB2012226.3 dated Nov. 6, 2020, in 8 pages.

(56) References Cited

OTHER PUBLICATIONS

Chinese Notification of Reexamination for Chinese Application No. 201480069093.1, dated Jan. 20, 2020 in 16 pages.
UK Examination Cover Letter and Examination Report for Patent Application No. GB1606325.7 dated Apr. 21, 2020, in 4 pages.
Japanese Notice of Reasons for Refusal for JP Application No. 2017-515742, dated Apr. 14, 2020, in 8 pages.
Chinese Examination Report and English Translation for Chinese Application No. 201580060077.0, dated May 15, 2020, 11 pages.
European Examination Report for European Patent Application 15841985.3 dated Jul. 8, 2020, 6 pages.
Australian Examination Report No. 2 for Standard Patent Application, Application No. 2015318732, dated Jun. 18, 2020, in 5 pages.
Indian Examination Report for Patent Application No. 201637013355, dated Sep. 15, 2020, 8 pages.
Australian Examination Report No. 1 for Standard Patent Application for Application No. 2019203650, dated Aug. 3, 2020, in 8 pages.

\* cited by examiner

Relaxed State

Stressed State

Relaxed State

Stressed State

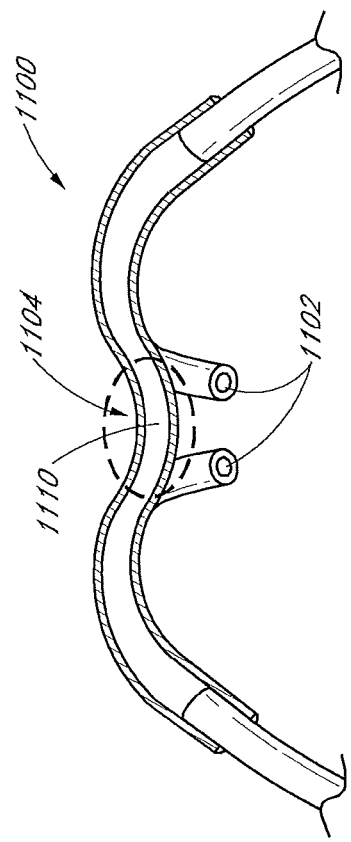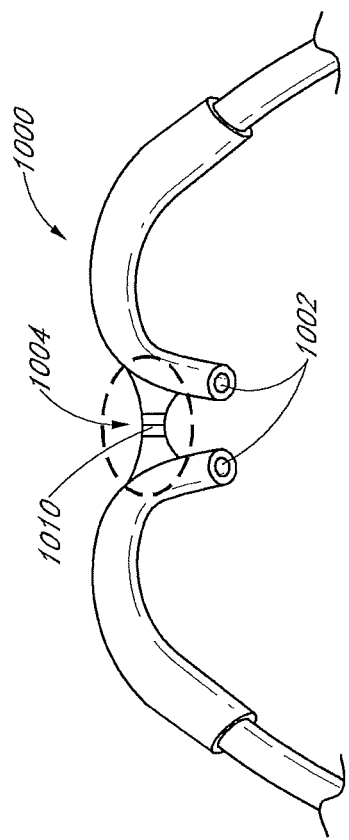
FIG. 12A
FIG. 13A
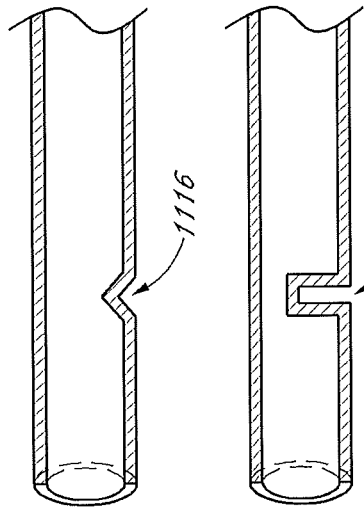
FIG. 13B  FIG. 13C  FIG. 13D
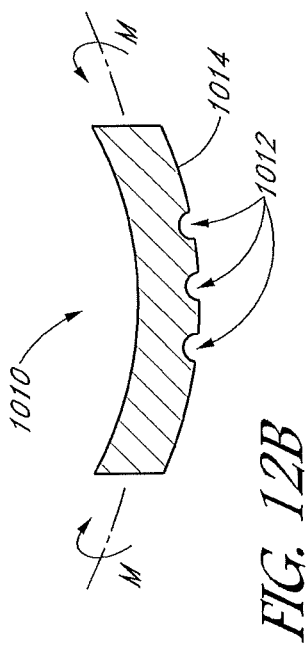
FIG. 12B

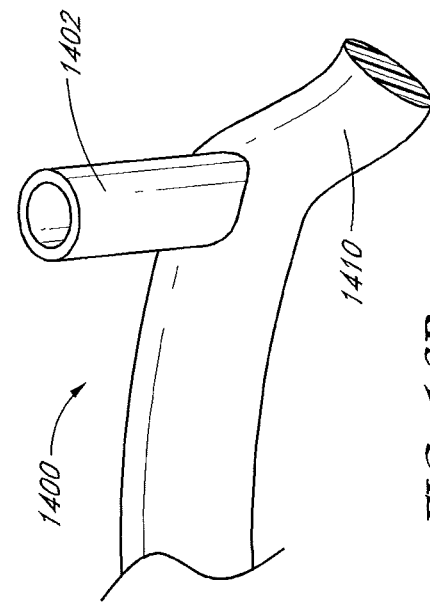
FIG. 16B
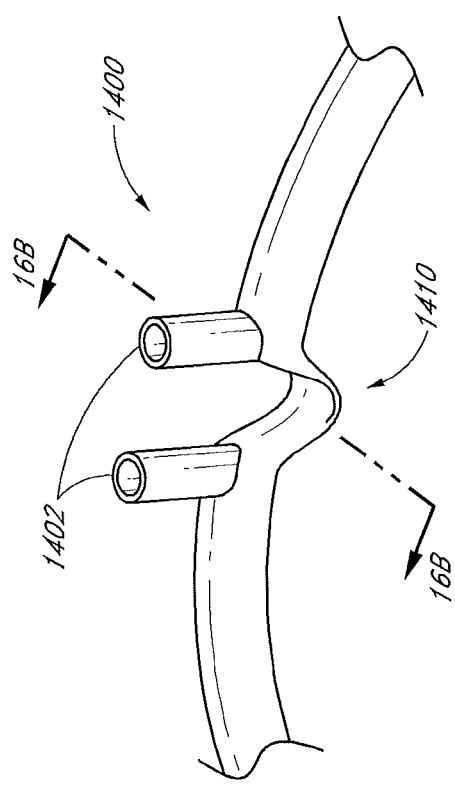
FIG. 16A
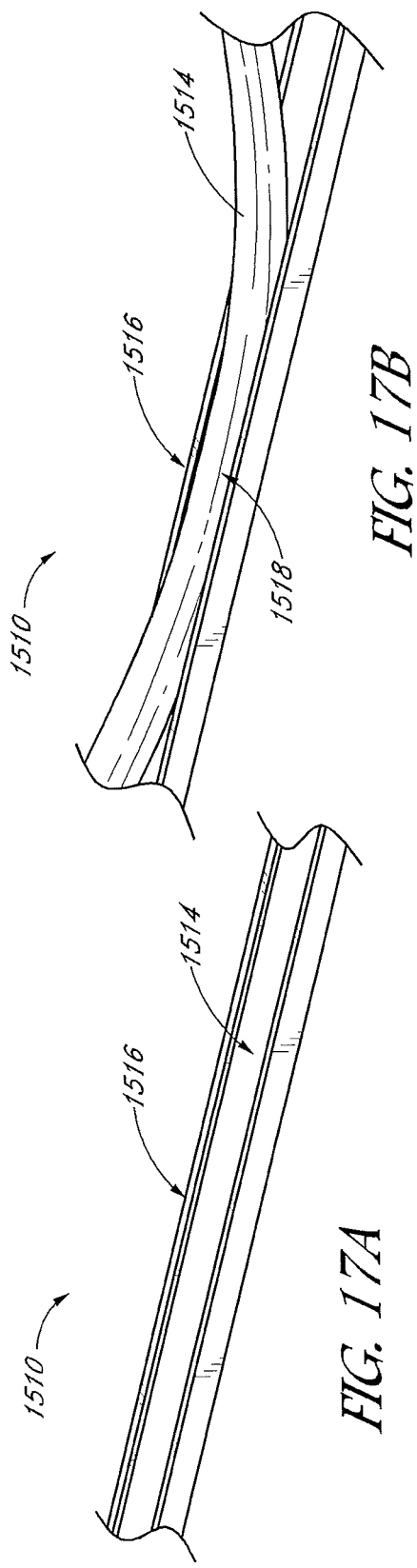
FIG. 17B
FIG. 17A

PATIENT INTERFACE

FIELD OF THE INVENTION

The present invention relates to patient interfaces, more particularly, though not solely, to patient interfaces for delivery of gases to a user, for example such as nasal cannula for delivering gases to the nares of a user's nose, where the patient interface is capable of configurations providing for enhanced stability when in-situ upon the user's face.

BACKGROUND TO THE INVENTION

There are many forms of patient interfaces for delivery of gases to a user, such as for example full face masks, oro-nasal masks, nasal masks and nasal cannula.

There are a significant variety of patient interfaces available to users, each of which may have their own stability issues.

Stability of an interface upon a user is of importance for at least the reasons of comfort and maintenance of a desired therapy delivery to the user.

Instability of an interface may lead to dislodgment of an interface or components of the interface which may affect the desired delivery or integrity of therapy for the user.

In various modes, instability of an interface upon a user may be, for example, the result of loading such as by a user speaking and changing the geometry of their face to which the interface is positioned. Facial geometry, such as that of humans, varies greatly due to a large range of factors. These factors may include, but are not limited to, gender, age, or particular medical conditions. Incorrect sizing and geometry of an interface to a particular user may also adversely affect the stability and usability of certain patient interfaces.

In terms of facial movement, when a user speaks, eats, cries or has their facial features distorted or exaggerated, such movement can affect the stability of a patient interface or components of the interface on a user, for example such as a nasal prong or a pair of such prongs of a nasal cannula which may inadvertently come out of a gas delivery position for delivering gas to the nare(s) of a user's nose. More prolonged changes to facial features can also arise from aspects such as a user's position, for example while sleeping. Long term changes in geometry can also occur from user growth and injury recovery.

In relation to the above, it will be appreciated that either due to changes in geometry of a user to which the patient interface is located, or for example by yet other forces, such as by a user pulling on a tube or the interface or other components attached to these, forces or movements can be transmitted to the interface and components thereof. The application of such forces can pose problems of stability, comfort and operational use of the patient interface for a user.

It is therefore an object of the present invention to provide a patient interface, for example such as a nasal cannula, which will go at least some way towards addressing the foregoing problems or which will at least provide the industry/public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction: are prior art, or form part of the common general knowledge in the art.

Further aspects and advantages of the present invention will become apparent from the ensuing description which is given by way of example only.

SUMMARY OF THE INVENTION

In a first aspect, the present invention may broadly consist in a patient interface, such as a nasal cannula, comprising a body to be positioned upon a user (preferably such as a user's face), the body including at least one (and preferably a pair of) nasal prong(s), the or each nasal prong including a lumen capable of being fluidly connected thereto for fluid communication with a supply of breathable gas, the or each nasal prong to be in a configuration either inserted into, or to direct a flow of gas toward, a nare or the nares of the user's nose, wherein the body includes at least one element (optionally mechanically) responsive to force(s) or movement(s), or both, experienced by at least a first region of the patient interface; optionally or alternatively wherein the body includes at least one element (optionally mechanically) responsive to force(s) or movement(s), or both, experienced by at least a first region of the patient interface from being transferred to at least one other region of the patient interface.

Preferably the element facilitates the reduction in transfer of a force or movement, or both, applied to at least a first region of the interface from being transferred to at least another region of the interface.

Preferably the element responds in a manner to localise the force or the movement, or both, experienced by the at least first region.

Preferably the element responds to minimise or prevent transfer of the force or the movement, or both, from the at least first region to at least one other region of the patient interface.

Preferably the element responds in a manner to maintain the at least one (and preferably the pair of) nasal prong(s) in the configuration of insertion in a nare or nares of the user's nose, or in the configuration of directing a flow of gas toward a nare or nares of the user's nose.

Preferably the response is such that the at least one (or preferably the pair of) nasal prong(s) maintain a stable position within or adjacent to the nares of a user's nose to which the prong(s) is directed.

Preferably the response is such that the interface maintains an operational position upon the user.

Preferably the response is such that the interface maintains a stabile position upon the user.

Preferably the force or movement, or both, experienced by at least a first region of the interface are either, or both, of:

an applied force(s) or a movement(s) between the nasal prong(s) and body of the patient interface, or an applied force(s) or a movement(s) between the body of the patient interface and the nasal prong(s).

Preferably the element is deformable or deformed in response to the force or movement, or both, being experienced by at least the first region of the interface.

Preferably the element has a predetermined or preferential mode of deformation in response to an applied force or movement, or both, being experienced by at least a first region of the interface.

Preferably the element is deformable by one or a combination of a compression or a tension or a torsion or bending or other flexion.

Preferably the element responds to the force or movement, or both, experienced by at least the first region of the interface by one or a combination of: changing shape, changing position, changing configuration or deforming.

Preferably the element comprises one or a combination of any of the following:

hinges, pivots, articulated joints or articulately connected portions of the body or portions associated with the body, swivels, ball-and-socket type joints, pin-in-barrel type joints, materials which are relatively less flexible than other portions of the interface, materials which are relatively more flexible than other portions of the interface, materials of characteristics which change upon application of a force or movement, such as by increasing their resistance to the applied force or movement (or both), or by reducing their resistance to the applied force or movement (or both), or materials which are elastically deformable in response to the applied force or movement (or both), or materials which are preferentially deformable in particular or predetermined geometries and yet which may optionally be resistant to deformation in other particular or predetermined geometries.

Preferably the element is one or more of the following:

a pivot (or swivel) or region capable of pivoting (or swivelling), or a hinge or a hinged region or region capable of being hinged relative to another component of the interface or another region of the interface, or an articulation or articulated joint or region capable of being articulated.

Preferably the element provides for a de-coupling of forces or movement (or both) which is applied to at least the first region of the interface from being transferred to at least one other region of the interface.

Preferably the element provides or is operable or works to prevent or minimise transfer of force of movement from the at least first region of the interface to at least one other region of the interface.

Preferably the element may be a structure or a mechanism of the interface or may be a region of the interface.

Preferably the element is deformable about at least one axis or at least one plane.

Preferably the element is deformable about a preferential first geometry.

Preferably the element is deformable by one or a combination of a compression or a tension or a torsion or bending or other flexion.

Preferably there are two or more elements are located about the interface.

Preferably elements are connected together in a manner so as to provide for a combined response to the force or movement (or both).

Preferably element may respond to the force or movement (or both) in a different mode, thereby providing for a combined response.

Preferably elements are operatively coupled to each other, or to other portions of the interface to provide for a or the combined response.

Preferably at least one of the elements, or each such element, is provided as one or more of:

an isolator or a region of isolation,
an absorber or a region of absorption,
a dampener or a region of dampening,
or the any other structure or mechanism providing for a reactive response to a force(s) or movement(s) imparted to at least a first region of the patient interface from being transferred to at least a second or another region of the patient interface.

Preferably the response of one or each element is at least one (or a combination) of an isolation or an absorption or a dampening or a reduction of the force(s) or movement(s) imparted to at least the first region from being transferred to at least one other region of the patient interface during use by a user.

Preferably the element is pre-formed so as to be deformed or displaced in a preferential geometry or dimension.

Preferably the element facilitates a preferential bend or flexure or twist or torsion or a preferential or predetermined pivot or stretch or compression of a material(s) or a component(s) forming the body of the interface.

Preferably such force(s) or movement(s) are resultant from a user of the interface changing their facial geometry to which the interface is retained or located or positioned, or such as by a user pulling or applying a force or movement on or to the interface or an associated headgear thereof, or a breathing circuit or other componentry of the interface applying a force or movement, such as by weighing down upon, a portion of the interface or a headgear associated thereof.

Preferably the applied forces or movement between the nasal prong(s) and body of the patient interface, or between the body of the patient interface and the nasal prong is resultant from changes in user facial geometry, such as during speech, eating, sleeping or other facial distortions between relaxed and exaggerated conditions.

Preferably the at least one element, or at least one of the elements, is located in a bridge region of a nasal cannula patient interface, to facilitate movement of the bridge region in response to a force or movement or both (in addition, may be such as substantially adjacent the septum region of a user).

Preferably the interface comprises a plurality of elements utilised on their own or in combination with other elements to provide for the response.

Preferably the at least one element is a hinged portion located or positioned as a bridge between a left body portion and a right body portion, each of the body portions together forming the body of an interface to be located upon a user's face, such a hinged portion providing for a preferential region of deformation in response to at least a first region of the body or a portion of the body, experiencing a force or movement (or both) resulting from a change in the facial geometry of the user.

Preferably the patient interface is substantially conformed or conformable to the geometry of a user's face, such that the element responds to the force or movement (or both) to substantially maintain the interface in a preferred therapy delivery configuration for a user.

In a further aspect, the present invention may broadly consist in a patient interface, such as a nasal cannula, comprising: a pair of respective left and right body portions, each body portion to be located, in-use, upon a face of a user, each of the body portions being separate from each other, at least one, and preferably both, of the body portions including a nasal prong to be inserted into, or to direct a flow of gas into, a nare or the nares of the user's nose, and a bar extending from a connection point with the left body portion to a connection point with the right body portion, the bar comprising a substantially elastically deformable region, wherein a displacement of one or both of the left and/or right body portions when in-use is transmittable to the bar via the connection point, the substantially elastically deformable region being deformable as a reactive response to the displacement.

Preferably the substantially elastically deformable region of the bar comprises a substantially flexible section.

Preferably the substantially elastically deformable region of the bar is deformable to substantially absorb the displacement.

Preferably the substantially elastically deformable region of the bar reduces transmission of a displacement by one of the body portions to the other of the body portions.

Preferably the connection point of the bar to a body portion is via an anchor.

Preferably the anchor is a barbed projection to be received by a region of the body portion located substantially distal to the respective prong.

Preferably the barbed projection and the prong are in fluid communication.

Preferably the elastically deformable region is substantially aligned with the or both prongs in at least one plane.

Preferably each connection point of the bar is in fluid communication with the prong of the respective body portion and is configured to couple a gas flow path of a breathing circuit.

Preferably a facial pad may be associated with each body portion, the facial pad being contoured to engage a region of the user's face.

In a further aspect, the present invention may broadly consist in a patient interface, such as a nasal cannula, comprising: a pair of respective left and right body portions, to be located, in-use upon a face of a user, and a bridge portion extending between each of the left and right body portions, a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, the bridge portion allowing movement of the respective body portions with the inner-more ends of the body portions being brought toward each another, yet resisting movement of the respective body portions with the inner-more ends being moved away from each other.

Preferably a displacement of the position of one or both of the left and/or right body portions, when the patient interface is in-situ upon a user's face, is transmitted to the bridge in a manner so as to minimise movement of the prong or prongs in relation to the user's nare(s).

Preferably the bridge portion extends and connects inner-more ends of the respective body portions.

Preferably the bridge portion is a material that, in a direction extending between the respective inner-more ends of the body portions, is able to undergo a compression and resists or withstands a tension applied thereto.

Preferably the direction extending between the respective inner-more ends of the body portions is a longitudinal direction extending along the respective body portions.

Preferably the bridge portion comprises a textile material.

Preferably the bridge portion is axially expandable/stretchable but resilient to resist movement of the respective body portions with the inner-more ends being moved away from each other.

Preferably a length of the bridge portion between a connection point on the left body portion and a connection point on the right body portion is larger than a distance between the nasal prongs.

Preferably the bridge portion comprises a flexible polymeric material.

In a further aspect, the present invention may broadly consist in a patient interface, such as a nasal cannula, comprising: a pair of respective left and right body portions, to be located, in-use upon a face of a user, a bridge portion extending between each of the left and right body portions, and a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, wherein one, and preferably both, of the respective body portions include a user facial contacting surface oriented relative to the respective nasal prong such that, when in situ, a torsional force applied to the left and/or right body portions substantially retains the nasal prong(s) in, or in a position to direct a flow of gas into, the nare(s) of the user's nose.

Preferably rotation of the body portion, and preferably rotation of both body portions, towards a user's face maximises a contact surface area between the facial contacting surface(s) and the face of the user and locates the nasal prong(s) into, or in the position for directing the flow of gases into, the nare(s) of the user's nose.

Preferably the bridge section is of a relatively smaller diameter than the left and right body portions.

Preferably each body portion comprises a channel fluidly connected to the respective nasal prong at one end and open for fluidly coupling a gas flow path of a breathing circuit at an opposing end.

Preferably at least one, and preferably each, of the left and right body portions includes an axially twisted facial contacting surface moveable between a relaxed position and a torsioned position in which a surface area for locating adjacent the user's face is increased.

Preferably the facial contacting surface is axially twisted along a length of the body portion from an inner end of the body portion to an outer end of the body portion.

Preferably the facial contacting surface extends helically along the length of the body portion.

Preferably the facial contacting surface, in the relaxed position, faces away from a direction of extension of the nasal prong(s) at the distal end, and in the torsioned position, faces in the direction of extension of the nasal prong(s) and is substantially planar along a substantial length of the body portion.

Preferably the nasal prong or the nasal prongs are angled relative to the respective left and right body portions to exert torsion on the body portion upon insertion of the nasal prong(s) into the nare(s) of the user's nose.

Preferably the facial contacting surface of the respective left and/or right body portion is contoured to engage the user's facial cheek.

In a further aspect, the present invention may broadly consist in a patient interface, such as a nasal cannula, comprising: a pair of respective left and right body portions, to be located, in-use upon a face of a user, and a bridge portion extending between each of the left and right body portions, a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, and a series of discrete and separate facial contacting surface(s) movable relative to each other to respond to force(s) or movement(s), or both, experienced by facial contacting surface(s) and at least partially alleviate the transfer of such force(s) and/or movement(s) to the nasal prong(s).

In a further aspect, the present invention may broadly consist in a patient interface, such as a nasal cannula, comprising: a pair of respective left and right body portions, each body portion to be located, in-use upon a face of a user, and a bridge portion extending between the left and right body portions, and a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, wherein the cannula includes at least one hinged region pivotable relative to another region of the cannula about at least a pair of substantially orthogonal axes, or along a pair of substantially orthogonal planes, or both, to respond to force(s) or movement(s), or both, experienced by the other region and at least partially alleviate the transfer of such force(s) and/or movement(s) to the nasal prong(s).

Preferably at least one hinged region is pivotable about three substantially orthogonal axes, or along three substantially orthogonal planes, or both.

Preferably the bridge comprises a bridge hinge adjacent the nasal prong or between the pair of nasal prongs.

Preferably the bridge hinge is predisposed to have an acute curvature.

Preferably the bridge hinge is predisposed to bend inward toward the user, and downward away from the nare(s) in situ.

Preferably the bridge further comprises a second hinge on one side of the bridge hinge, or a pair of opposed second hinges on either side of the bridge hinge and adjacent the nasal prong or nasal prongs.

Preferably the second hinge or each hinge of the pair of second hinges is predisposed to have an acute curvature.

Preferably the second hinge, or each hinge of the pair of second hinges is predisposed to bend upwardly towards the nare(s) of the user and outwardly away from the user in situ.

Preferably the bridge comprises a third hinge adjacent the left or the right body portion, or a pair of third hinges disposed adjacent the respective left and right body portions.

Preferably the third hinge or each of the pair of third hinges is predisposed to have an acute curvature.

Preferably the third hinge or each of the pair of third hinges is predisposed to bend downward away from the nare(s) and outward away from the user in situ.

Preferably one end of the bridge portion extends substantially orthogonally from the third hinge, or either end of the bridge portion extends substantially orthogonally from either one of the pair of third hinges and inwardly towards the facial cheek(s) of the user in situ.

Preferably each body portion comprises a facial pad contoured to engage a region of the user's face.

Preferably either end of the bridge portion extends along at least a portion of the facial pad.

Preferably the bridge portion is substantially hollow at least at either end of the bridge portion to transport a flow of gases there through.

Preferably either end of the bridge portion is configured to couple a gas flow path of a breathing circuit.

Preferably the nasal prong, or each nasal prong, extends from, and is fluidly coupled to, a respective end of the bridge portion.

Preferably the bridge portion comprises an annular cross section along at least a substantial portion of the length of the bridge portion.

Preferably the bridge further comprises a fourth hinge adjacent the third hinge, or a pair of fourth hinges adjacent the respective pair of third hinges.

Preferably the fourth hinge or each hinge of the pair of fourth hinges is predisposed to have an acute curvature.

Preferably the fourth hinge, or each hinge of the pair of fourth hinges is predisposed to bend downwardly away from the nare(s) of the user and inwardly toward the facial cheek(s) of the user in situ.

Preferably each body portion comprises a facial pad contoured to engage upon a region of the user's face.

In a further aspect, the present invention may broadly consist in a nasal interface configured to stabilize prongs on a patient's face when forces are exerted on the interface, the nasal interface comprising: an elongate body having an overall curvature that generally corresponds to a patient's facial profile, the body configured to be coupled to a gases flow source and comprising at least one lumen extending at least partially through the body; a pair of prongs extending from the body and in fluid communication with the at least one lumen; and one or more hinges, at least one hinge disposed between the pair of prongs that is predisposed to bend in a predefined direction.

Preferably further comprising one or more facial pads configured to rest on a patient's face.

Preferably the at least one hinge disposed between the pair of prongs has a curvature that is generally inverted from the overall curvature of the elongate body.

Preferably the at least one hinge disposed between the pair of prongs is configured to bend inward towards the patient's face.

Preferably the nasal interface has a generally gullwing shape.

Preferably the nasal interface has a wavy shape.

Preferably the nasal interface has a curved space frame-like support structure.

Preferably the nasal interface bends in more than one dimension.

Preferably the one or more hinges comprises a notch.

Preferably the one or more hinges comprises a variable cross-sectional area.

Preferably the one or more hinges comprises a variable thickness.

Preferably the one or more hinges comprises two or more materials with different flexibilities.

Preferably the one or more hinges comprises an elastic hinge that is configured to be pre-stressed before application to a patient.

Preferably the one or more hinges comprises a barrel and pin.

Preferably the one or more hinges comprises a ball and socket.

In a further aspect, the present invention may broadly consist in a nasal interface comprising: an elongate body comprising at least one lumen extending at least partially through the body, the body configured to be coupled to a gases flow source; one or more prongs extending from the body and in fluid communication with the at least one lumen; and one or more hinges that are predisposed to bend in predefined directions; wherein the one or more hinges are configured to stabilize a position of the one or more prongs on a patient's face when forces are exerted on the nasal interface.

Preferably further comprising one or more facial pads configured to rest on a patient's face.

Preferably at least one of the one or more hinges is located adjacent to or between the one or more prongs.

Preferably at least one of the one or more hinges is configured to bend inward towards the patient's face.

Preferably at least one of the one or more hinges is configured to bend downward.

Preferably the nasal interface has a generally gullwing shape.

Preferably the nasal interface has a wavy shape.

Preferably the nasal interface has a curved space frame-like support structure.

Preferably the nasal interface bends in more than one dimension.

Preferably the nasal interface comprises two separate sides that are coupled by an over-strap bridge.

Preferably the one or more hinges comprises a notch.

Preferably the one or more hinges comprises a variable cross-sectional area.

Preferably the one or more hinges comprises a variable thickness.

Preferably the one or more hinges comprises two or more materials with different flexibilities.

Preferably the one or more hinges comprises an elastic hinge that is configured to be pre-stressed before application to a patient.

Preferably the one or more hinges comprises a barrel and pin.

Preferably the one or more hinges comprises a ball and socket.

In a further aspect, the present invention may broadly consist in a nasal interface comprising: an elongate body comprising at least one lumen extending at least partially through the body, the body configured to be coupled to a gases flow source; and one or more prongs coupled to the body and in fluid communication with the at least one lumen; wherein the elongate body has a shape that generally corresponds to an anatomical contour of a patient's or a group of patients' facial profile.

Preferably the group of patients is one of premature babies, neonates, infant, paediatrics or adults.

Preferably the tubular body is initially malleable.

Preferably the shape of the tubular body is set through a hardening process.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The term "gullwing" as used in this specification means a shape that comprising of two crests (or crest-like regions) and a trough (or trough-like region) located between such crests, or two troughs (or trough-like regions) and a crest (or crest-like region) located between such troughs, when viewed either as a top or bottom view of the patient interface (for example when the sequence of respective crests or troughs are drawn as a line diagram). Such crests or troughs may transition between each other in a relatively arcuate or curved manner. Optionally, such crests or troughs may be shaped or curved to substantially match or assimilate to facial contours or profile of a typical user's face.

The term "wavy" as used in this specification means a shape that comprises of a plurality of crests (or crest-like regions) and troughs (or trough-like regions), and comprising of at least one trough (or trough-like region) or of at least one crest (or crest-like region) disposed between respectively a pair of crests (or crest-like regions) or at least one trough (or trough-like region) disposed between respectively a pair of crests (or crest-like regions), when viewed from when viewed either as a top or bottom view of the patient interface (for example when the sequence of respective crests or troughs are drawn as a line diagram). Such crests or troughs may transition between each other in a relatively arcuate or curved manner. Optionally, such crests or troughs may be shaped or curved to substantially match or assimilate to facial contours or profile of a typical user's face.

The term "space frame" as used in this specification means a structure that provides for a substantially hollow scaffolding or supporting structure upon or to which a gas delivery line or conduit may be connected or otherwise attached or supported for delivery a gas to a user or a gas outlet of a patient interface (e.g. a nasal prong or pair of nasal prongs).

Where reference is made to a "pre-form", such a pre-formed element means an element that is manufactured or moulded or constructed or assembled so as to provide for a shape or configuration capable of providing for a deformed or displaceable response in a preferential geometry.

Where reference is made to a "preferential geometry", this means a predetermined or preferred plane (or planes) or axis (or axes) of hinging or bending or deforming or displacement.

Where reference is made to a "de-coupling", this means that there is at least a partial isolation or dampening or absorption (or some other mode), preferably a mechanical mode but not limited to this mode, in which forces or movements (or both) experienced or applied to a first region or part of the interface are at least minimised from being entirely transferred to another region or part of the interface.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which FIGS. 1-20 illustrate an embodiment of a patient interface according to this invention:

FIG. 1 is a front elevational view of a nasal interface known in the art.

FIG. 2 is a top plan view showing the bending of the nasal interface of FIG. 1 when forces are applied.

FIGS. 12A-B are various views of an embodiment of a notch hinge.

FIGS. 13A-D are various views of different embodiments of a notch hinge.

FIGS. 16A-B are various views of an embodiment of a variable thickness hinge.

FIGS. 17A-B are various views of an embodiment of a composite hinge.

FIG. 20 is a front elevational view of a dynamic nasal interface with a ball and socket hinge.

DETAILED DESCRIPTION OF PREFERRED EMBODIMENTS

Figure 1:
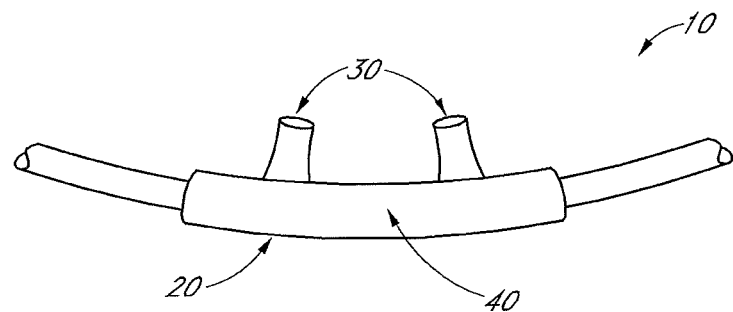

The foregoing description of the invention includes preferred forms thereof. Modifications may be made thereto without departing from the scope of the invention.

It is desirable to provide for a patient interface in a manner that conforms to a user's changing facial geometry or which is configured in a manner to maintain a stable position upon the user or to at least help improve the maintenance of stability when external forces are applied to such a patient interface.

In achieving one or both of these outcomes, or yet other outcomes, the provision of alternative patient interfaces with improved stability and/or performance on the face of the user would be useful.

In one aspect, this invention relates to a patient interface, such as a nasal cannula, comprising a body to be positioned upon a user (preferably such as a user's face). The body including at least one (and preferably a pair of) nasal prong(s), the or each nasal prong including a lumen capable of being fluidly connected thereto for fluid communication with a supply of breathable gas. The, or each, nasal prong to be in a configuration either inserted into, or to direct a flow of gas toward, a nare or the nares of the user's nose. The body includes at least one element responsive to force(s) or movement(s), or both, experienced by at least a first region of the patient interface from being transferred to at least one other region of the patient interface.

In relation to such an invention, reference is made to the accompanying drawings which detail specific embodiments thereof. Details of the specific embodiments are provided in the various sections below.

Before the specific embodiment details, the following description relates to the invention as detailed above. For example, such an interface can include an element which facilitates the reduction in transfer of a force or movement, or both, as applied to at least a first region of the interface from being transferred to at least another region of the interface. It will be appreciated such an element may be the hinged portion as detailed below with reference to the figures and specific embodiment descriptions. It will also be appreciated that a first region may be any part, component, zone or area of a patient interface, which may be exposed to a force or movement (or both) imparted by a user directly, or whether imposed by a component of a breathing circuit or headgear or other componentry associated with a patient interface and breathing circuits providing for a supply of breathable gas, or other items that could be found in the user's vicinity e.g. pacifier, blanket, cushion, toys etc.

The element of this invention is designed to respond in a manner to localise the force or the movement, or both, experienced by the at least first region.

It may also be that the element is able to respond in a way so as to minimise or prevent transfer of the force or the movement, or both, from the at least first region to at least one other region of the patient interface. The outcome or result from this response is the ability for such an interface to be more stable when installed or positioned on a user.

In this context, it will be appreciated a patient interface may be particularly those such as nasal cannula.

Extension of this invention may also have applicability to yet other interfaces, such as to masks (whether full face, oral, nasal, nasal pillow or oro-nasal) or other derivatives or variants of these.

The element (or elements) incorporated into the interface preferably respond in a manner to maintain the at least one (and preferably the pair of) nasal prong(s) in the configuration of insertion in a nare or nares of the user's nose, or in the configuration of directing a flow of gas toward a nare or nares of the user's nose. For example, another desired outcome is that the response is such that the at least one (or preferably the pair of) nasal prong(s) maintain a stable position within or adjacent to the nares of a user's nose to which the prong(s) is directed.

The element's response operates to go at least some way toward preventing or minimising transfer of force or movement from the at least first region of the interface to at least one other region of the interface. Accordingly, a more stable interface can be provisioned for use by a user. In providing for a more generally stable interface, an improvement in user comfort may be achieved. An improvement in the delivery of therapy to a user may also be achieved. Both such achievements may together result in a more user friendly interface or device.

Advantageously, this invention enables an interface having the capability or inclusion of elements which are responsive in a manner such that the interface maintains an operational position upon the user.

In addition, the force or movement, or both, experienced by at least a first region of the interface are either, or both, of i) an applied force(s) or a movement(s) between the nasal prong(s) and body of the patient interface, or ii) an applied force(s) or a movement(s) between the body of the patient interface and the nasal prong(s). The element responds to such forces or movements in a way so as to at least substantially ameliorate the transfer of forces or movements to other parts of the interface, or to at least do so in a manner so as to retain the interface on the user in an operational or comfortable configuration, or to at least mitigate the potential for the interface becoming uncomfortable or moving out of a therapeutic operational configuration for the user.

In certain embodiments, the element is a deformable member or a member that can be deformed in response to the force or movement (or both).

Predetermined or preferential modes of deformation by the element in response to the applied force or movement, or both, being experienced by at least a first region of the interface may be provided. For example, the element may be deformable in certain preferential geometries, such as about at least one axis or at least one plane, or both. It will be appreciated the deformation may be in a plurality of axes or planes or geometries, such deformation being in a preferential direction so as to provide for the response by the element to the applied force or movement (or both). It will also be appreciated such deformation may be one or a combination of at least a compression or a tension or a torsion or bending or other flexion of the element or a plurality of elements.

In respect of the element, the response may also be one or a combination of any one of a changing shape, or a changing of position, or a changing of configuration.

Various embodiments of such an element include, but are not specifically limited to one or more of the following, each of which may be used in combination with each other, or connected by members or other sections or components so as to provide for a plurality of elements which in combination provide for a desired response to ameliorate the transfer of a force or movement to the interface from at least a first region:

hinges, pivots, articulated joints or articulately connected portions of the body or portions associated with the body, swivels, ball-and-socket type joints, pin-in-barrel type joints, materials which are relatively less flexible than other portions of the interface, materials which are relatively more flexible than other portions of the interface, materials of characteristics which change upon application of a force or movement, such as by increasing their resistance to the applied force or movement (or both), or by reducing their resistance to the applied force or movement (or both), or materials which are elastically deformable in response to the applied force or movement (or both), or materials which are preferentially deformable in particular or predetermined geometries and yet which may optionally be resistant to deformation in other particular or predetermined geometries, a pivot (or swivel) or region capable of pivoting (or swivelling), a hinge or a hinged region or region capable of being hinged relative to another component of the interface or another region of the interface, an articulation or articulated joint or region capable of being articulated.

The element can be configured to provide or to operate or to work in response to the force or movement or both to prevent or minimise or at least reduce the overall force of movement experienced by the at least first region of the interface from being transferred to at least one other region of the interface.

The element may be a structure or a mechanism or a material characteristic or any combinations of structure, mechanism and material characteristic, incorporated into the interface, or may be a region of the interface incorporating one or a plurality of such elements in, or upon the interface.

In certain forms, the element may have predetermined or preferential modes of deformation in response to the applied force or movement. For example, the element may be deformable about at least one axis or at least one plane, or about a preferential first geometry, or may be deformable by one or a combination of a compression or a tension or torsion or bending or other such flexion.

One or a plurality of elements can be utilised and incorporated into the interface, such elements may operate or work or provide for the response on their own or may do so in combination with each other. Certain combined response from a plurality of elements may have advantages in that some elements may provide for a response to ameliorate the transfer of a force or movement from one region of the interface to other regions, and yet other elements respond in a different manner. For example, different elements may have different modes of response or be connected to each other, operatively or not, or to other parts of the interface in desired manners. Such a combined response or use of elements can preferably allow for an overall improvement in the comfort or stability of the interface during use on a user.

An element as incorporated in an interface of this invention may desirably be provided as one or more of:

an isolator or a region of isolation, an absorber or a region of absorption, a dampener or a region of dampening, or the any other structure or mechanism providing for a reactive response to a force(s) or movement(s) imparted to at least a first region of the patient interface from being transferred to at least a second or another region of the patient interface. In certain forms, the element can provide for a so called de-coupling of forces or movement (or both) which is applied to at least the first region of the interface from being transferred to at least one other region of the interface.

The response of an element may therefore be at least one (or a combination) of an isolation or an absorption or a dampening or a reduction or a de-coupling of the force(s) or movement(s) imparted to at least the first region from being transferred to at least one other region of the patient interface during use by a user.

Provision may be made so as to include an element which has a pre-form so as to be deformed or displaced in a preferential geometry or dimension as its response to the force or movement (or both).

For example, the element can facilitate a preferential bend or flexure or twist or torsion or a preferential or predetermined pivot or stretch or compression of a material(s) or a component(s) forming the body of the interface.

The element may be a region of different material characteristic or structure, such a as spongy material or a material capable of withstanding a tension, but not a compression, or a compression but not a tension, or allowing of a stretch or extension (or a compression) of a material or components of the element in certain geometries yet resistive to stretching or tension in other geometries.

Various configurations of elements, such as ball-and-socket joints may be provided which are provided between different regions of an interface, such as for example between an off-centre body portion of a nasal cannula interface (e.g. a left or a right body portion, or both) and a central portion or region (e.g. a bridge portion which may be in the septum area of a user), such an element facilitating a response which reducing the transfer of a force or movement to other parts of the interface, thereby helping to improve user interface comfort and continued maintenance of therapy delivery.

Yet other variations include sections of an interface in which the element is to be located, for example as a hinged portion or a pivot or swivel jointed portion or region so as to allow for the element to preferentially bend or accommodate an applied force or movement.

The force(s) or movement(s) can be any which are applied to or which the interface may experience. Typically, certain forces or movements may be resultant from a user of the interface changing their facial geometry to which the interface is retained or located or positioned, or such as by a user pulling or applying a force or movement on or to the interface or an associated headgear thereof, or a breathing circuit or other componentry of the interface applying a force or movement, such as by weighing down upon, a portion of the interface or a headgear associated thereof.

Changes in interface user facial geometry, such as during speech, eating, sleeping or other facial distortions and between relaxed and exaggerated conditions, can also contribute to forces or movements being applied or imparted to a region or regions of an interface.

The elements of this invention are beneficially configured to assist in reducing the likelihood of such forces or movements from impacting on comfort or delivery of therapy to a user of the interface.

In various examples, where the patient interface is a nasal cannula, the applied forces or movement between the nasal prong(s) and body of the patient interface, or between the body of the patient interface and the nasal prong may encourage the problem of prong flicking (where the nasal prongs of an interface move about with the nares of a user's nose or may even be removed entirely from the nares). Nasal prongs moving about in the nares may irritate a user, whilst removal or dislodgment of the prongs from the nares impacts on the preferred delivery of therapy to the user. Systems or methods to assist in avoiding prong flicking are advantageous.

In one particular embodiment, at least one element or at least one of the elements, is located in the bridge region of a nasal cannula patient interface, such as substantially adjacent the septum region of a user.

In other embodiments, the interface can comprise of a plurality of elements utilised on their own or in combination with other elements to provide for the response.

In still further embodiments, the at least one element can be a hinged portion located or positioned as a bridge between a left body portion and a right body portion, each of the body portions together forming the body of an interface to be located upon a user's face, such a hinged portion providing for a preferential region of deformation in response to at least a first region of the body, or a portion of the body, experiencing a force or movement (or both) resulting from a change in the facial geometry of the user.

In all embodiments discussed here, there may be an additional but optional configuration of the interface to be generally conformed or conformable or be anatomically shaped for a user's face or part of the body to which the interface is to be located. In this manner, a patient interface that is substantially conformed or conformable to the geometry of a user's face may allow for the element to respond to the force or movement (or both) to substantially maintain the interface in a preferred therapy delivery configuration for a user.

Provided below is yet further specific embodiments according to this invention and as illustrated with reference to the accompanying drawings.

An aspect of at least one of the embodiments disclosed herein includes the realization that with at least nasal interfaces, the stability of the nasal interface on the face is important, as movement of the nasal interface can cause severe irritation to the nares or cause the prongs to displace out of the patient's nares, which can lead to prevention or interruption of therapy.

The current methods of retaining nasal interfaces to a patient's face have disadvantages that can cause the prongs to displace out of the nares or irritate the sensitive area of the nares. These undesired consequences can occur from a variety of reasons, including but not limited to, incorrect application, incorrect sizing, patient position, facial movements and abnormal facial geometries.

In the case of tubing that is routed around the patient's ears, the tubing can fall off the ears and cause the prongs to dislodge from the nares. The tubing can also be displaced when the patient lies on the side of their head, causing the prongs to dislodge from the nares or rub against the sides of the nares. Furthermore, the use of a strap or an elastic band is disadvantageously prone to sliding of the nasal interface relative to the patient's head especially when the patient turns his/her head on a pillow, causing the prongs to dislodge from the nares or cause severe irritation. Other external forces can also cause the nasal prongs to dislodge from or irritate the nares, such as the supply tube getting caught on other objects or the patient pulling on the tubing.

Previously, adhesive medical tape has been used to retain the nasal interface in place. However, the fixation of the interface to the patient's face has been found to cause issues with the retention of the prongs in the patient's nares, especially for infants and neonates. When the patient's face is squeezed from lying on the side, current nasal interfaces tend to bend at the bridge of the nasal interface in a direction away from the face. The bending of the interface causes the prongs to displace out of the patient's nares, or become crushed against the sides of the patient's nose so as to cause at least a partial blockage of the gases being delivered to the patient.

It will be appreciated that in some embodiments the patient interfaces as described herein may be utilised in conjunction with a headgear system for locating or securing such a patient interface upon a user's face, yet such patient interfaces remain capable of being able to respond to forces or movements (or both) when used in such an arrangement.

In yet other embodiments, it will be appreciated that a headgear arrangement or configuration may operate to take some of the load the patient interface may experience due to forces or movements (or both) experienced by the interface, whilst the interface operates to take some of the load also.

Thus, in accordance with at least one of the embodiments disclosed herein, a nasal interface can be used that prevents or substantially reduces the likelihood of prongs displacing out of the patient's nares or irritating the nares as caused by facial movements or external forces.

A nasal interface can be configured to stabilize prongs on a patient's face when forces are exerted on the interface. The nasal interface can include an elongate body having an overall curvature that generally corresponds to a patient's facial profile, the body being configured to be coupled to a gases flow source and having at least one lumen extending at least partially through the body. The nasal interface can have prongs extending from the body and in fluid communication with the at least one lumen. The nasal interface can have one or more hinges, at least one hinge can be disposed between the pair of prongs, or between the nares when in use, that is predisposed to bend in a predefined direction.

The nasal interface can include one or more facial pads configured to rest on a patient's face. In some embodiments, the at least one hinge disposed between the pair of prongs can have a curvature that is generally inverted from the overall curvature of the elongate body. The at least one hinge disposed between the pair of prongs can be configured to bend inward towards the patient's face. The nasal interface can bend in more than one dimension.

The nasal interface can have a generally gullwing shape. In some embodiments, the nasal interface can have a wavy shape. In some embodiments, the nasal interface can have a curved space frame-like support structure.

The one or more hinges can include a notch. The one or more hinges can include a variable cross-sectional area. The one or more hinges can include a variable thickness. The one or more hinges can include two or more materials with different flexibilities. The one or more hinges can include an elastic hinge that is configured to be pre-stressed before application to a patient. The one or more hinges can include a barrel and pin. The one or more hinges can include a ball and socket.

In some embodiments, a nasal interface can include an elongate body having at least one lumen extending at least partially through the body, the body being configured to be coupled to a gases flow source. One or more prongs can extend from the body and be in fluid communication with the at least one lumen. The nasal interface can include one or more hinges that are predisposed to bend in predefined directions, wherein the one or more hinges are configured to stabilize a position of the one or more prongs on a patient's face when forces are exerted on the nasal interface.

The nasal interface can include one or more facial pads configured to rest on a patient's face. At least one of the one or more hinges can be located adjacent to or between the one or more prongs, or in addition, along one of the facial pads. At least one of the one or more hinges can be configured to bend inward towards the patient's face. At least one of the one or more hinges can be configured to bend downward. The nasal interface can bend in more than one dimension.

The nasal interface can have a generally gullwing shape. In some embodiments, the nasal interface can have a wavy shape.

The nasal interface can have a curved space frame-like support structure.

In some embodiments, the nasal interface can have two separate sides that are coupled by an over-strap bridge.

The one or more hinges can include a notch. The one or more hinges can include a variable cross-sectional area. The one or more hinges can include a variable thickness. The one or more hinges can include two or more materials with different flexibilities. The one or more hinges can include an elastic hinge that is configured to be pre-stressed before application to a patient. The one or more hinges can include a barrel and pin. The one or more hinges can include a ball and socket.

In some embodiments, a nasal interface can include an elongate body having at least one lumen extending at least partially through the body, the body configured to be coupled to a gases flow source. One or more prongs can be coupled to the body and be in fluid communication with the at least one lumen. The elongate body can have a shape that generally corresponds to an anatomical contour of a patient's or a group of patients' facial profile.

The group of patients can be one of premature babies, neonates, infant, paediatrics, teens or adults. In some embodiments, the tubular body can be initially malleable. The shape of the tubular body can be set through a hardening process.

It has been discovered that the behaviour of a nasal interface under loading can be controlled to improve its stability performance. In this disclosure, nasal interfaces that prevent or substantially reduce the likelihood of prongs displacing out of the patient's nares or irritating the patient's nares as a result of facial movements or external forces are described.

Human facial geometry varies greatly due to a large range of factors. These factors include but are not limited to gender, ethnicity, age and medical conditions. Incorrect sizing and geometry of nasal interfaces can adversely affect the stability and usability of the nasal interfaces. Other causes that can affect stability include, but are not limited to, incorrect application, patient position, patient crying and abnormal facial geometries.

Furthermore, when a patient speaks, eats, cries or has their facial features distorted or exaggerated in any way, it can affect the stability of an interface on the patient's face. More prolonged changes to facial features can arise from aspects such as patient position while sleeping for example. Long term changes in geometry can occur from patient growth and injury recovery.

When supporting items on a patients face, any external forces can affect device stability as well. In the case of a transverse nasal interface, external forces can arise from a range of sources such as patients pulling on the interface, breathing circuit weight being transmitted to the interface, head strap retention forces or any connected tubing getting caught on other equipment.

Nasal interfaces 10 traditionally have a manifold 20 with prongs 30 extending from the manifold 10, as shown in FIG. 1. A bridge 40 is connected between the prongs 30 and may allow for fluid communication between the prongs 30. This design can be unstable on the patient's face, which can lead to dislodgement of the nasal prongs from the patient's nares and adverse effects on therapy to the patient. Oftentimes, the dislodgement of the prongs from the nares is a result of the interface's mechanical reaction to a particular force applied to it.

Figure 2:
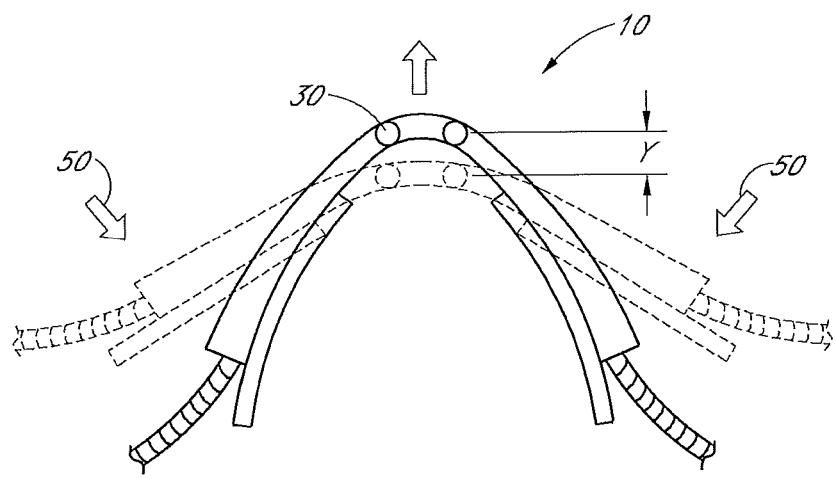

The behaviour of a nasal interface under loading, such as from a patient speaking or lying on the side of their face, can be affected by a variety or combination of different interface features, such as interface geometry and material properties. For example, FIG. 2 shows a traditional nasal interface 10 with forces 50 exerted to the sides of the interface. Forces 50 may be exerted on the interface, for instance, when the patient is lying on the side of their face or when the patient's face is squeezed. A traditional nasal interface 10 in a relaxed state is shown by dotted lines in FIG. 2. FIG. 2 also shows the nasal interface in a squeezed state when forces 50 are exerted on the interface. With continued reference to FIG. 2, when the forces 50 are exerted on the sides of the nasal interface, most traditional interfaces naturally tend to bend upward in the figure or away from the patient in the middle near the prongs 30 because of the geometric design and material properties of the interface. The bending of the interface displaces the position of the prongs 30 such that they flick out of the patient's nares or rub against the sides of the nares, irritating the sensitive skin of the nares. FIG. 2 illustrates the prongs 30 displaced from their normal relaxed positions by a distance of Y.

As described herein, nasal interface stability can be improved by utilizing one or more of anatomically formed shapes and geometrically dynamic forms in the interface design. These designs can at least partially mechanically react to facial movements or external forces to help maintain nasal prong stability.

With a traditional interface's straight design, additional retention such as adhesive tape is often required to secure the interface to a patient's facial geometry. FIG. 3A is a bottom view illustrating a traditional interface 10 on a patient's face 60. As shown in this figure, retention forces F may be required to secure the interface 10 on the patient's face 60. However, the retention forces F can change the shape of the interface 10 and the elastic properties of the nasal interface can produce restorative forces opposing the retention force. These restorative forces can cause the retention method to detach and cause the prongs to apply pressure on the inside of the nares, causing sores. The unnatural bent shape of the nasal interface can also cause the prongs to not fit properly and cause sores as well.

The following describes components and properties of example nasal interfaces in greater detail. Sub-headings are used, such as "Anatomically Formed Interfaces" and "Dynamic Interfaces." These sub-headings are not, and should not be construed as limiting. For example, aspects of one or more embodiments described under the Anatomically Formed Interfaces sub-heading can also apply to one or more embodiments described under the Dynamic Interfaces subheading, and vice versa.

Anatomically Formed Interfaces

Figure 3B:
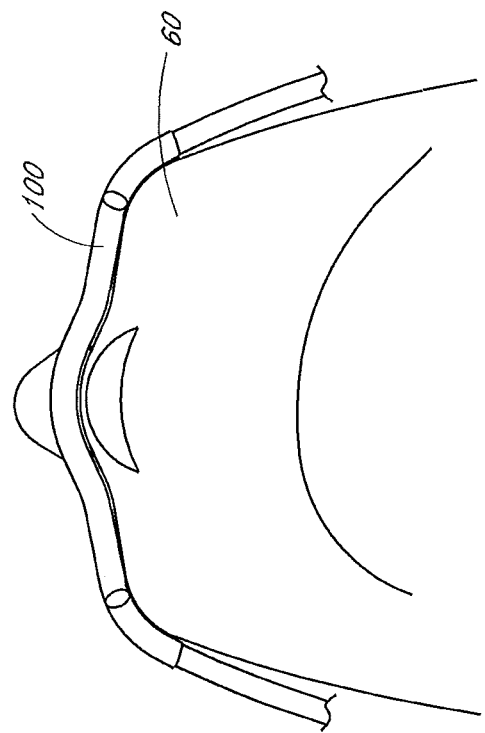
FIG. 3B is a bottom plan view of an embodiment of an anatomically formed nasal interface on a patient's face.
Figure 3A:
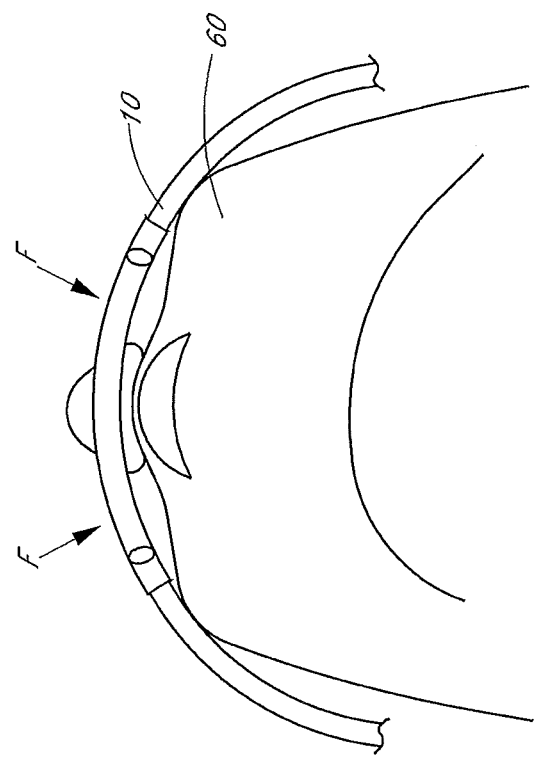
FIG. 3A is a bottom plan view of the nasal interface of FIG. 1 on a patient's face.

Anatomically formed interfaces 100 are shaped to fit the facial profile of a given population, as illustrated in FIG. 3B. These interfaces 100 incorporate shapes which are anatomically curved to fit the three-dimensional facial contours of a particular demographic; e.g., premature babies, neonates, infant, paediatrics and adult. The anatomically curved interface's 100 shape can significantly increase the stability of an interface on a patient's face 60 and can reduce the incidences of prong displacement out of the patient's nares.

Whilst not limiting, the illustrated embodiments may have particular applicability to neonates. For example, such interfaces may be especially suitable for use with neonates due to the increased facial distortion occurring in neonates, due to the small size of their head/face and any movements may be accentuated by their relatively small size.

The anatomically formed interface 100 conforms to a patient's facial profile while in a natural, relaxed shape. The interface does not need to be bent by retention forces to stabilize the interface on the patient's face 60 and thus no restorative forces are produced. Even when adhesive tape is used to fix the anatomically formed interface to the patient's face, no restorative forces are present because the tape does not bend the interface. The prongs remain in the patient's nose in a natural, unstressed position and the likelihood of dislodgement or injury to the patient's nares is reduced compared to traditional interfaces. Another advantage of the anatomically formed interface 100 is the reduced need for adhesive tapes to retain the interface on the patient's face 60, reducing the likelihood of skin irritation or injury. The anatomically formed interface 100 has increased stability compared to a traditional interface and there is less need to tape the interface to the patient's face to maintain stability.

The anatomically formed interface 100 can be manufactured using plastic moulding methods to form a predetermined curved shape which has been identified to fit a given demographic of patient. For example an underdeveloped premature baby has a different facial profile to that of a fully developed term baby so for each of these demographics a common facial profile can be identified which compliments a high percentile of that population. A plurality of different sizes and shapes of interfaces can be produced to fit a wide variety of facial profiles.

In some embodiments, the anatomically formed interface can be modified by the patient or caregiver after manufacture. The anatomically formed interface can be flexible and formable into a custom shape to fit the patient's face. For example, the interface can be at least partially made of a malleable material such as medical putty or flexible plastic. The patient or caregiver can shape the malleable interface to generally correspond to the contours of the patients face and provide a stable fit with the patient's face.

In other examples, the anatomically formed interface can have a malleable frame extending through the interface that can be bent to generally match the contours of the patient's face and provide a structural shape to the interface. In order for the interface to maintain its shape after shaping, a post annealing process can be applied to the malleable frame in some embodiments.

Other types of formable interface materials can include one or more of silicone, rubber (synthetic or natural), thermoplastic and thermosetting polymers. The composite materials can be fabricated by co-moulding or overmoulding. These materials can be initially malleable so that they can be shaped to the patient's face shape, and then become rigid after a period of time or through an active hardening process, such as a UV treatment or heat treatment.

Dynamic Interface

A dynamic interface incorporates one or more hinges along the device that reacts to facial movements, both natural and forced, and external forces exerted on the interface. The hinges can minimise the effects of the facial movements and external forces on the fitment of the interface on the patient's face, particularly on the placement of the prongs in the patient's nares. As used herein, hinges refers generally to portions on the interface that are configured to bend in one or more directions. The hinges can be configured to bend in a predefined direction or directions, and in some embodiments the hinges can be restricted from bending in certain directions.

Figure 4A:
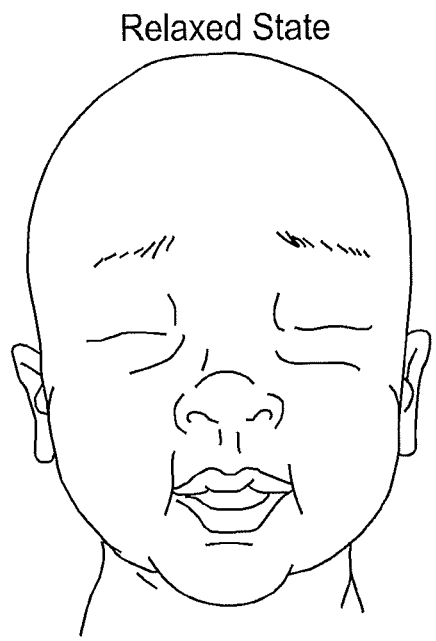
FIGS. 4A-B are various views of a patient's face in a relaxed state.
Figure 4C:
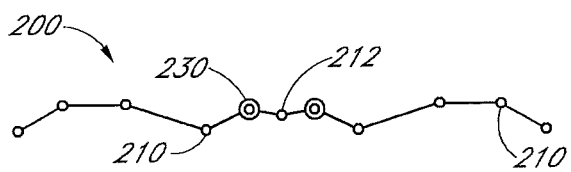
FIG. 4C is a wireframe profile of an embodiment of a dynamic interface in a relaxed state.
Figure 4B:

FIGS. 4A-B illustrate an example of a relaxed facial shape of an infant and FIG. 4C illustrates a schematic of the geometric shape of a dynamic interface 200 on a relaxed face. FIG. 4A is a front view of an infant's face and FIG. 4B is a bottom view of the infant's face. FIG. 4C is a bottom view of a dynamic interface. The dynamic interface 200 can have one or more hinges 210. Preferably, the dynamic interface has a center hinge 212 disposed between the prongs 230. As can be noticed by comparing FIGS. 4B and 4C, the plurality of hinges 210 on the interface allows the interface 200 to conform to the general contours of the patient's face.

Figure 5A:
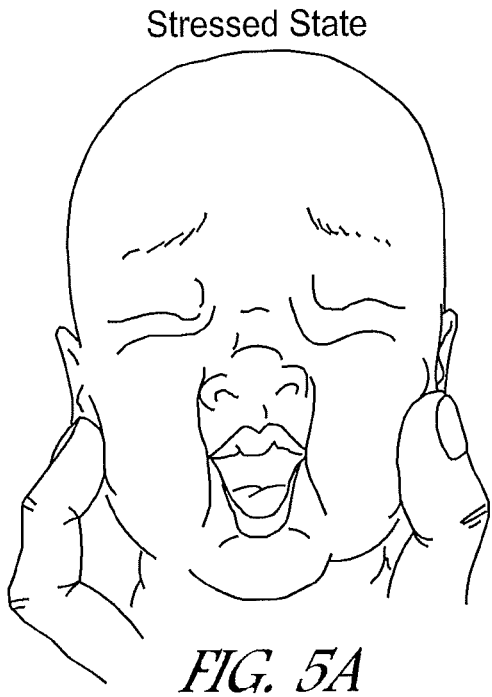
FIGS. 5A-B are various views of a patient's face in a stressed state.
Figure 5C:
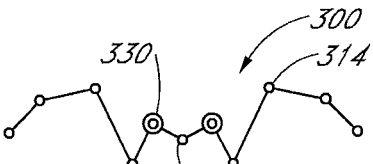
FIG. 5C is a wireframe profile of the dynamic interface of FIG. 4C in a stressed state.
Figure 5B:

FIGS. 5A-B illustrate a front view and a bottom view, respectively, of an example of a stressed or squeezed facial shape of an infant. FIG. 5C illustrates a bottom view schematic of the geometric shape of a dynamic interface 300 on a squeezed face. The squeezed face approximates, for example, the contortion of the face when patients lie on the side of their faces. As illustrated in FIG. 5C, the hinges 310 help conform the interface 300 to the shape of the contorted face and maintain the position of the prongs 330 in the nares of the patient. The dynamic interface 300 is particularly helpful in the case of infants who tend to exhibit exaggerated cheek movement.

Each hinge 310 can be configured to react to an applied force in a predetermined fashion and different hinges can react differently depending on their position on the interface. For example, a hinge 312 located in the region between the prongs 330 may bend downward toward the lips and/or inward toward the face to form a concave shape when viewed from the front, while the hinges 314 adjacent the cheeks of the patient may bend outward to form a convex shape around the cheeks. The hinge 312 can resist movement outwards normal to the face and minimise the movement of the prongs 330 out of the nares due to forces applied laterally on the device. In some situations, the bending of hinge 312 can be limited by the patient's anatomy. For example, the inward bending of hinge 312 can be limited by the philtrum of the patient, which can beneficially limit the displacement of the prongs 330. The forces applied to the interface may act on the other hinges (e.g., hinges 314 adjacent the cheeks) once the hinge 312 reaches its limit. Combinations of hinge types and hinge locations can allow the designer to control how an interface will react in a variety of situations. A hinge may be designed to allow for 1, 2 or 3 degrees of motion in any predefined direction depending on its desired function. Advantageously, an inherently stable interface can be developed that keeps the prongs in the patients nares under various loading conditions.

Figure 6A:
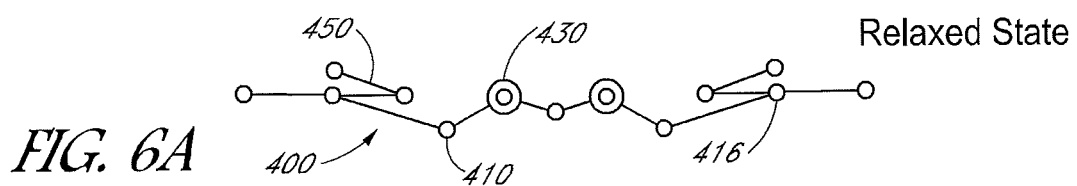
FIG. 6A is a wireframe profile of an embodiment of a dynamic interface in a relaxed state.
Figure 6B:
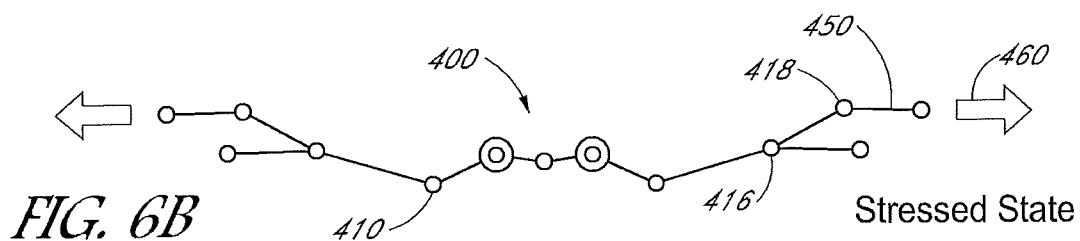
FIG. 6B is a wireframe profile of the dynamic interface of FIG. 6A when external forces are applied in a stressed state.

FIGS. 6A-B illustrate an example of how a dynamic interface 400 can react to external forces 460. As shown in FIG. 6A, an extension 450 can be coupled to the dynamic interface 400 with a hinge 416. The extension 450 can be a part of the dynamic interface 400 that connects to external devices, or the extension 450 can be a part of an external device that connects to the dynamic interface 400. For example, the extension 450 can be a part of the dynamic interface 400 and connectable to a tube, or the extension 450 can be a part of a tube that connects to the interface 400. The hinge 416 can be located at the connection point of the extension 450 and the interface 400. With reference to FIG. 6B any external forces 460, such as pushing or pulling on the tube, will be dampened by the reaction of the hinge 416 and reduce the forces being translated onto the dynamic interface 400. The external forces 460 can be at least partially isolated from affecting the positioning of the prongs 430 in the patient's nares. Preferably, another hinge 418 is located on the extension 450 for increased dampening ability of the extension 450. In some embodiments, further additional hinges can be disposed on the extension 450 for even more dampening ability.

The hinges and their positions on the interface can be customized to work effectively with the particular retention method of the interface. For example, with continued reference to FIGS. 5A-C, if the interface is configured to be secured to the cheeks with tape or some similar retention method, there can be one or more hinges located between the cheek section and the prongs to account for facial movements. Similarly, with reference to FIGS. 6A-B, if a head strap is connected to the extension 450, at least one hinge can be located between the head strap and interface to account for external forces.

Figure 7A:
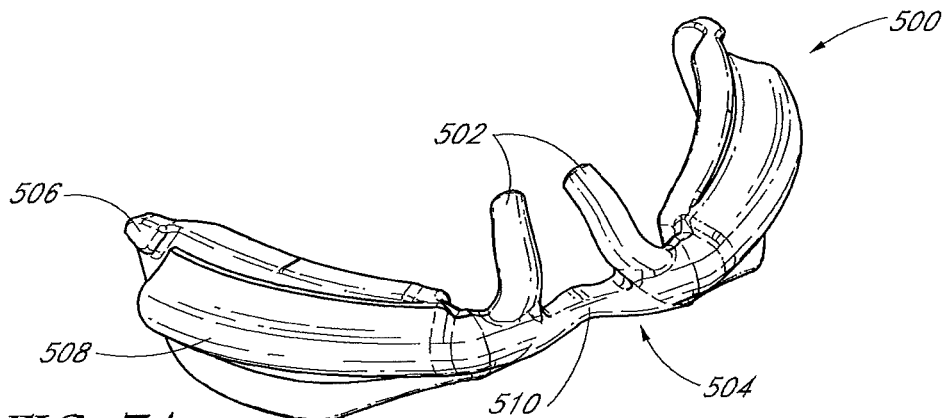
FIGS. 7A-B are various views of an embodiment of a dynamic interface, for example of a gullwing type shape.
Figure 7B:
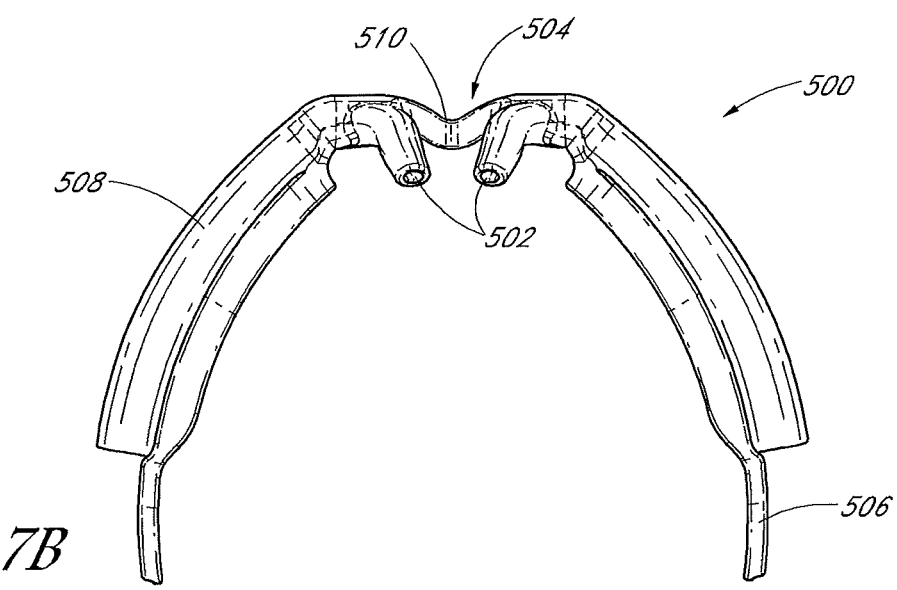

An example of a dynamic nasal interface 500 is illustrated in FIGS. 7A-B. The gullwing shaped dynamic interface 500 can have an overall curvature that generally corresponds to a patient's facial profile. The dynamic interface 500 can include one or more nasal prongs 502, a bridge 504 extending between the prongs 502 that is configured to be along a patient's upper lip beneath the nose in use, a pair of wings or facial pads 506 and integral tubing 508, all spaced generally symmetrically about the sagittal plane. The dynamic interface 500 is formed as an integral or unitary component with the tubing 508 in fluid communication with the prongs 502. The open end of each integrated tubing 508 is configured to receive a suitable breathing tube that is connected to a gases supply. The breathing tube may be adhered or otherwise coupled (or connected) to the interface tubing 508. Preferably, the tubing 508 includes two separate sides that have independent flow paths. However in some embodiments, the two sides can be in fluid communication, such as through a tube that extends across the bridge to connect the two sides of tubing.

The facial pads 506 are anatomically shaped with a size, shape and curvature that reflects the facial geometry of the intended patient. The anatomical shape of the facial pads 506 gives the interface a positive engagement with a patient's face at a predetermined position where the contour of the facial pads 506 matches the patient's facial contour. The pre-shaped facial pads 506 compliment the nasal prongs 502 by improving the accuracy and speed with which the prongs 502 can be placed and retained within a patient's nares.

Pre-shaping or contouring the facial pads 506 to the patient's facial features reduces the pressure applied to the patient's face by any retention mechanism (adhesive tape, headgear or other means). This reduces the likelihood of pressure sores upon the user. The positive engagement promoted by the anatomical shape of the facial pads 506 increases the stability of the interface 500 and the prong 502 and therefore improves comfort and efficacy of the treatment being administered. In some embodiments, the facial pads 506 can be wider at the outer portions and taper to be narrower toward the middle. Further examples of nasal interfaces may be as described in International Patent Application Publication No. WO 2012/053910, which is hereby incorporated by reference, in its entirety.

With continued reference to FIGS. 4A-B, the bridge 504 of the nasal interface 500 can have a bridge hinge 510 that is configured to bend inward toward the patient. As best illustrated in the FIG. 7B, the bridge 504 has an inverted curvature compared to the rest of the nasal interface such that the interface has a gullwing-like shape. The bridge hinge 510 is curved toward the rear of the interface 500 such that the bridge 504 is convex shaped when viewed from the front. The curvature of the bridge 504 predisposes the hinge 510 to bend inward toward the patient, as opposed to outward as in the case of traditional nasal interfaces.

Figure 7C:
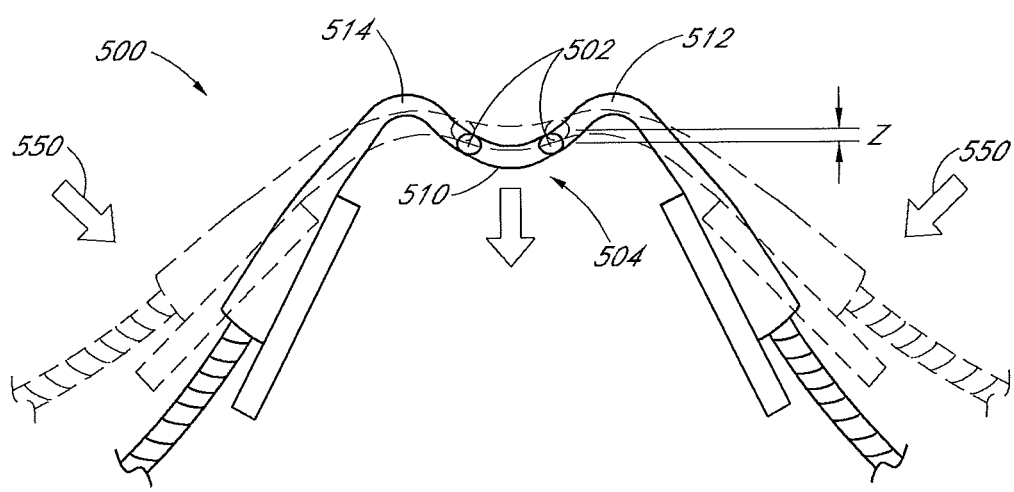
FIG. 7C is a top plan view showing the bending of the gullwing dynamic interface of FIG. 7A-B when forces are applied.

For example, FIG. 7C illustrates a nasal interface 500, for example having a generally gullwing type shape, with forces 550 exerted to the sides of the interface. Forces 550 may be exerted to the interface, for instance, when the patient is lying on the side of their face or when the patient's face is squeezed. The nasal interface 500 in a relaxed state is shown by dotted lines in FIG. 7C. FIG. 7C also shows the nasal interface in a stressed state when forces 550 are exerted on the interface. When the forces 550 are exerted on the sides of the nasal interface, the bridge 504 is inclined to bend inward at the bridge hinge 510, as shown by the central arrow in FIG. 7C. The inward bending of the bridge 504 displaces the prongs 502 inward closer to the patient, as opposed to outward away from the patient, where the prongs 502 may flick out of the nares, as is the case in traditional nasal interfaces. As discussed above, the bending of the bridge hinge 510 can be limited by the patient's anatomy. For example, the inward bending of the bridge hinge 510 can be limited by the philtrum of the patient, which can beneficially limit the displacement of the prongs 502. The nasal interface design helps reduce the risk of the prongs 502 flicking out of the patient's nares or rubbing against the sides of the nares.

The displacement distance of the prongs 502 can typically be less than compared to traditional nasal interfaces. FIG. 7C illustrates the prongs 502 displaced from their normal relaxed positions by a displacement of Z, which is in the opposite direction and typically a smaller distance compared to the displacement of Y shown in FIG. 2 for a traditional nasal interface. The nasal cannula hinges in at least three locations, the bridge hinge 510 and outer hinges 512, 514 on either sides of the prongs; whereas traditional nasal interfaces bend mainly at a single position at the bridge. The additional hinges of the nasal interface help stabilize the positions of the prongs 502 when the cannula is under stress and reduce the displacement distance, helping to keep the prongs in the nares of the patient and reduce the irritation of the nares by the prongs.

Figure 8A:
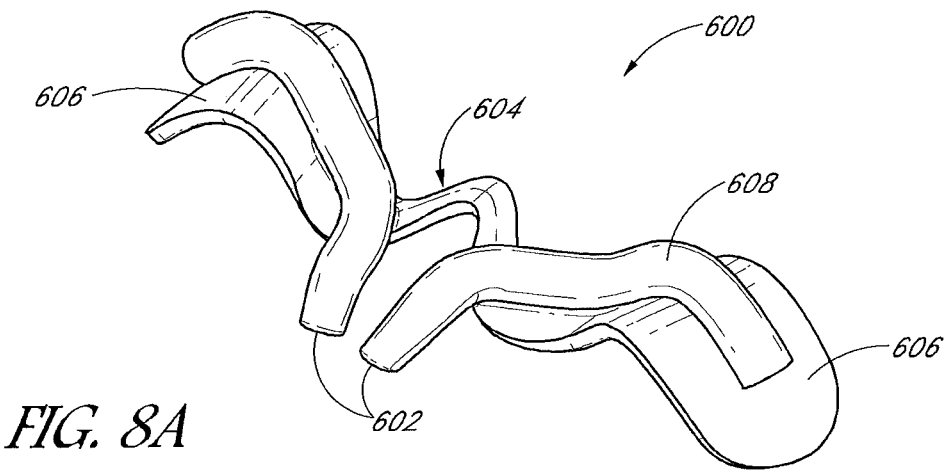
FIGS. 8A-C are various views of an embodiment of a dynamic interface, for example of a wavy type shape.
Figure 8B:
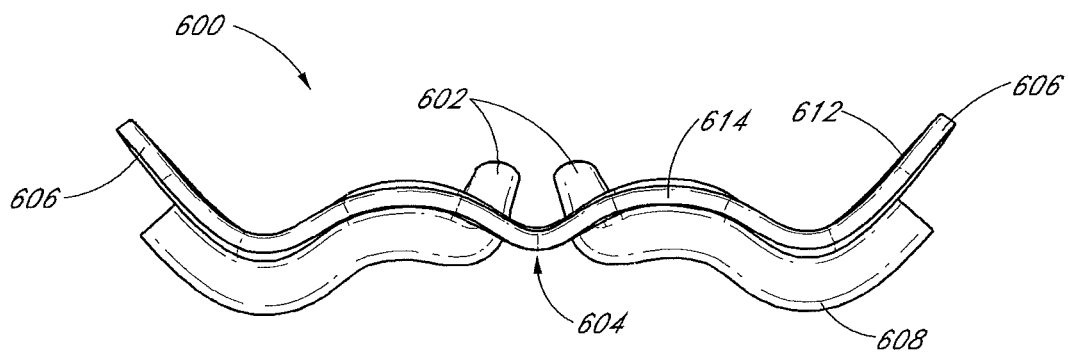
Figure 8C:
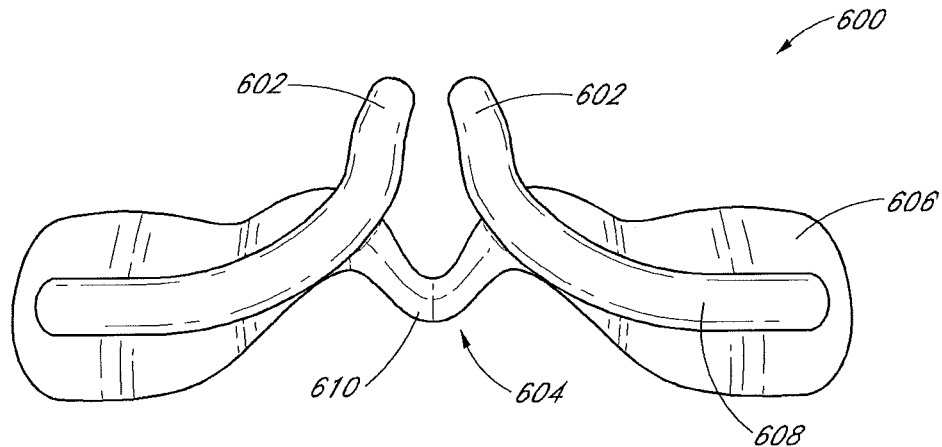

Another example of a dynamic nasal interface 600 is illustrated in FIGS. 8A-C. The dynamic interface 600, for example having a generally wavy type shape, includes one or more nasal prongs 602, a bridge 604 extending between the prongs 602, a pair of wings or facial pads 606 and tubing 608 coupled to the facial pads 606, all spaced generally symmetrically about the sagittal plane. The dynamic interface 600 can be formed as an integral or unitary component with the tubing 608 in fluid communication with the prongs 602. The open end of each integrated tubing 608 is configured to receive a suitable breathing tube that is connected to a gases supply. The breathing tube may be adhered or otherwise coupled (or connected) to the interface tubing 608. Preferably, the tubing 608 includes two separate sides that have independent flow paths. However in some embodiments, the two sides can be in fluid communication, such as through a tube that extends across the bridge to connect the two sides of tubing.

The facial pads 606 are shaped to generally match the anatomical shape of the facial geometry of an intended patient. As illustrated in FIG. 8B, the facial pads 606 can have a wavy shape that generally matches the shape of a patient's profile, as illustrated for example in FIG. 4B. The facial pads 606 can have an outer concave portion 612 configured to lie over the protruding cheeks of the patient and an inner convex portion 614 configured to lie over the creases between the cheeks and upper lip. The bridge 604 can have a concave shape to accommodate the bump of the upper lip and philtrum. The tubing 608 can follow the contours of the nasal interface 600.

The anatomical shape of the facial pads 606 gives the interface a positive engagement with a patient's face at a predetermined position where the contour of the facial pads 606 matches the patient's facial contour. The pre-shaped facial pads 606 compliment the nasal prongs 602 by improving the accuracy and speed with which the prongs 602 can be placed and retained within a patient's nares.

FIG. 8C illustrates a front view of the nasal interface 600. The facial pads 606 can be wider at the outer portions and taper to be narrower toward the middle. The bridge 604 can be integral with the facial pads 606 and in some embodiments connects the two facial pads 606. In some embodiments, the bridge 604 can be curved downward and have a hinge 610. The hinge 610 can be predisposed to bend downward such that when the nasal interface 600 experiences forces from facial movements or external forces, the bridge 604 can bend downward. The downward bending can help stabilize the prongs 602 and minimize movement of the prongs 602 in the sagittal plane (i.e., front/back) and coronal plane (i.e., up/down). The downward bending of the bridge 604 displaces the prongs 602 closer together, but does not displace the prongs 602 outward away from the nares, as is the case in traditional nasal interfaces. The nasal interface design helps reduce the risk of the prongs 602 flicking out of the patient's nares or rubbing against the sides of the nares.

FIGS. 9A-D illustrate another non-limiting example of a dynamic nasal interface 700. The dynamic interface 700 includes one or more nasal prongs 702, a curved space-frame support structure 703 with a bridge 704 extending between the prongs 702, a pair of wings or facial pads 706 and tubing 708 coupled to the facial pads 706, all spaced generally symmetrically about the sagittal plane. The dynamic interface 700 can be formed as an integral or unitary component with the tubing 708 in fluid communication with the prongs 702. The open end of each integrated tubing 708 is configured to receive a suitable breathing tube that is connected to a gases supply. The breathing tube may be adhered or otherwise coupled to the interface tubing 708. Preferably, the tubing 708 includes two separate sides that have independent flow paths. However in some embodiments, the two sides can be in fluid communication, such as through a tube that extends across the bridge to connect the two sides of tubing.

The facial pads 706 can be shaped to generally match the anatomical shape of the facial geometry of an intended patient. As illustrated in FIG. 9B, the facial pads 706 can be disposed toward the outer portions of the dynamic interface 700 and curved to match the shape of a patient's cheeks. In some embodiments, the facial pads can extend further toward the middle of the dynamic interface and/or can be connected as a continuous pad extending across the entire dynamic interface. The facial pads 706 can have a concave portion 712 configured to lie over the protruding cheeks of the patient.

The anatomical shape of the facial pads 706 gives the interface a positive engagement with a patient's face at a predetermined position where the contour of the facial pads 706 matches the patient's facial contour. The pre-shaped facial pads 706 compliment the nasal prongs 702 by improving the accuracy and speed with which the prongs 702 can be placed and retained within a patient's nares.

Figure 9A:
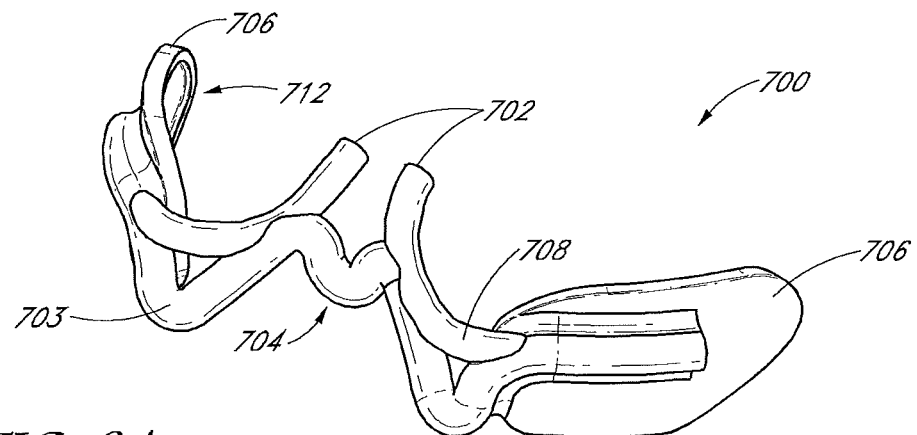
FIG. 9A is a top perspective view an embodiment of a space frame dynamic interface.
Figure 9B:
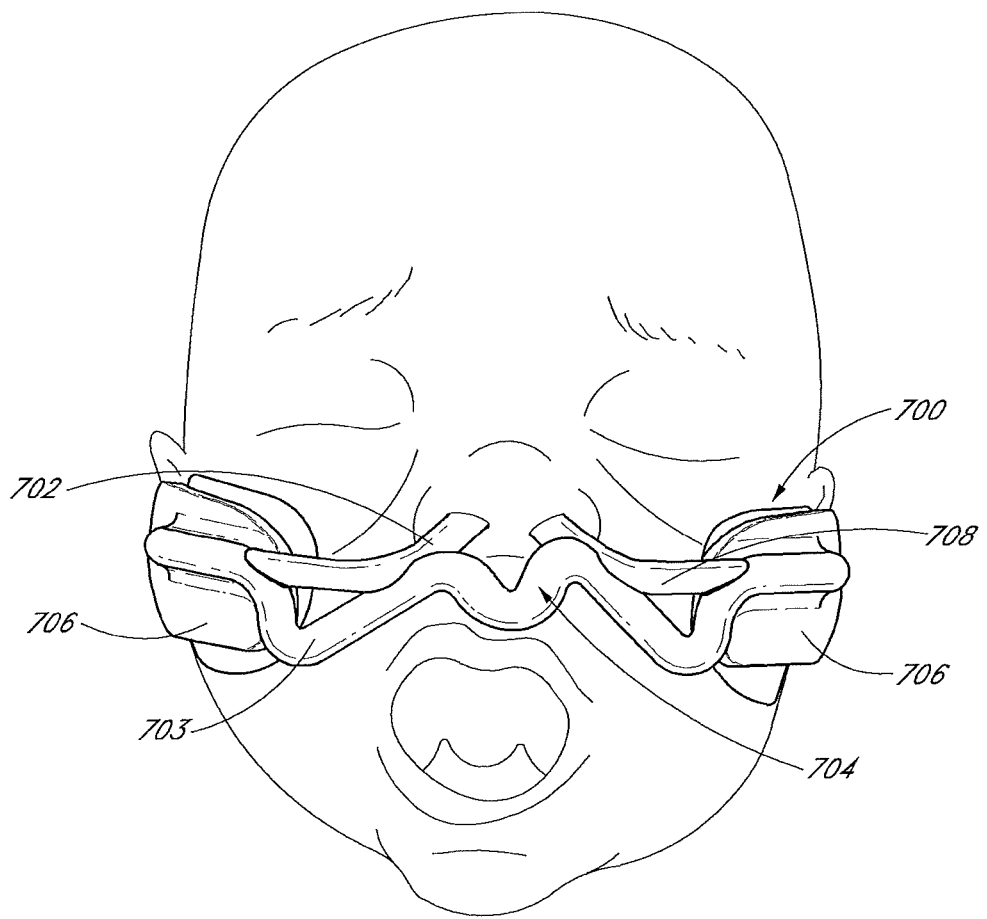
FIGS. 9B-D are various views of the space frame dynamic interface of FIG. 9A on a patient's face.

With continued reference to FIGS. 9A and 9B, the nasal prongs 702 and tubing 708 can be at least partially supported by the support structure 703. The support structure 703 can be coupled to the facial pads 706 and include a bridge 704 between the prongs 702. The dynamic interface 700 with the space frame-like support structure 703 helps stabilize the interface from three-dimensional changes in the patient's facial geometry and helps maintain the prongs 702 in the nares of the patient. In some embodiments, the support structure 703 can be hollow and in fluid communication with the prongs 702 such that the prongs 702 are in fluid communication with each other. In other embodiments, the prongs 702 may be separate and not fluidly connected with each other, at least not through the support structure 703. In these embodiments, the support structure 703 can be solid, hollow or filled with material such as for example foam or a malleable wire frame.

Figure 9C:
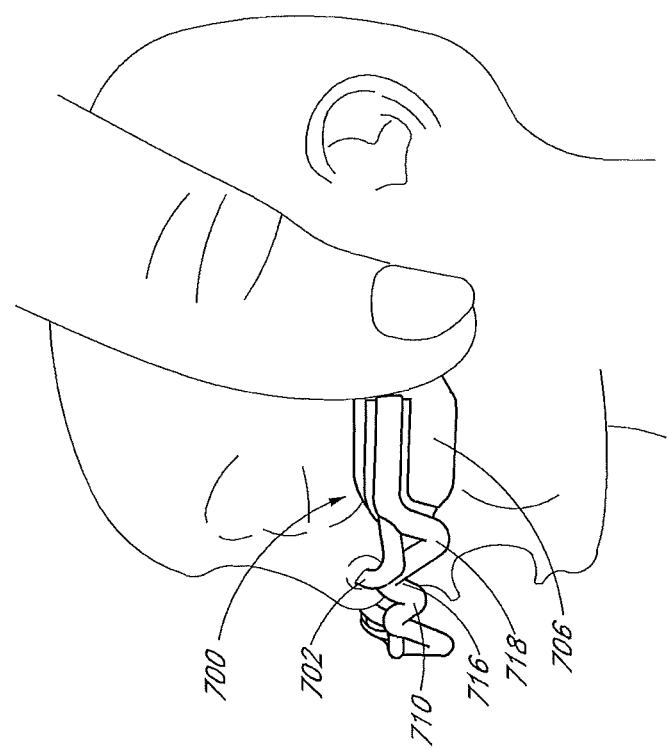
Figure 9D:
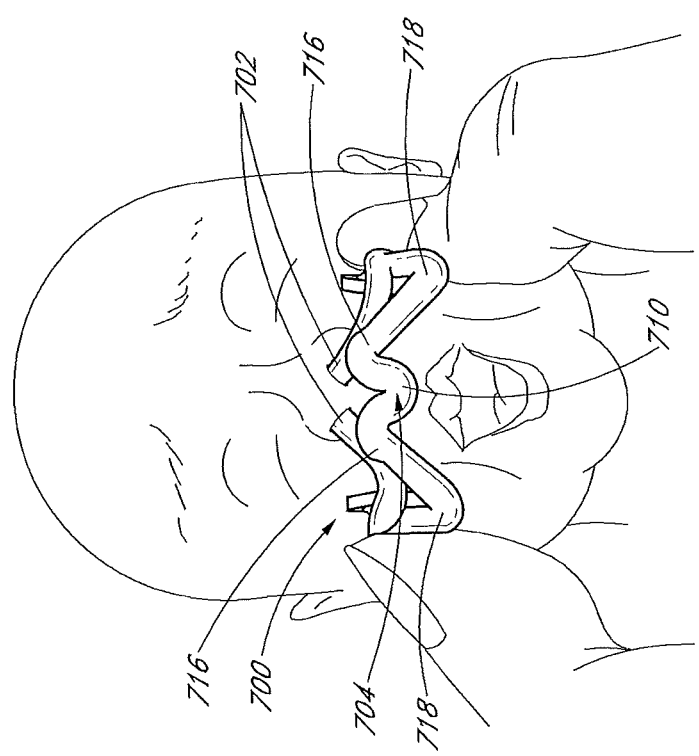

In some embodiments, the bridge 704 can be curved downward and have a hinge 710. The hinge 710 can be predisposed to bend downward such that when the dynamic interface 700 experiences forces from facial movements or external forces, the bridge 704 can bend downward, as illustrated in FIGS. 9C and 9D. FIGS. 9C and 9D illustrate squeezing of the dynamic interface 700 on a patient's face to simulate extreme facial deformations or external forces. The downward bending can help stabilize the prongs 702 and minimize movement of the prongs 702 in the sagittal plane (i.e., front/back) and coronal plane (i.e., up/down). The downward bending of the bridge 704 displaces the prongs 702 closer together, but does not displace the prongs 702 outward away from the nares, as is the case in traditional nasal interfaces. The dynamic interface 700 design may help reduce the risk of the prongs 702 flicking out of the patient's nares or rubbing against the sides of the nares.

With continued reference to FIGS. 9C and 9D, the support structure 703 can further include one or more inner hinges 716 and/or one or more outer hinges 718, such that the support structure 703 has a zig-zag shape. The inner hinges 716 can be predisposed to bend upward such that when the dynamic interface 700 experiences forces, the inner hinges 716 can bend upward, as illustrated in FIGS. 9C and 9D. The outer hinges 718 can be predisposed to bend downward such that when the dynamic interface 700 experiences forces, the outer hinges 718 can bend downward, as illustrated in FIGS. 9C and 9D. When the dynamic interface 700 experiences facial movements or external forces, the hinges 710, 716, 718 can work in conjunction to deform and at least partially absorb the forces in order to stabilize the nasal prongs 702 and help prevent the prongs 702 from flicking out of the patient's nares or rubbing against the sides of the nares.

FIGS. 10A-F illustrate another non-limiting example of a dynamic nasal interface 800 that has hinges that bend in more than one dimension. The multi-dimensional dynamic interface 800 can include one or more nasal prongs 802, a pair of wings or facial pads 806 and tubing 808 coupled to the facial pads 806, all spaced generally symmetrically about the sagittal plane. The tubing 808 can be configured to receive a suitable breathing tube that is connected to a gases supply. The breathing tube may be adhered or otherwise coupled to the interface tubing 808.

Figure 10A:
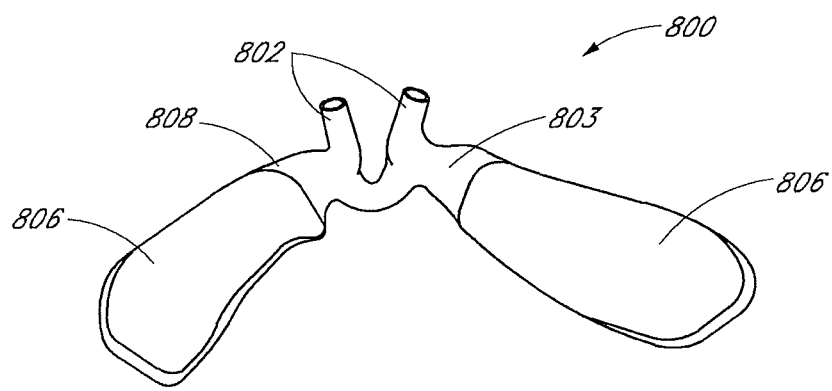
FIGS. 10A-B are various views of an embodiment of a multi-directional dynamic interface.

The facial pads 806 can be shaped to generally match the anatomical shape of the facial geometry of an intended patient. As illustrated in FIG. 10A, the facial pads 806 can be disposed toward the outer portions of the dynamic interface 800 and curved to match the shape of a patient's cheeks. In some embodiments, the facial pads can extend further toward the middle of the dynamic interface and/or can be connected as a continuous pad extending across the entire dynamic interface. The facial pads 706 can have a concave portion configured to lie over the protruding cheeks of the patient.

The anatomical shape of the facial pads 806 gives the interface a positive engagement with a patient's face at a predetermined position where the contour of the facial pads 806 matches the patient's facial contour. The pre-shaped facial pads 806 compliment the nasal prongs 802 by improving the accuracy and speed with which the prongs 802 can be placed and retained within a patient's nares.

Figure 10B:
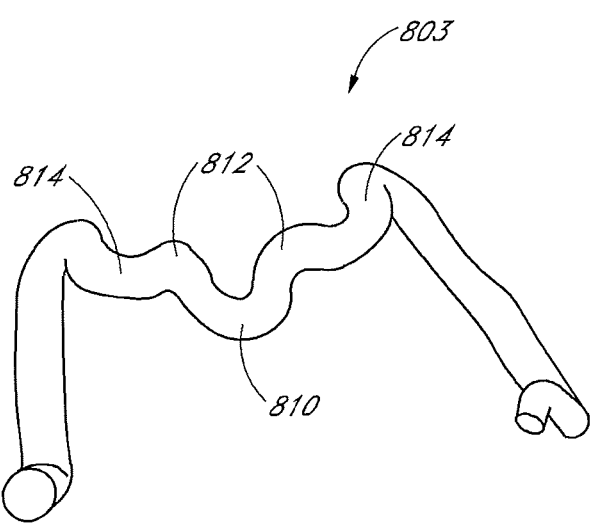
Figure 10C:
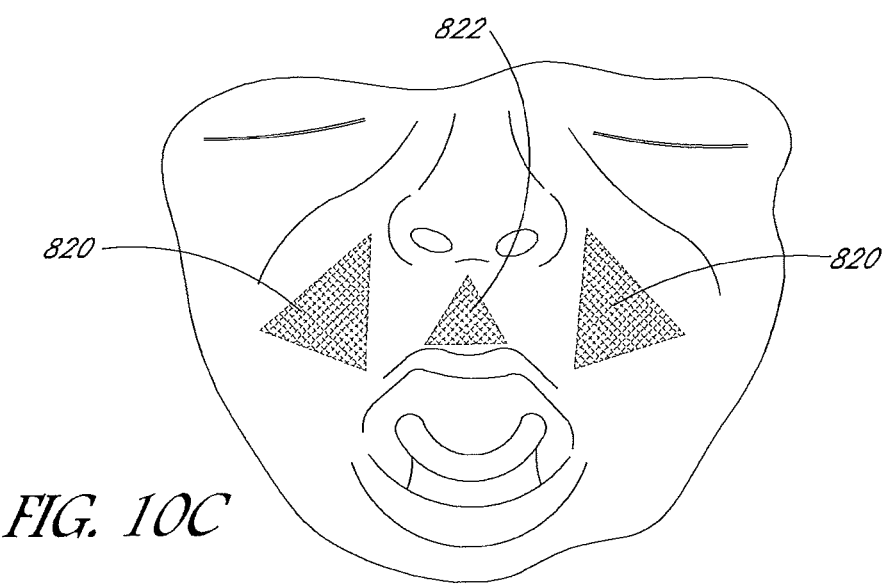
FIG. 10C illustrates the natural folds in a patient's face.

In some embodiments, the dynamic nasal interface 800 includes a structural member 803 that defines a shape and bending characteristic of the dynamic nasal interface 800, as illustrated for example in FIG. 10B. The structural member 803 can be overmoulded or otherwise attached to the dynamic nasal interface 800, such as with adhesives, sonic welding, clamps, or the like. The structural member 803 illustrated in FIG. 10B includes a bridge hinge 810 configured to be positioned between the prongs 802 and predisposed to bend downward. The illustrated structural member 803 also includes inner hinges 812 that are predisposed to bend upward, and outer hinges 814 that are predisposed to bend inward toward the patient. The bending hinges can occupy the grooves or cavities that naturally occur in the anatomy of most patients' faces, such as the crease between the cheeks and edges of the nose 820, and the space in the philtrum 822, as illustrated in FIG. 10C. In some embodiments, the multi-directional dynamic interface 800 can be pre-stressed before being attached to the patient's face, as explained below, to help the hinges bend in a predetermined direction and stabilize the nasal prongs.

Figure 10D:
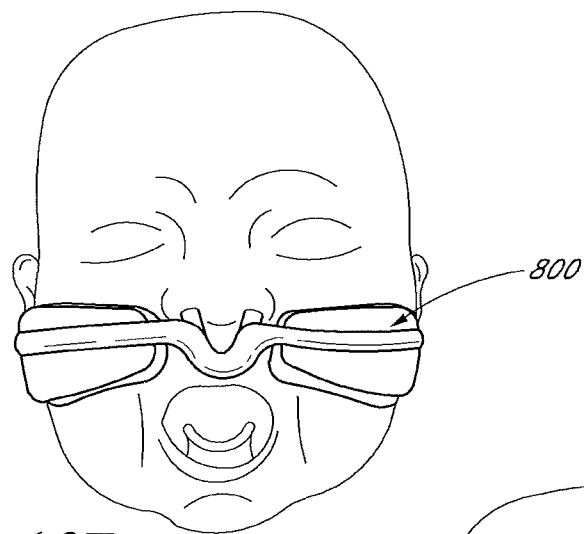
FIGS. 10D-F are various views of the multi-directional dynamic interface of FIGS. 10A-B on a patient's face.
Figure 10E:
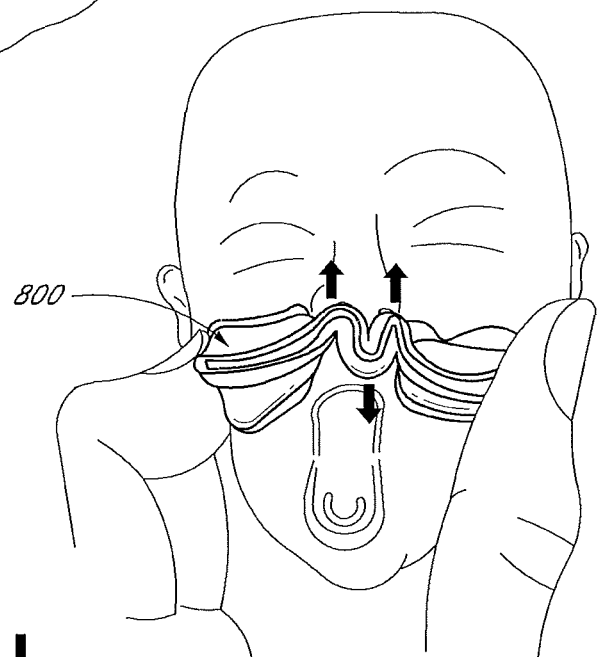
Figure 10F:
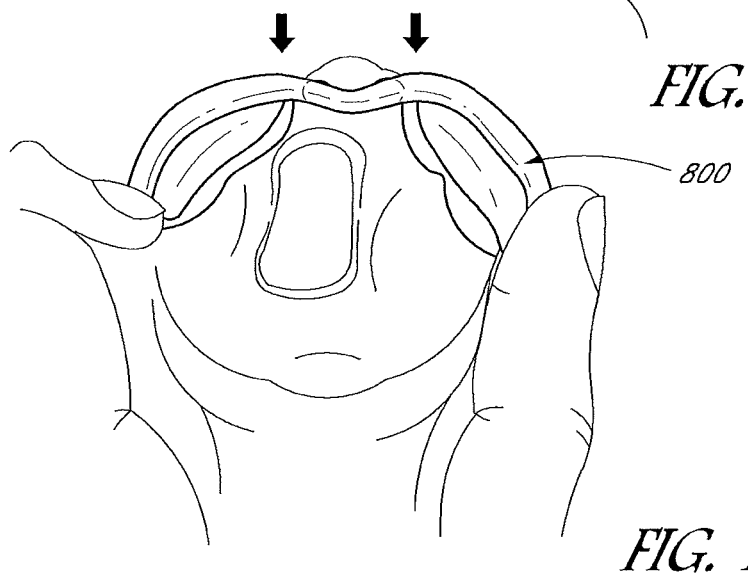

FIG. 10D illustrates a front view of a multi-directional dynamic interface 800 on a patient's face. FIG. 10E illustrates a front view of the multi-directional dynamic interface 800 as stresses are applied to the patient's face. When stresses such as squeezing forces are exerted on patient's face, the multi-directional dynamic interface 800 bends in a predefined manner. The bridge hinge 810 can bend downward and inward toward the space in the philtrum 822, as illustrated in FIG. 10E. The inner hinges 812 can bend upward. The outer hinges 814 bend inward toward the patient into the crease between the cheeks and nose 820, as illustrated in FIG. 10F. The bending of some of the hinges can be limited by the patient's anatomy. For example, the inward bending of bridge hinge 810 can be limited by the philtrum 822 of the patient, which may beneficially limit the displacement of the prongs 802. The bending of the outer hinges 814 can be limited by the creases 820, which may also beneficially limit the displacement of the prongs 802. When the multi-directional dynamic interface 800 experiences facial movements or external forces, the hinges 810, 812, 814 can work in conjunction to deform in multiple dimensions to at least partially absorb the forces in order to stabilize the nasal prongs 802 and help prevent the prongs 802 from flicking out of the patient's nares or rubbing against the sides of the nares.

Figure 11A:
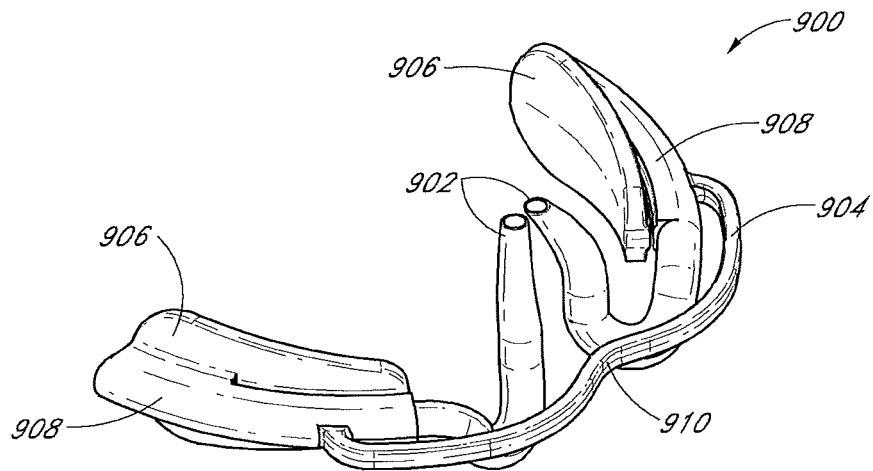
FIGS. 11A-C are various views of an embodiment of an over-strap dynamic interface.
Figure 11B:
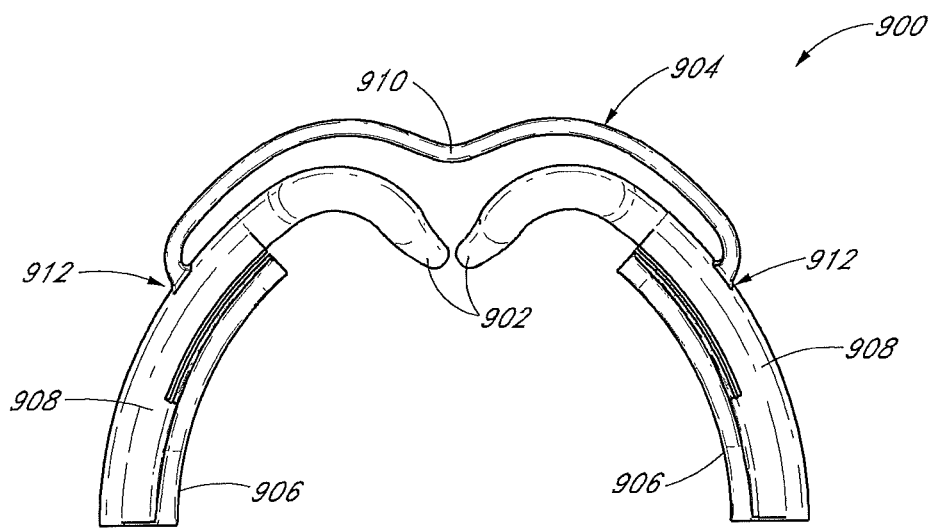
Figure 11C:
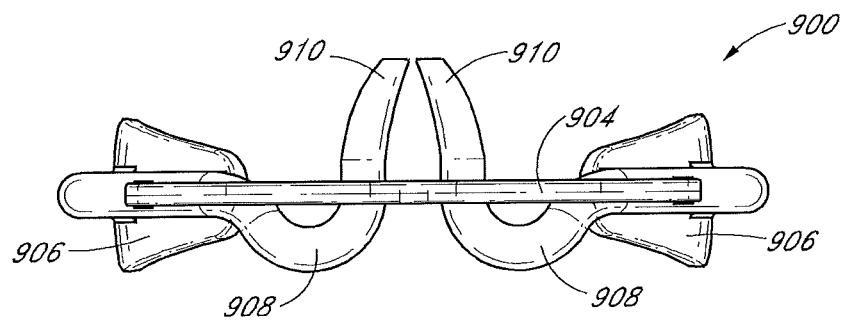

FIGS. 11A-C illustrate another non-limiting example of a dynamic nasal interface 900. The dynamic nasal interface 900 can have an overall curvature that generally corresponds to a patient's facial profile and can include two separate sides, each with a nasal prong 902, facial pad 906 and tubing 908 coupled to the facial pads 906. The tubing 908 can be in fluid communication with the prongs 902. An over-strap bridge 904 can extend between and connect the two sides of the over-strap dynamic interface 900. The open end of the tubing 908 is configured to receive a suitable breathing tube that is connected to a gases supply. The breathing tube may be adhered or otherwise coupled to the interface tubing 908.

The facial pads 906 can be shaped to generally match the anatomical shape of the facial geometry of an intended patient. As illustrated in the top view of FIG. 11B, the facial pads 906 can be disposed toward the outer portions of the dynamic interface 906 and can be curved to match the shape of a patient's cheeks. The facial pads 906 can have a concave portion configured to lie over the protruding cheeks of the patient.

The anatomical shape of the facial pads 906 gives the interface a positive engagement with a patient's face at a predetermined position where the contour of the facial pads 906 matches the patient's facial contour. The pre-shaped facial pads 906 compliment the nasal prongs 902 by improving the accuracy and speed with which the prongs 902 can be placed and retained within a patient's nares.

With continued reference to FIGS. 11A and 11B, an over-strap bridge 904 can extend between the two sides of the over-strap dynamic interface 900. The over-strap bridge 904 can be coupled to the interface tubing 908, as illustrated in the figures, or to the facial pads 906 and can be attached anywhere along each side of the dynamic interface 900. In the illustrated example, the over-strap bridge 904 is connected generally toward the middle of the interface tubing 908. In other embodiments, the over-strap bridge 904 can be connected toward the prongs 902 or toward the outer edges of the dynamic interface 900. The connection 912 between the over-strap bridge 904 and the sides of the dynamic interface 900 can be a rigid connection. In some embodiments, the connection 912 can be adjustable or flexible, such as with a hinge.

The over-strap bridge 904 can be made of a resilient material that can be stretched or adjusted to conform to a patient's facial shape and size. For example, the over-strap bridge 904 can be adjusted to enable the prongs 902 to be spaced according to an individual patient's nasal anatomy, providing a wide range of patient sizes that can be accommodated by a particular over-strap dynamic interface 900. The over-strap bridge 904 has a bridge hinge 910 that is predisposed to bend inward toward the patient such that when the dynamic interface 900 experiences forces from facial movements or external forces, the over-strap bridge 904 bends inward.

As illustrated in the FIG. 11B, the bridge hinge 910 has an inverted curvature compared to the rest of the nasal interface. The bridge hinge 910 is curved toward the rear of the dynamic interface 900 such that the bridge hinge 910 is convex shaped when viewed from the front. The inward bending can help stabilize the prongs 902 and minimize movement of the prongs 902 in the sagittal plane (i.e., front/back) and coronal plane (i.e., up/down). The inward bending of the bridge hinge 910 can displace the prongs 902 closer together, but does not displace the prongs 902 outward away from the nares, as is the case in traditional nasal interfaces. The dynamic interface 900 design may help reduce the risk of the prongs 902 flicking out of the patient's nares or rubbing against the sides of the nares.

In some embodiments, the bridge 904 with bridge hinge 910 can be configured to be preloaded during fitting such that the over-strap dynamic interface 900 can absorb forces when the patient's face moves or when external forces are exerted on the dynamic interface 900.

The dynamic interfaces described above can at least partially made of a resilient material that can return to its original shape after being deformed by the patient's facial movements or external forces. These materials are also preferably compliant so that they conform to the patients' facial geometries. The dynamic interface materials can include silicone, rubber (synthetic or natural), thermoplastic and thermosetting polymers. The composite materials can be fabricated by co-moulding or overmoulding.

Hinges

A variety of hinge types can be used in the dynamic interfaces. The hinges can bend in a predictable, limited number of directions to define the mechanical behaviour of the dynamic interface. The following paragraphs describe a number of hinge types and how they can be implemented. The described hinges are not an exhaustive list of the hinge types that can be used and the scope of the present invention should not be limited by the particular embodiments described. The hinge types include, but are not limited to: notches, cross-sectional area, variable thickness, composite, elastic hinge, barrel & pin, and ball & socket.

FIG. 12A illustrates a nasal interface 1000 with a hinge 1010 disposed at the bridge 1004 between the prongs 1002. The hinge 1010 can be solid and can include one or more notches 1012. In the embodiment illustrated in FIG. 12B, the hinge 1010 includes three notches 1012 disposed on a side 1014 of the hinge 1010 facing away from the direction of the desired bend. The notches 1012 help the hinge 1010 bend in the illustrated direction of moment M because the notches 1012 help relieve tensile stress on the side 1014 as the notches 1012 open up. The hinge 1010 is predisposed to bending in direction M.

FIG. 13A illustrates another embodiment of a nasal interface 1100 having a bridge 1104 between the prongs 1102. The bridge 1104 is hollow and allows gases to flow through such that the prongs 1102 are in fluid communication with each other through the bridge 1104. A bridge 1104 can have a notch and act as a hinge 1110. A number of non-limiting examples of notches are provided in FIGS. 13B-D. FIG. 13B illustrates a triangular notch 1116, FIG. 13C illustrates a channel notch 1118, and FIG. 13D illustrates a trapezoidal shaped notch 1120. The notch designs can be altered to permit different amounts of bending at the hinge and a designer can choose the proper type of notch design to achieve the desired amount of bending.

A hinge can be designed into a structure through variations in its cross-sectional profile. Under an applied load a structure's cross-sectional area can predispose it to deflect in a certain direction. For example, the structure can be a bridge located between the prongs of the nasal interface. A loading force F is assumed in the transverse direction as illustrated for hinge 1210 in FIG. 14A, simulating the exaggerated facial movements or external forces discussed above. The illustrated triangular cross-sectional profile promotes bending downwards towards the mouth in the example of the bridge. The downward bending reduces the effect of the load F on the prongs' position in the nares, as discussed above.

Figure 14B:
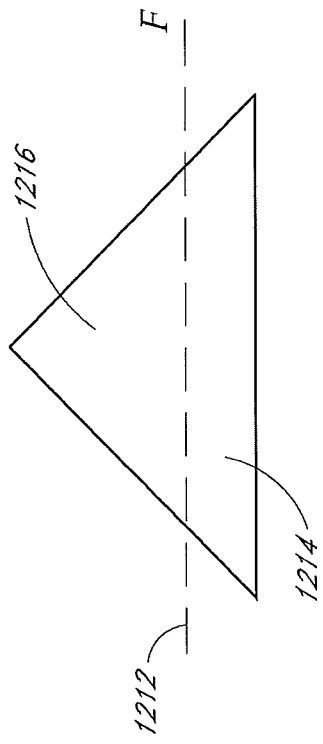
FIGS. 14A-B are various views of an embodiment of a variable cross-sectional hinge.
Figure 14A:
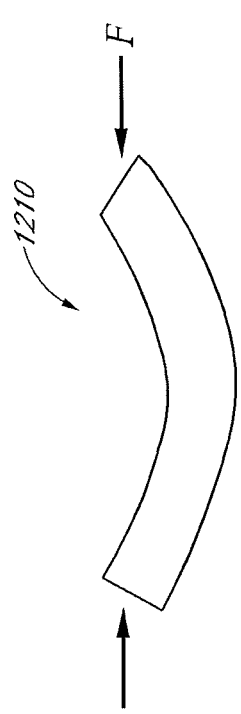

FIG. 14B illustrates a triangular cross-sectional profile of hinge 1210 having a neutral axis 1212 of bending, which is located closer to the tensile region 1214 of the structure while in its bent state. Predisposing a structure to bend in a desired direction can be achieved through making the cross-sectional area at the tensile region 1214 (i.e., the region preferred to come into tension) greater than the cross-sectional area at the compression region 1216 (i.e., the region preferred to come under compression). Because materials tend to have a compressive elastic modulus greater than a tensile elastic modulus, when a loading force F is applied to the hinge 1210, it takes less force to compress the compression regions 1216 and stretch the tensile region 1214, as opposed to stretching the compression region 1216 and compressing the tensile region 1214. Accordingly, the hinge 1210 can bend in a predictable downward direction.

Figure 15B:
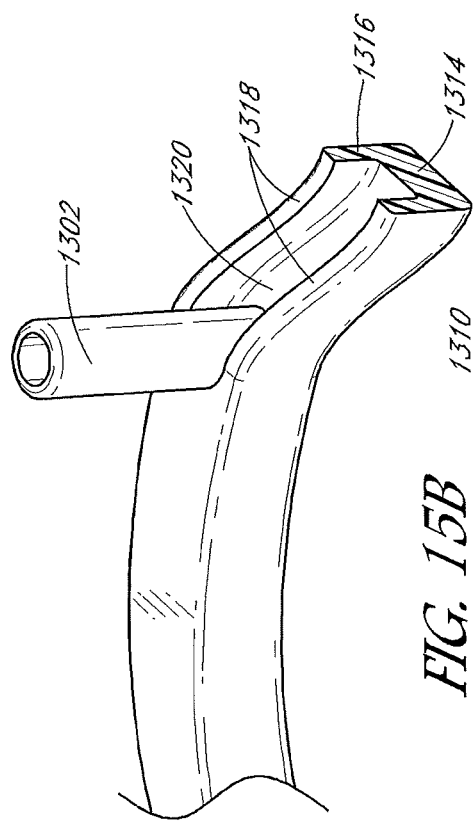
FIGS. 15A-B are various views of an embodiment of a variable cross-sectional hinge having a cutout.
Figure 15A:
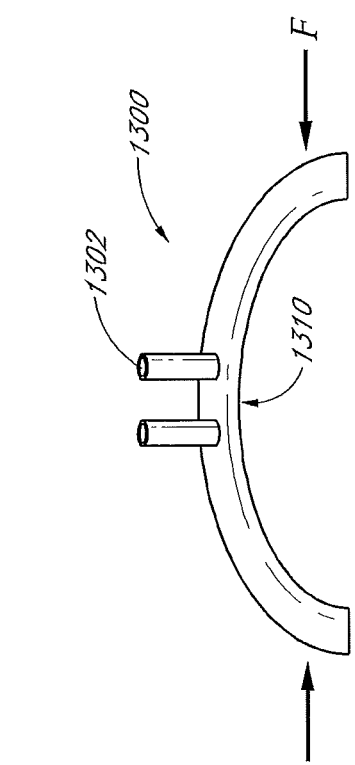

FIGS. 15A and 15B illustrate an example of a design feature, such as cutouts, which allows for reduced compressive stress. FIG. 15A illustrates loading forces F on a nasal interface 1300 in the transverse direction. The nasal interface 1300 has one or more prongs 1302 and a hinge 1310 disposed between the prongs 1302. FIG. 15B is a close-up cross-section of the hinge region. As shown in the figure, the hinge 1310 includes a tensile region 1314 and compression region 1316. As discussed above, a structure can be predisposed to bend in a desired direction by making the cross-sectional area of the tensile region 1314 greater than the cross-sectional area at the compression region 1316. In the example illustrated in FIG. 15B, the compression region 1316 is comprised of flanges 1318 and a hollow channel 1320 between the flanges 1318. The hollow channel 1320 gives the compression region 1316 a smaller cross-sectional area than the tensile region 1314 and the hinge 1310 can bend in a predictable downward direction.

FIGS. 16A and 16B illustrate an example of a hinge 1410 that has a variable thickness. Similar to as shown in FIG. 15A, loading forces F may be exerted on the nasal interface 1400 in the transverse direction. With reference to FIG. 16A, the nasal interface 1400 has one or more prongs 1402 and a hinge 1410 disposed between the prongs 1402. The hinge 1410 can be thinner in a particular direction compared to other directions such that the hinge 1410 is predisposed to bending in the direction of thinnest material. For example, in the illustrated embodiment, the hinge 1410 is thinner in the direction of prong extension, i.e., the up/down direction in the view of FIG. 16A. FIG. 16B is a close-up cross-section of the hinge region showing an elliptical cross-section. The hinge 1410 will bend in a predictable downward direction because the hinge is thinnest in the up/down direction.

FIGS. 17A and 17B illustrate a hinge 1510 that includes two materials with different properties, such as a rigid and flexible material overlaid together, that function to bend in a predetermined direction. FIG. 17A illustrates an embodiment having a flexible portion 1514 and a rigid portion 1516 in an unbent state. When forces are exerted onto the flexible portion 1514, bending is predisposed in the direction opposing the rigid portion 1516, as illustrated in FIG. 17B. The rigid portion 1516 prevents the flexible portion 1514 from bending toward the rigid portion 1516, and the flexible portion 1514 can only bend in one or more predisposed direction. The two material types can be secured using overmoulding techniques or the like to bond the materials at a central location 1518 of the hinge 150. In some embodiments, the two material types can be removably secured in one or more locations of the hinge. The outer portions of the flexible material 1514 are preferably allowed unconstrained movement.

An elastic hinge can be utilised to aid securement of an interface onto a patient's face. An elastic hinge can store elastic energy by pre-stressing the nasal interface before application to a patient. Once the nasal interface is on the patient, the stored elastic energy in the elastic hinges acts upon the patient's face to aid securement. An elastic hinge can have a relaxed state where substantially no elastic energy is stored in the hinge, and a pre-stressed state where some external forces have bent the hinge allowing it to store some elastic energy.

Figure 18A:
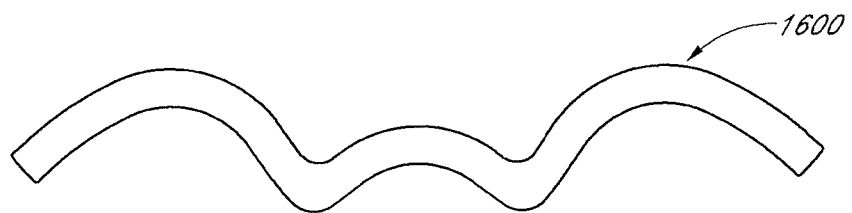
FIGS. 18A-D are various views of an embodiment of an elastic hinge.
Figure 18B:
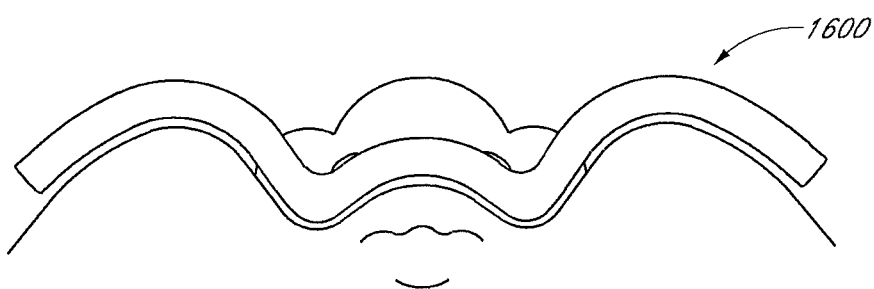

For example, a patient's face can be in a relaxed state, such as shown in FIG. 4A, or in a stressed state, such as shown in FIG. 5A. The nasal interface can be formed such that the relaxed state of the interface generally corresponds to the stressed profile of the patient's face. FIG. 18A illustrates an example of an elastic hinge nasal interface 1600 in a relaxed state. As illustrated in FIG. 18B, the nasal interface 1600 in a relaxed state can generally correspond to the stressed profile of a patient's face and in this configuration the nasal interface 1600 may exert no forces on the patient's stressed face.

Figure 18C:
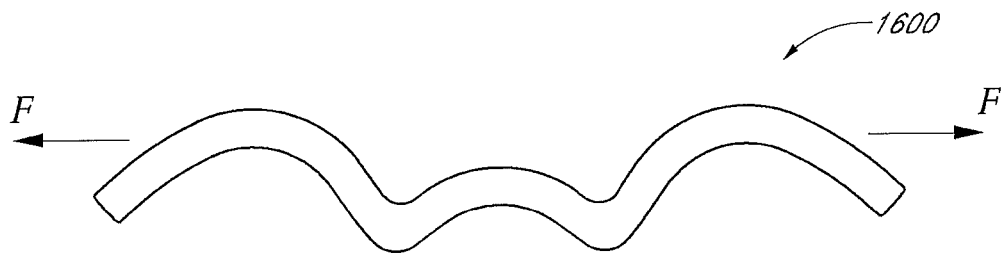
Figure 18D:
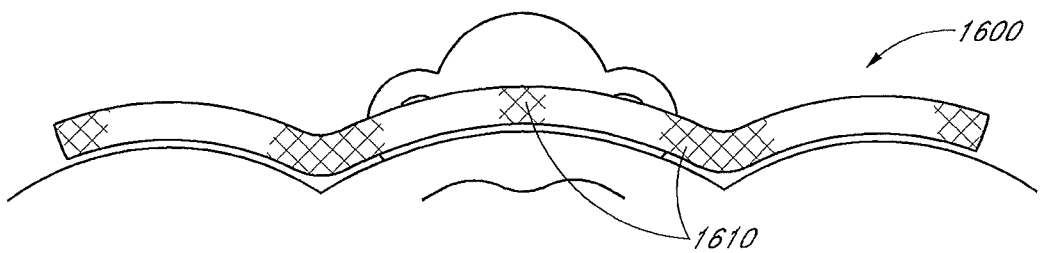

When fitting an elastic hinge nasal interface 1600 on a patient's face, a user can pre-stress the nasal interface by, for example, stretching the nasal interface as illustrated in FIG. 18C. When the pre-stressed nasal interface is placed on a patient's relaxed state face, the curves in the nasal interface serve as elastic hinges 1610, as shown by cross-hatching on FIG. 18D. When the patient's face is stressed, the elastic hinge nasal interface 1600 is predisposed to bend back to its relaxed state shown in FIG. 18B. The elastic hinge nasal interface 1600 can follow the patient's facial profile as the face goes from a relaxed profile to a stressed profile, which can stabilize the nasal prongs and help prevent the prongs from flicking out of the patient's nares or rubbing against the sides of the nares.

The nasal interface can be attached to the patient's face through a plurality of different types of retention methods, such as for example adhesives and straps. Preferably, the retention method of the nasal interface on the patient's face has a strength that can at least withstand the pre-stress energy stored in the elastic hinges.

The elastic hinge nasal interface can be made of a resilient material that can store energy when stretched from its relaxed state. Some non-limiting examples of materials include rubber, plastics, composites and steel.

Figure 19A:
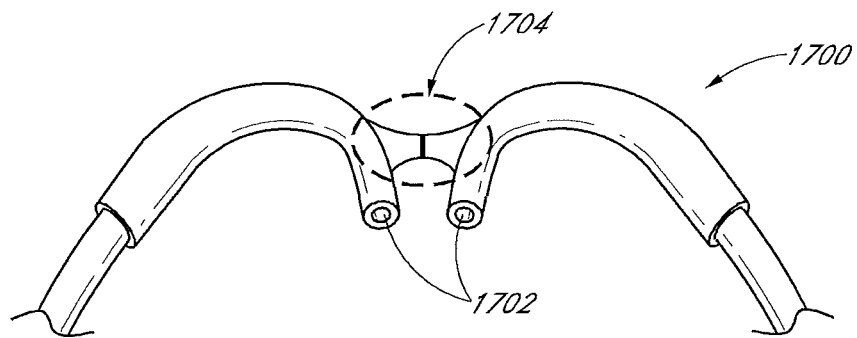
FIGS. 19A-B are various views of an embodiment of a barrel and pin hinge.

Another hinge design that can be used with the dynamic interfaces includes a pin and barrel design. FIG. 19A illustrates a dynamic interface 1700 with a pin and barrel hinge design disposed at the bridge 1704 between the nasal prongs 1702. When a patient's facial profile changes, for example due to external forces or facial movement, the angle of the pin and barrel hinge can adjust to accommodate the facial movement or external forces. The adjustment by the pin and barrel hinge helps stabilize the prongs in the patient's nares.

Figure 19B:
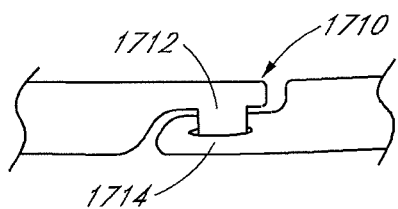

FIG. 19B illustrates an example of a pin and barrel hinge 1710. A first side of the hinge can have a pin 1712 attached or integrally formed on first side. A second side can have a barrel 1714 (e.g., through hole) attached or integrally formed on the second side. The pin 1712 can be inserted into the barrel 1714 and retained by a functional coupler. The pin 1712 can rotate relative to the barrel 1714 to form the hinge 1710.

Figure 19C:
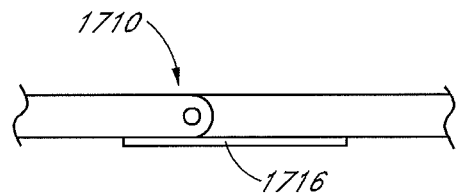
FIGS. 19C-D are various views of an embodiment of a barrel and pin hinge with directional movement.
Figure 19D:
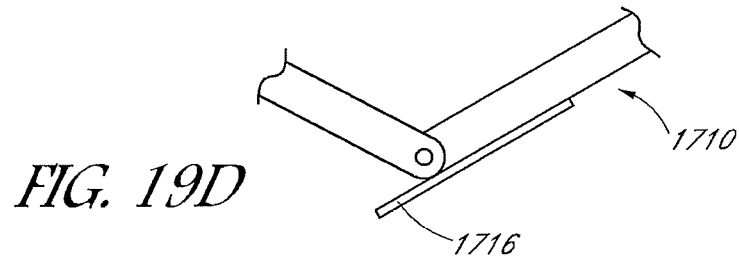

FIGS. 19C and 19D illustrate a pin and barrel hinge 1710 with directional movement. The pin and barrel hinge 1710 includes a stop 1716 that prevents the hinge from bending in a certain direction, so that the hinge 1710 is predisposed to bend in a desired direction, for example downward away from the patient's nares. The directional hinge designs can be strategically disposed in particular portions of a nasal interface to control the way the interface bends when a force is applied to the interface. Although the directional hinge design is illustrated herein in combination with a pin and barrel design, the directional hinge design can also be used with other types of hinges, such as those described herein.

Figure 20:
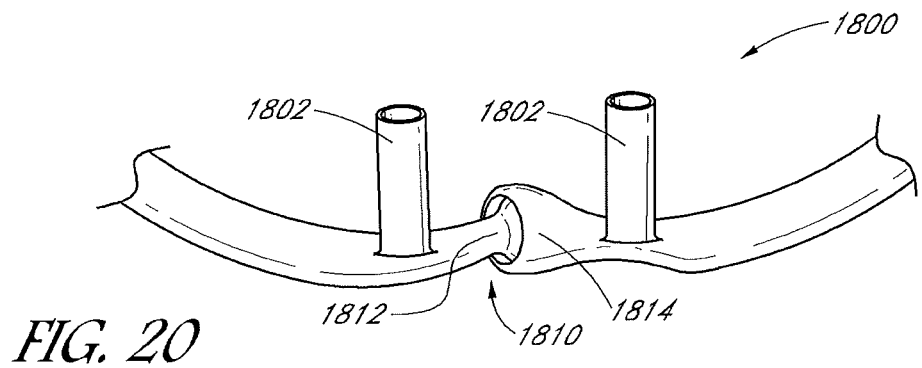

FIG. 20 illustrates an example of a nasal interface 1800 having a ball and socket hinge 1810 between the nasal prongs 1802. A first side of the hinge 1810 can have a ball 1812 attached or integrally formed on first side. A second side can have a barrel 1814 (e.g., cavity) attached or integrally formed on the second side. The ball 1812 can move and rotate inside the barrel 1814 to provide three degrees of movement about the centre of the hinge. When a patient's facial profile changes, for example due to external forces or facial movement, the three degrees of movement of the ball and socket hinge 1810 can adjust to accommodate the facial movement or external forces, and help to stabilize the prongs 1802 in the patient's nares.

Figure 21A:
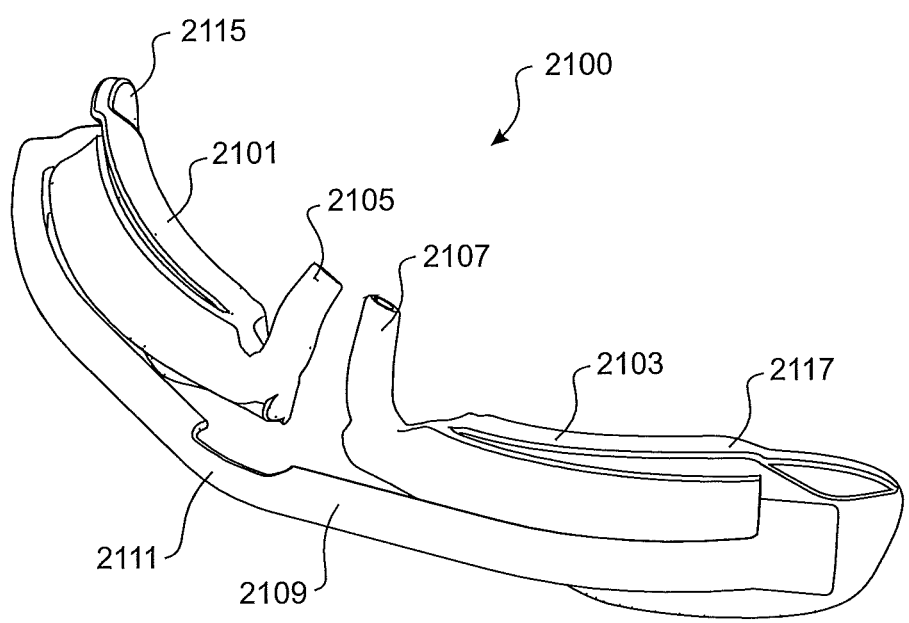
FIGS. 21A to 21C show another embodiment of a patient interface from various angles.
Figure 21B:
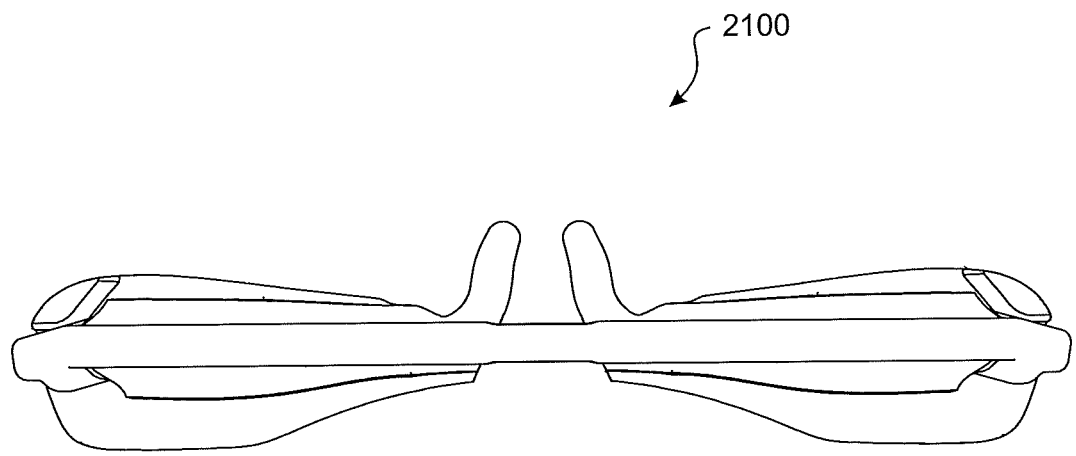
Figure 21C:
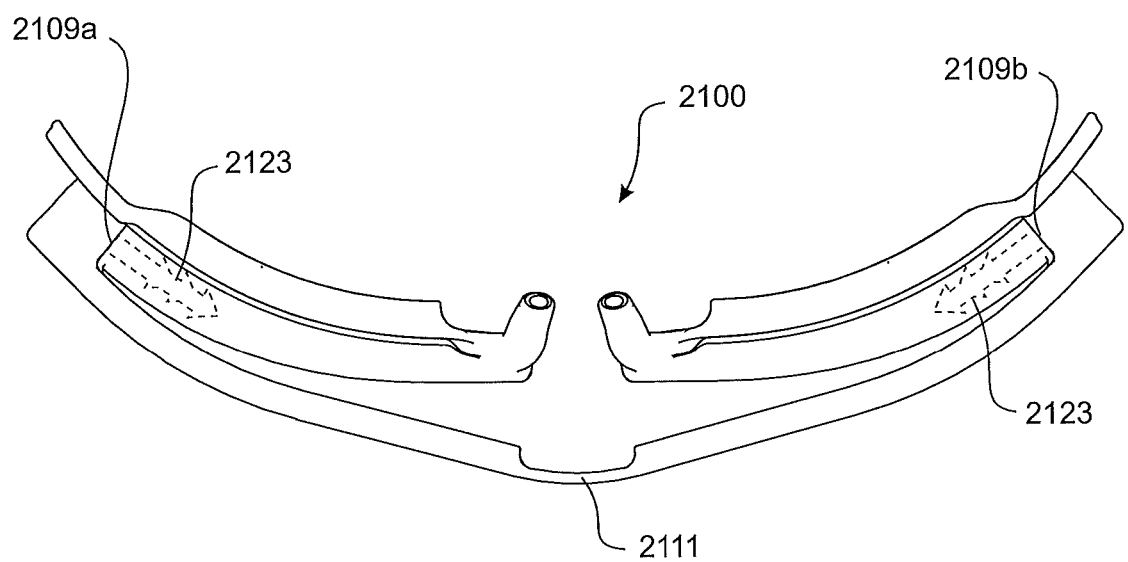

With reference to the embodiment shown in FIGS. 21A to 21C, a patient interface 2100, such as a nasal cannula, has a pair of respective left 2101 and right 2103 body portions, each body portion to be located, in-use, upon a face of a user, each of the body portions being separate from each other. At least one, and preferably both, of the body portions include a nasal prong 2105, 2107 to be inserted into, or to direct a flow of gas into, a nare or the nares of the user's nose. A bar 2109 extends from a connection point 2109a with the left body portion to a connection point 2109b with the right body portion. The bar comprises a substantially elastically deformable region 2111.

A displacement of one or both of the left and/or right body portions 2101, 2103 when in-situ is transmitted to the bar 2109 via the connection point, the substantially elastically deformable region 2111 being deformable as a reactive response to the displacement.

The substantially elastically deformable region 2111 of the bar 2109 is a substantially flexible section that is deformable to substantially absorb the displacement. The substantially elastically deformable region 2111 of the bar reduces transmission of a displacement by one of the body portions to the other of the body portions.

The connection point 2109a, 2109b of the bar 2109 to a body portion is via an anchor, in the form of a barbed projection 2121. The barbed projection 2121 is received by a region 2123 of the body portion located substantially distal to the respective prong such that the barbed projection and the prong are in fluid communication.

The elastically deformable region 2111 is substantially aligned with the or both prongs 2105, 2107 in at least one plane. Each connection point 2109a, 2109b of the bar 2109 is in fluid communication with the prong of the respective body portion and is configured to couple a gas flow path of a breathing circuit. The interface also has a facial pad 2115, 2117 associated with each body portion. Each facial pad 2115, 2117 is contoured to engage a region of the user's face.

Figure 22:
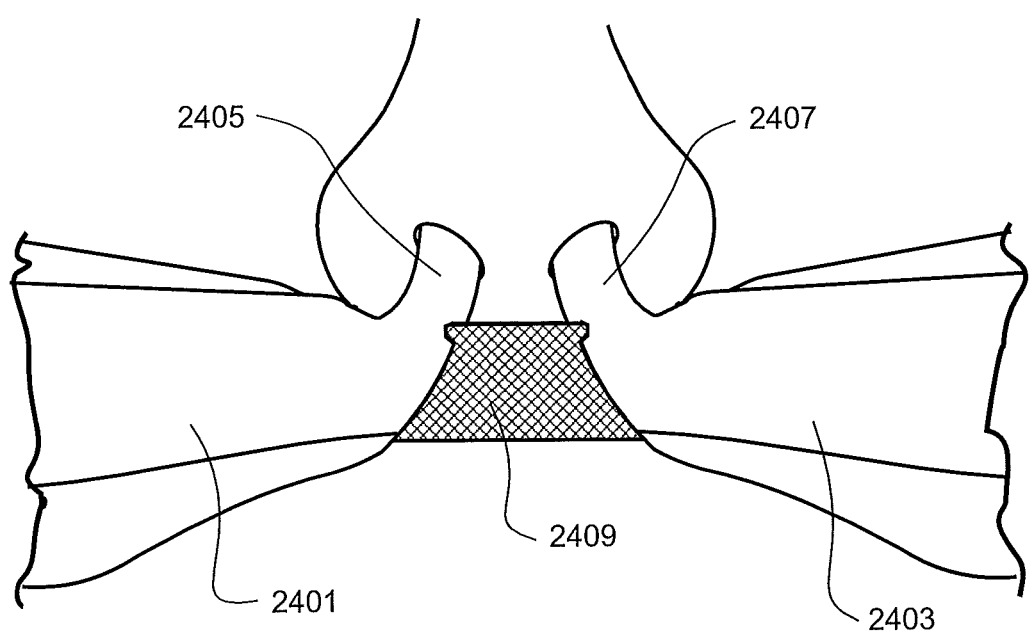
FIG. 22 shows a front view of another embodiment of a patient interface.
Figure 23A:
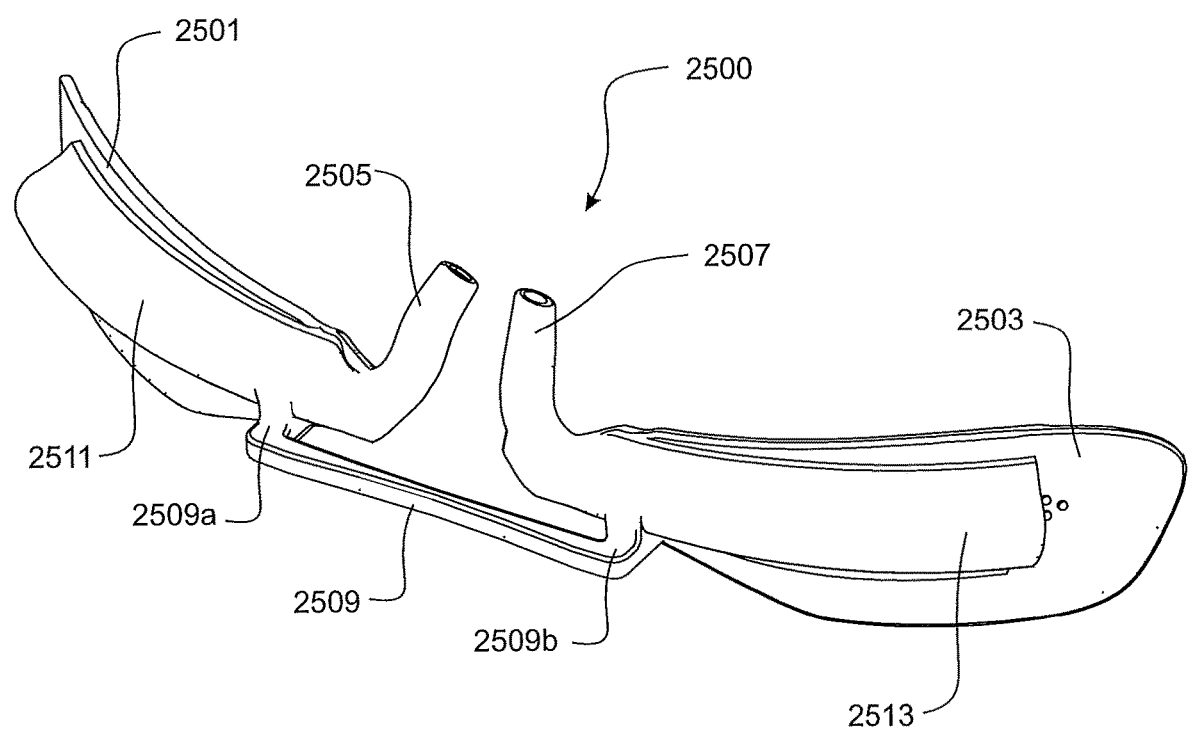
FIGS. 23A to 23C show another embodiment of a patient interface from various angles.
Figure 23B:
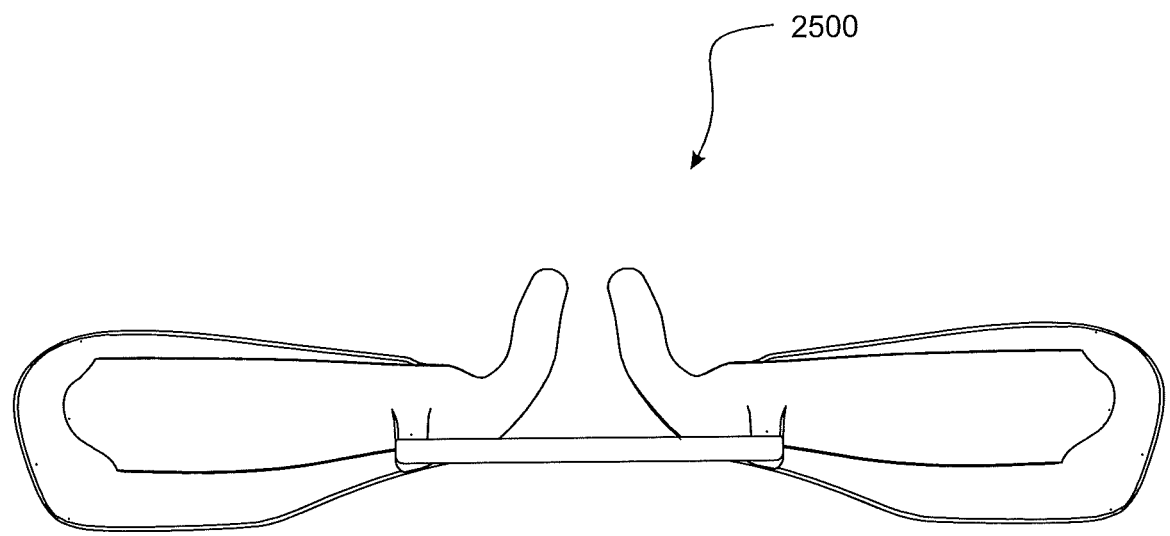
Figure 23C:
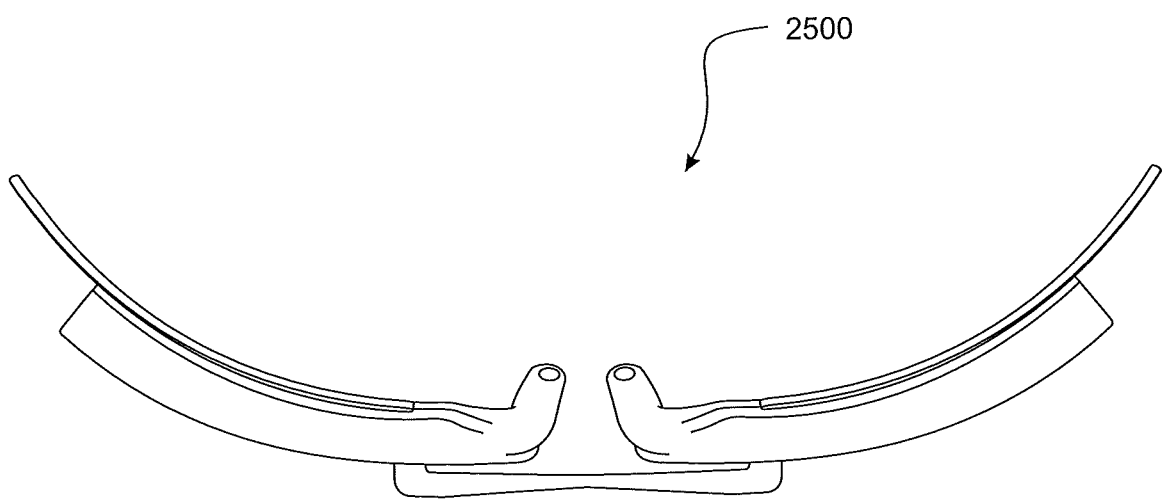

With reference to the embodiments shown in FIGS. 22 to 23C, a patient interface 2400/2500, such as a nasal cannula, has a pair of respective left 2401/2501 and right 2403/2503 body portions, to be located, in-use, upon a face of a user. A bridge 2409/2509 portion extends between each of the left and right body portions. A nasal prong 2405/2505, 2407/2507 extends from one, or each, of the inner-more ends of the respective left and/or right body portions, or extends from a region of one or both of the respective body portions substantially adjacent to the inner-more ends. The nasal prongs 2405/2505, 2407/2507 are to be inserted into, or to direct a flow of gas into, a nare or the nares of the user's nose.

The bridge portion 2409/2509 allows movement of the respective body portions 2401/2501, 2403/2503 with the inner-more ends of the body portions being brought toward each another, yet resists movement of the respective body portions with the inner-more ends being moved away from each other. A displacement of the position of one or both of the left and/or right body portions, when the patient interface is in-situ upon a user's face, is transmitted to the bridge portion 2409/2509 in a manner so as to minimise movement of the prong or prongs in relation to the user's nare(s).

With reference to the embodiment shown in FIG. 22, the bridge portion 2409 extends and connects inner-more ends of the respective body portions 2401, 2403. The bridge portion 2409 is a material that, in a direction extending between the respective inner-more ends of the body portions, is able to undergo a compression and resists or withstands a tension applied thereto. The direction extending between the respective inner-more ends of the body portions is a longitudinal direction extending along the respective body portions. The bridge portion preferably comprises a textile material, which may be a woven, knitted, or non-woven textile material.

With reference to the embodiments shown in FIGS. 23A to 23C, the bridge portion 2509 is axially expandable/stretchable, but resilient to resist movement of the respective body portions with the inner-more ends being moved away from each other. A length of the bridge portion between a connection point 2509a, 2509b on the left body portion and a connection point on the right body portion is larger than a distance between the nasal prongs 2505, 2507. The bridge portion 2509 preferably comprises a flexible polymeric material.

Figure 24A:
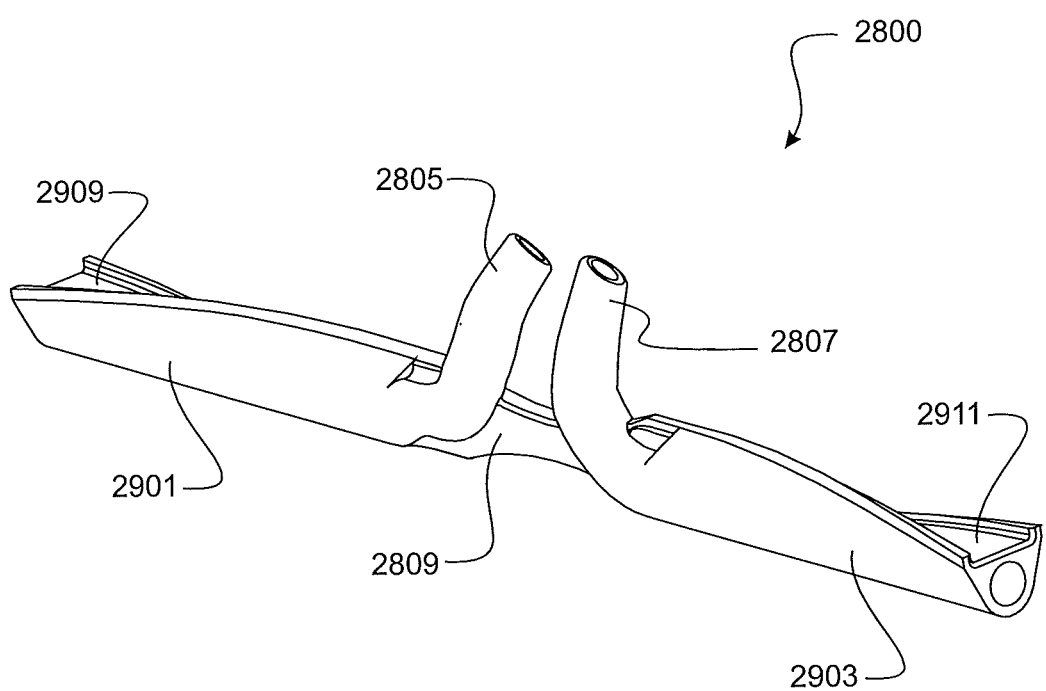
FIGS. 24A to 24C show another embodiment of a patient interface from various angles.
Figure 24B:
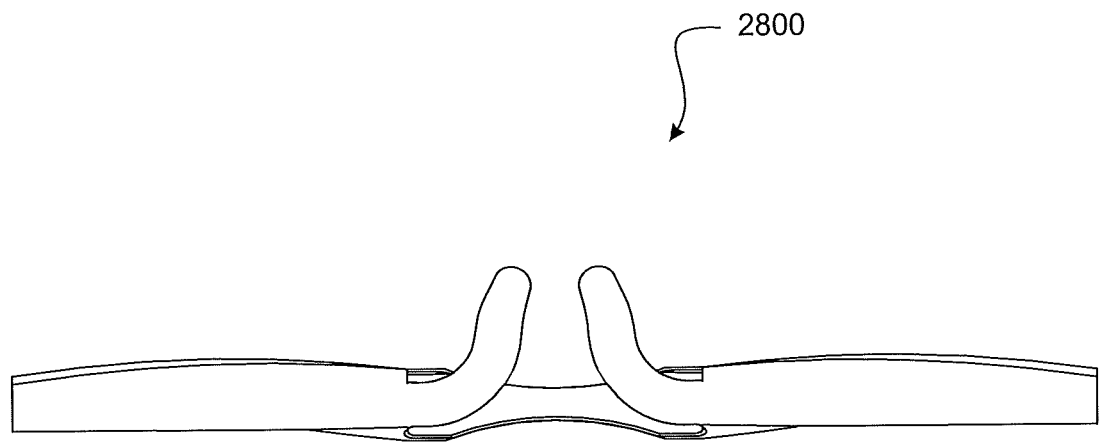
Figure 24C:
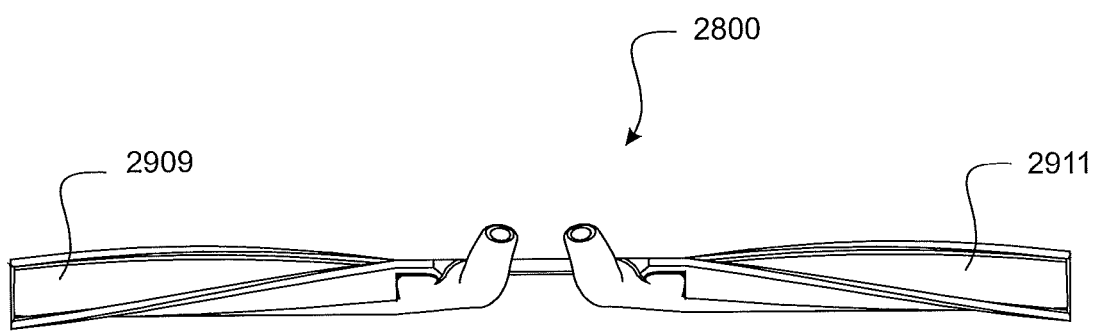

With reference to the embodiments shown in FIGS. 24A to 24C, the patient interface 2800, such as a nasal cannula, has a pair of respective left 2901 and right 2903 body portions, to be located, in-use upon a face of a user. A bridge portion 2809 extends between each of the left and right body portions. A nasal prong 2805, 2807 extends from one, or each, of the inner-more ends of the respective left and/or right body portions, or extends from a region of one or both of the respective body portions substantially adjacent to the inner-more ends. The nasal prong 2805, 2807 is inserted into, or to direct a flow of gas into, a nare or the nares of the user's nose. One, and preferably both, of the respective body portions include a user facial contacts surface 2909, 2911 oriented relative to the respective nasal prong such that, when in situ, a torsional force applied to the left and/or right body portions substantially retains the nasal prong(s) in, or in a position to direct a flow of gas into, the nare(s) of the user's nose.

Rotation of the body portion, and preferably rotation of both body portions, towards a user's face maximises a contact surface area between the facial contacting surface(s) and the face of the user and locates the nasal prong(s) into, or in the position for directing the flow of gases into, the nare(s) of the user's nose.

The bridge section 2809/2909 is of a relatively smaller diameter than the left and right body portions. Each body portion comprises a channel fluidly connected to the respective nasal prong at one end and open for fluidly coupling a gas flow path of a breathing circuit at an opposing end.

With reference to the embodiment shown in FIGS. 24A to 24C, at least one, and preferably each, of the left and right body portions includes an axially twisted facial 2909, 2911 contacting surface moveable between a relaxed position and a torsioned position in which a surface area for locating adjacent the user's face is increased.

The facial contacting surface 2909, 2911 is axially twisted along a length of the body portion from an inner end of the body portion to an outer end of the body portion. The facial contacting surface 2909, 2911 extends helically along the length of the body portion. The facial contacting surface, in the relaxed position, faces away from a direction of extension of the nasal prong(s) at the distal end, and in the torsioned position, faces in the direction of extension of the nasal prong(s) and is substantially planar along a substantial length of the body portion.

Figure 25A:
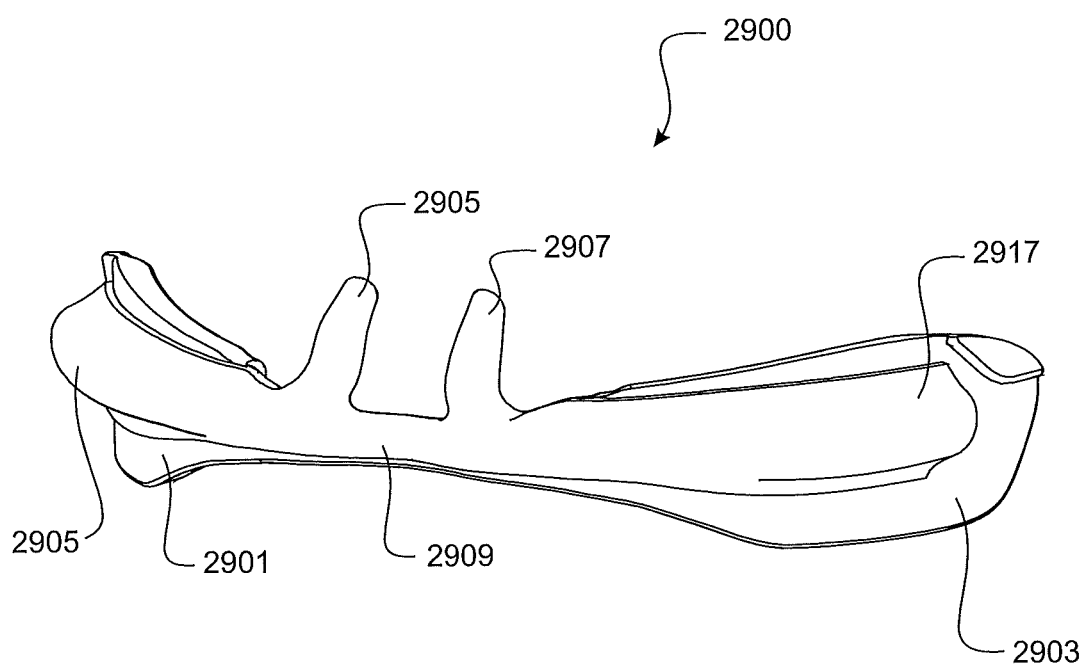
FIGS. 25A to 25C show another embodiment of a patient interface from various angles.
Figure 25B:
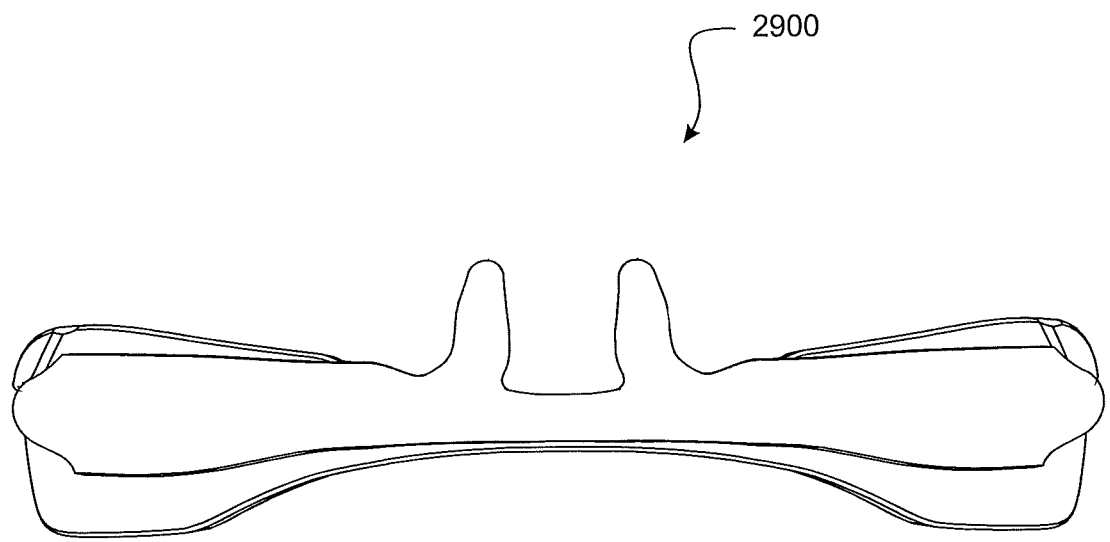
Figure 25C:
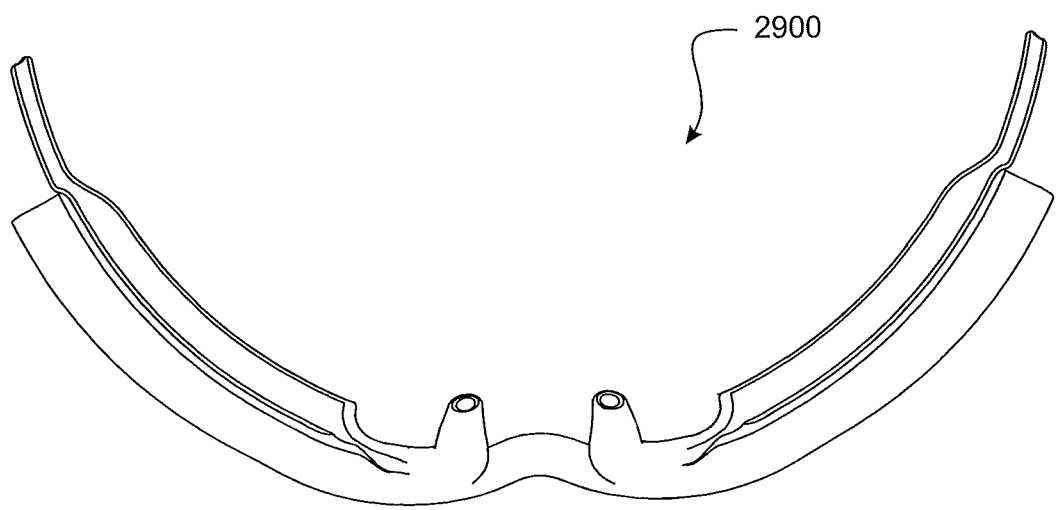

With reference to the embodiment shown in FIGS. 25A to 25C, the nasal prong(s) 2905, 2907 are angled relative to the respective left and right body portions to exert torsion on the body portion upon insertion of the nasal prong(s) into the nare(s) of the user's nose. The facial contacting surface of the respective left and/or right body portion is contoured to engage the user's facial cheek.

Figure 26:
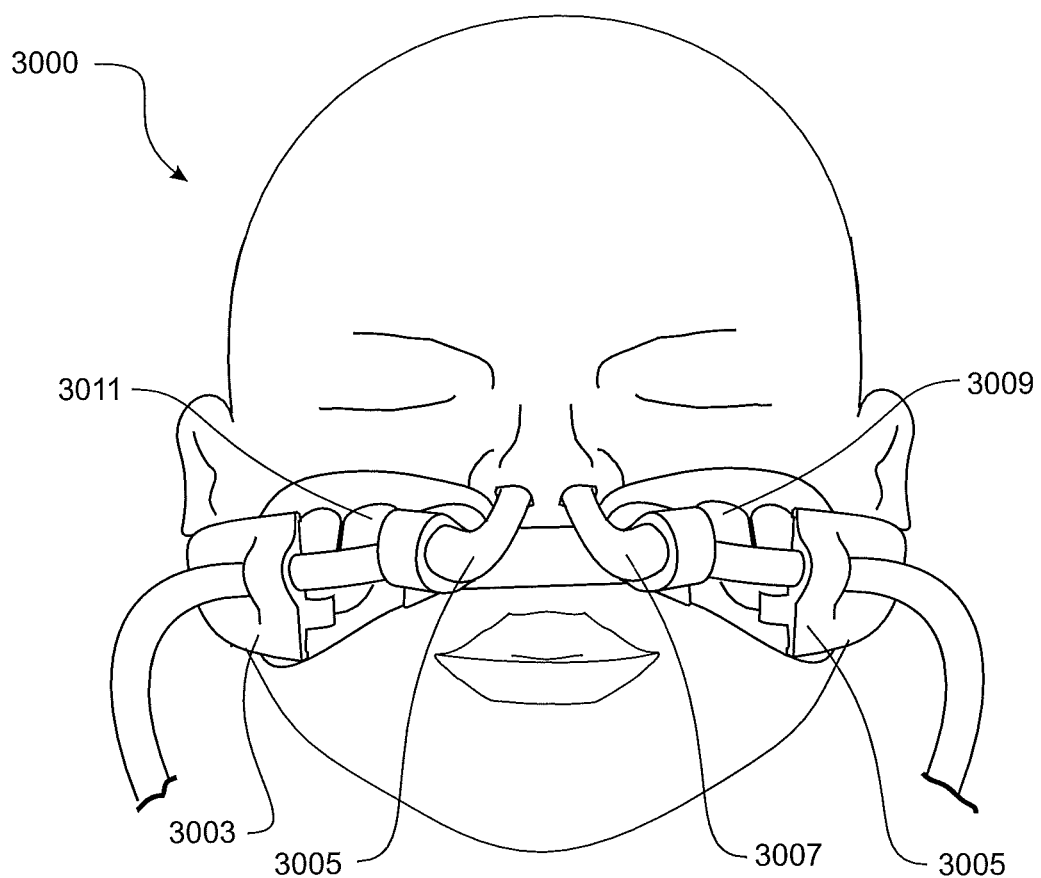
FIG. 26 shows another embodiment of a patient interface from various angles.

With reference to the embodiment shown in FIG. 26, a patient interface 3000, such as a nasal cannula, has a pair of respective left and right body portions 3001, 3003, to be located, in-use upon a face of a user. A bridge portion extends between each of the left and right body portions. A nasal prong extends from one, or each, of the inner-more ends 3005, 3007 of the respective left and/or right body portions, or extends from a region of one or both of the respective body portions substantially adjacent to the inner-more ends. The nasal prongs are inserted into, or to direct a flow of gas into, a nare or the nares of the user's nose. The interface has a series of discrete and separate facial contacting surface(s) 3009, 3011 movable relative to each other to respond to force(s) or movement(s), or both, experienced by facial contacting surface(s) and at least partially alleviate the transfer of such force(s) and/or movements) to the nasal prong(s).

Figure 27A:
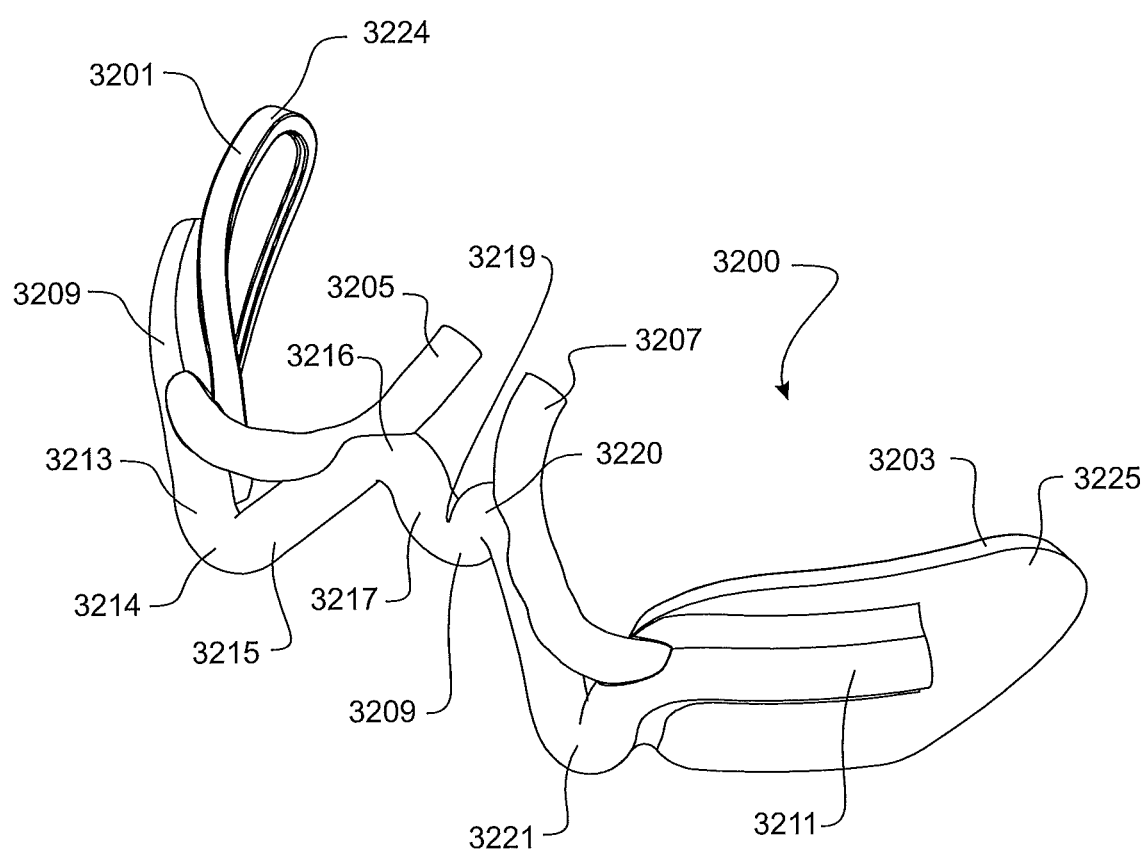
FIGS. 27A to 27C show another embodiment of a patient interface from various angles.
Figure 27B:
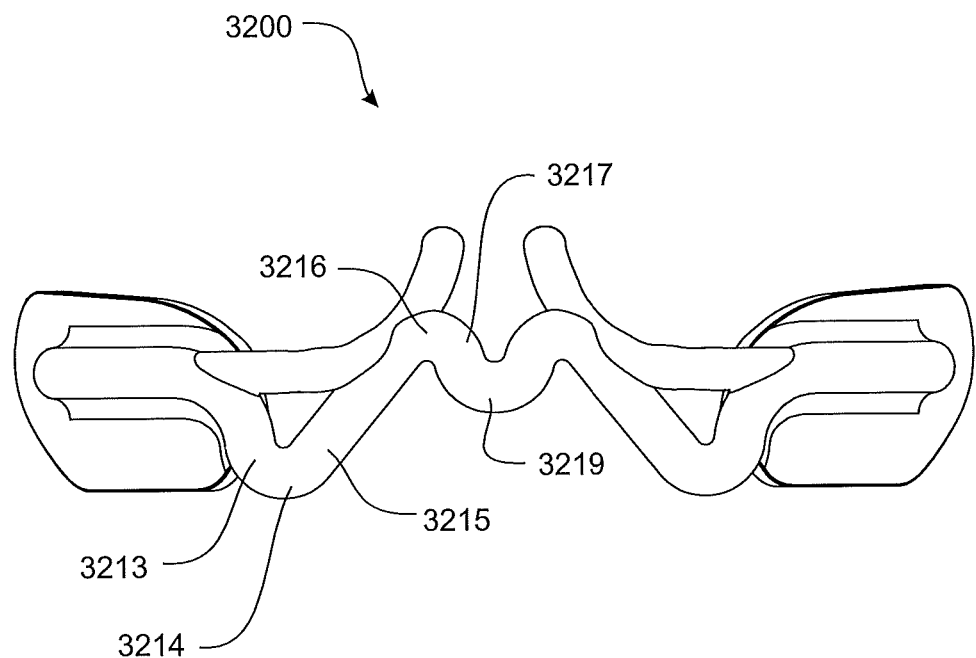
Figure 27C:
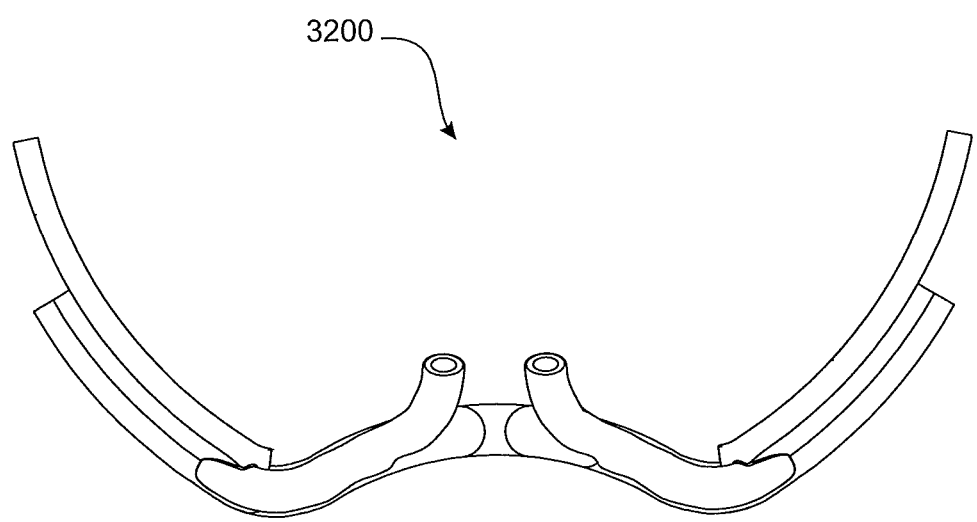

With reference to the embodiment shown in FIGS. 27A to 27C nad 28, a patient interface 3200/3300, such as a nasal cannula, has a pair of respective left 3201/3301 and right 3203/3303 body portions, each body portion to be located, in-use, upon a face of a user. The patient interface 3200/3300 also has a bridge portion 3209/3309 extending between the left and right body portions. A nasal prong 3205/3305, 3207/3307 extends from one, or each, of the inner-more ends of the respective left and/or right body portions, or extends from a region of one or both of the respective body portions substantially adjacent to the inner-more ends. The nasal prong 3205/3305, 3207/3307 is inserted into, or to directs a flow of gas into, a nare or the nares of the user's nose. The cannula includes at least one hinged region, described in detail blow. The at least one hinged region is pivotable relative to another region of the cannula about at least a pair of substantially orthogonal axes, or along a pair of substantially orthogonal planes, or both, to respond to force(s) or movement(s), or both, experienced by the other region and at least partially alleviate the transfer of such force(s) and/or movement(s) to the nasal prong(s). The at least one hinged region may be pivotable about three substantially orthogonal axes, or along three substantially orthogonal planes, or both.

The bridge 3209 also comprises a bridge hinge 3219 adjacent the nasal prong or between the pair of nasal prongs. The bridge hinge 3219 is predisposed to have an acute curvature. The bridge hinge 3219 is predisposed to bend inwardly toward the user, and downwardly away from the nare(s) in situ.

The bridge 3209 further comprises a second hinge on one side of the bridge hinge, or a pair of opposed second hinges 3216, 3220 on either side of the bridge hinge 3219 and adjacent the nasal prong or nasal prongs. The second hinge or each hinge of the pair of second hinges 3216, 3220 is predisposed to have an acute curvature. The second hinge, or each hinge of the pair of second hinges 3216, 3220 is predisposed to bend upwardly towards the nare(s) of the user and outwardly away from the user in situ.

The bridge 3209 comprises a third hinge adjacent the left or the right body portion, or a pair of third hinges 3214, 3221 disposed adjacent the respective left and right body portions. The third hinge or each of the pair of third hinges 3214, 3221 is predisposed to have an acute curvature. The third hinge or each of the pair of third hinges 3214, 3221 is predisposed to bend downward away from the nare(s) and outward away from the user in situ.

With reference to the embodiment shown in FIGS. 27A to 27C, one end of the bridge portion extends substantially orthogonally from the third hinge, or either end 3222, 3223 of the bridge portion extends substantially orthogonally from either one of the pair of third hinges and inwardly towards the facial cheek(s) of the user in situ. Each body portion has a facial pad 3224, 3225 contoured to engage a region of the user's face. Either end of the bridge portion extends along at least a portion of the facial pad.

The bridge portion 3209 is substantially hollow at least at either end of the bridge portion to transport a flow of gases there through. Either end of the bridge portion is configured to couple a gas flow path of a breathing circuit. The bridge portion 3209 comprises an annular cross section along at least a substantial portion of the length of the bridge portion.

The nasal prong(s) 3205, 3207 extend(s) from, and is/are fluidly coupled to, a respective end of the bridge portion.

Figure 28:
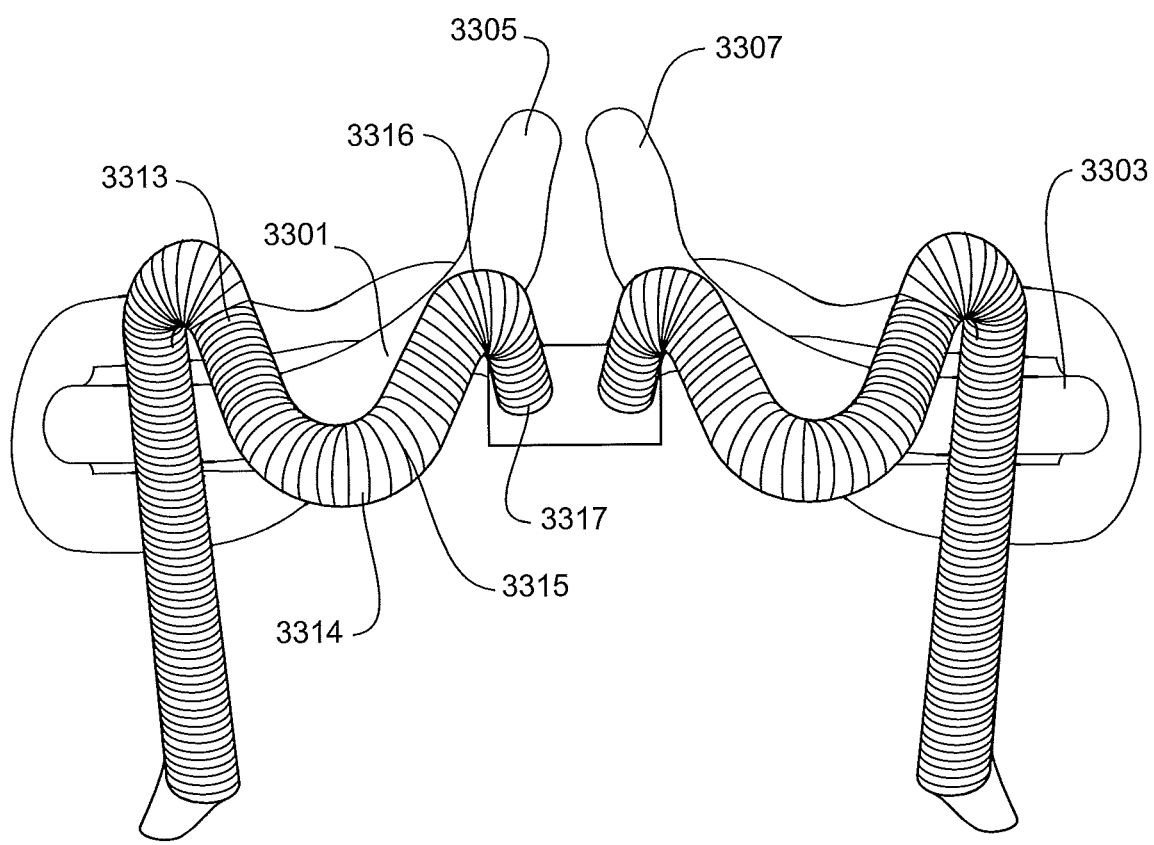
FIG. 28 shows another embodiment of a patient interface from various angles.

With reference to the embodiment shown in FIG. 28, the bridge further comprises a fourth hinge adjacent the third hinge, or a pair of fourth hinges 3326, 3327 adjacent the respective pair of third hinges. The fourth hinge or each hinge of the pair of fourth hinges is predisposed to have an acute curvature. The fourth hinge, or each hinge of the pair of fourth hinges is predisposed to bend downwardly away from the nare(s) of the user and inwardly toward the facial cheek(s) of the user in situ. Each body portion comprises a facial pad 3324, 3325 contoured to engage upon a region of the user's face.

Although certain embodiments, features, and examples have been described herein, it will be understood by those skilled in the art that many aspects of the methods and devices illustrated and described in the present disclosure may be differently combined and/or modified to form still further embodiments. For example, any one component of the nasal interfaces illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

Additional Embodiments

Item 1: A patient interface, such as a nasal cannula, comprising:

a pair of respective left and right body portions, each body portion to be located, in-use, upon a face of a user, each of the body portions being separate from each other, at least one, and preferably both, of the body portions including a nasal prong to be inserted into, or to direct a flow of gas into, a nare or the nares of the user's nose, and a bar extending from a connection point with the left body portion to a connection point with the right body portion, the bar comprising a substantially elastically deformable region, wherein a displacement of one or both of the left and/or right body portions when in-use is transmittable to the bar via the connection point, the substantially elastically deformable region being deformable as a reactive response to the displacement.

Item 2. The patient interface as defined in item 1, wherein the substantially elastically deformable region of the bar comprises a substantially flexible section.

Item 3. The patient interface as defined in item 1 or 2, wherein the substantially elastically deformable region of the bar is deformable to substantially absorb the displacement.

Item 4. The patient interface as defined in any one of items 1-3, wherein the substantially elastically deformable region of the bar reduces transmission of a displacement by one of the body portions to the other of the body portions.

Item 5. The patient interface as defined in any one of items 1-4, wherein the connection point of the bar to a body portion is via an anchor.

Item 6. The patient interface as defined in item 5, wherein the anchor is a barbed projection to be received by a region of the body portion located substantially distal to the respective prong.

Item 7. The patient interface as defined in item 6, wherein the barbed projection and the prong are in fluid communication.

Item 8. The patient interface as defined in any one of items 1-7, wherein the elastically deformable region is substantially aligned with the or both prongs in at least one plane.

Item 9. The patient interface as defined in any one items 1-8, wherein each connection point of the bar is in fluid communication with the prong of the respective body portion and is configured to couple a gas flow path of a breathing circuit.

Item 10. The patient interface as defined in any one items 1-9, further comprising a facial pad associated with each body portion, the facial pad being contoured to engage a region of the user's face.

Item 1a: A patient interface, such as a nasal cannula, comprising:
a pair of respective left and right body portions, to be located, in-use, upon a face of a user, and
a bridge portion extending between each of the left and right body portions,
a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose,
the bridge portion allowing movement of the respective body portions with the inner-more ends of the body portions being brought toward each another, yet resisting movement of the respective body portions with the inner-more ends being moved away from each other.

Item 2a. The patient interface as defined in item 1a, wherein a displacement of the position of one or both of the left and/or right body portions, when the patient interface is in-situ upon a user's face, is transmitted to the bridge in a manner so as to minimise movement of the prong or prongs in relation to the user's nare(s).

Item 3a. The patient interface as defined in item 1a or 2a, wherein the bridge portion extends and connects inner-more ends of the respective body portions.

Item 4a. The patient interface as defined in any one of items 1a-3a, wherein the bridge portion is a material that, in a direction extending between the respective inner-more ends of the body portions, is able to undergo a compression and resists or withstands a tension applied thereto.

Item 5a. The patient interface as defined in item 4a, wherein the direction extending between the respective inner-more ends of the body portions is a longitudinal direction extending along the respective body portions.

Item 6a. The patient interface as defined any one of items 1a-5a, wherein the bridge portion comprises a textile material.

Item 7a. The patient interface as defined in either item 1a or 2a, wherein the bridge portion is axially expandable/stretchable but resilient to resist movement of the respective body portions with the inner-more ends being moved away from each other.

Item 8a. The patient interface as defined in item 7a, wherein a length of the bridge portion between a connection point on the left body portion and a connection point on the right body portion is larger than a distance between the nasal prongs.

Item 9a. The patient interface as defined in item 7a or 8a, wherein the bridge portion comprises a flexible polymeric material.

Item 1b. A patient interface, such as a nasal cannula, comprising:
a pair of respective left and right body portions, to be located, in-use, upon a face of a user,
a bridge portion extending between each of the left and right body portions, and
a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose,
wherein one, and preferably both, of the respective body portions include a user facial contacting surface oriented relative to the respective nasal prong such that, when in situ, a torsional force applied to the left and/or right body portions substantially retains the nasal prong(s) in, or in a position to direct a flow of gas into, the nare(s) of the user's nose.

Item 2b. The patient interface as defined in item 1b, wherein rotation of the body portion, and preferably rotation of both body portions, towards a user's face maximises a contact surface area between the facial contacting surface(s) and the face of the user and locates the nasal prong(s) into, or in the position for directing the flow of gases into, the nare(s) of the user's nose.

Item 3b. The patient interface as defined in item 1b or 2b, wherein the bridge section is of a relatively smaller diameter than the left and right body portions.

Item 4b. The patient interface as defined in any one items 1b-3b, wherein each body portion comprises a channel fluidly connected to the respective nasal prong at one end and open for fluidly coupling a gas flow path of a breathing circuit at an opposing end.

Item 5b. The patient interface as defined in any one of items 1b-4b, wherein at least one, and preferably each, of the left and right body portions includes an axially twisted facial contacting surface moveable between a relaxed position and a torsioned position in which a surface area for locating adjacent the user's face is increased.

Item 6b. The patient interface as defined in item 5b, wherein the facial contacting surface is axially twisted along a length of the body portion from an inner end of the body portion to an outer end of the body portion.

Item 7b. The patient interface as defined in item 5b, wherein the facial contacting surface extends helically along the length of the body portion.

Item 8b. The patient interface as defined in either of item 5b or 6b, wherein the facial contacting surface, in the relaxed position, faces away from a direction of extension of the nasal prong(s) at the distal end, and in the torsioned position, faces in the direction of extension of the nasal prong(s) and is substantially planar along a substantial length of the body portion.

Item 9b. The patient interface as defined in any one of items 1b-4b, wherein nasal prong or the nasal prongs are angled relative to the respective left and right body portions to exert torsion on the body portion upon insertion of the nasal prong(s) into the nare(s) of the user's nose.

Item 10b. The patient interface as defined in item 9b, wherein the facial contacting surface of the respective left and/or right body portion is contoured to engage the user's facial cheek.

Item 1c. A patient interface, such as a nasal cannula, comprising:
a pair of respective left and right body portions, to be located, in-use, upon a face of a user, and
a bridge portion extending between each of the left and right body portions,
a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose, and
a series of discrete and separate facial contacting surface(s) movable relative to each other to respond to force(s) or movement(s), or both, experienced by facial contacting surface(s) and at least partially alleviate the transfer of such force(s) and/or movements) to the nasal prong(s).

Item 1d. A patient interface, such as a nasal cannula, comprising:
a pair of respective left and right body portions, each body portion to be located, in-use, upon a face of a user, and
a bridge portion extending between the left and right body portions, and
a nasal prong extending from one, or each, of the inner-more ends of the respective left and/or right body portions, or extending from a region of one or both of the respective body portions substantially adjacent to the inner-more ends, the nasal prong to be inserted into, or to direct a flow of gas into, a nare or the nares of the user's nose,
wherein the cannula includes at least one hinged region pivotable relative to another region of the cannula about at least a pair of substantially orthogonal axes, or along a pair of substantially orthogonal planes, or both, to respond to force(s) or movement(s), or both, experienced by the other region and at least partially alleviate the transfer of such force(s) and/or movement(s) to the nasal prong(s).

Item 2d. The interface as defined in item 1d, wherein at least one hinged region is pivotable about three substantially orthogonal axes, or along three substantially orthogonal planes, or both.

Item 3d. The interface as defined in either item 1d or 2d, wherein the bridge comprises a bridge hinge adjacent the nasal prong or between the pair of nasal prongs.

Item 4d. The interface as defined in item 3d, wherein the bridge hinge is predisposed to have an acute curvature.

Item 5d. The interface as defined in item 3d or 4d, wherein the bridge hinge is predisposed to bend inward toward the user, and downward away from the nare(s) in situ.

Item 6d. The interface as defined in any one of items 3d-5d, wherein the bridge further comprises a second hinge on one side of the bridge hinge, or a pair of opposed second hinges on either side of the bridge hinge and adjacent the nasal prong or nasal prongs.

Item 7d. The interface as defined in item 6d, wherein the second hinge or each hinge of the pair of second hinges is predisposed to have an acute curvature.

Item 8d. The interface as defined in item 6d or 7d, wherein the second hinge, or each hinge of the pair of second hinges is predisposed to bend upwardly towards the nare(s) of the user and outwardly away from the user in situ.

Item 9d. The interface as defined in any one of items 6d-8d, wherein the bridge comprises a third hinge adjacent the left or the right body portion, or a pair of third hinges disposed adjacent the respective left and right body portions.

Item 10d. The interface as defined in item 9d, wherein the third hinge or each of the pair of third hinges is predisposed to have an acute curvature.

Item 11d. The interface as defined in item 9d or 10d, wherein the third hinge or each of the pair of third hinges is predisposed to bend downward away from the nare(s) and outward away from the user in situ.

Item 12d. The interface as defined in any one of items 9d-11d, wherein one end of the bridge portion extends substantially orthogonally from the third hinge, or either end of the bridge portion extends substantially orthogonally from either one of the pair of third hinges and inwardly towards the facial cheek(s) of the user in situ.

Item 13d. The interface as defined in item 12d, wherein each body portion comprises a facial pad contoured to engage a region of the user's face.

Item 14d. The interface as defined in item 13d, wherein either end of the bridge portion extends along at least a portion of the facial pad.

Item 15d. The interface as defined in any one of items 12d-14d, wherein the bridge portion is substantially hollow at least at either end of the bridge portion to transport a flow of gases there through.

Item 16d. The interface as defined in item 15d, wherein either end of the bridge portion is configured to couple a gas flow path of a breathing circuit.

Item 17d. The interface as defined in item 15d or 16d, wherein the nasal prong, or each nasal prong, extends from, and is fluidly coupled to, a respective end of the bridge portion.

Item 18d. The interface as defined in any one of items 1d-17d, wherein the bridge portion comprises an annular cross section along at least a substantial portion of the length of the bridge portion.

Item 19d. The interface as defined in any one of items 9d-18d, wherein the bridge further comprises a fourth hinge adjacent the third hinge, or a pair of fourth hinges adjacent the respective pair of third hinges.

Item 20d. The interface as defined in item 19d, wherein the fourth hinge or each hinge of the pair of fourth hinges is predisposed to have an acute curvature.

Item 21d. The interface as defined in item 19d or 20d, wherein the fourth hinge, or each hinge of the pair of fourth hinges is predisposed to bend downwardly away from the nare(s) of the user and inwardly toward the facial cheek(s) of the user in situ.

Item 22d. The interface as defined in any one of items 19d-21d, wherein each body portion comprises a facial pad contoured to engage upon a region of the user's face.

Item 1f. A nasal interface configured to stabilize prongs on a patient's face when forces are exerted on the interface, the nasal interface comprising:
an elongate body having an overall curvature that generally corresponds to a patient's facial profile, the body configured to be coupled to a gases flow source and comprising at least one lumen extending at least partially through the body;

a pair of prongs extending from the body and in fluid communication with the at least one lumen; and one or more hinges, at least one hinge disposed between the pair of prongs that is predisposed to bend in a predefined direction.

Item 2f. The nasal interface as defined in item 1f, further comprising one or more facial pads configured to rest on a patient's face.

Item 3f. The nasal interface as defined in item if or 2f, wherein the at least one hinge disposed between the pair of prongs has a curvature that is generally inverted from the overall curvature of the elongate body.

Item 4f. The nasal interface as defined in item 3f, wherein the at least one hinge disposed between the pair of prongs is configured to bend inward towards the patient's face.

Item 5f. The nasal interface as defined in any one of items 1f-4f, wherein the nasal interface has a generally gullwing shape.

Item 6f. The nasal interface as defined in any one of items 1f-4f, wherein the nasal interface has a wavy shape.

Item 7f. The nasal interface as defined in any one of items 1f-4f, wherein the nasal interface has a curved space frame-like support structure.

Item 8f. The nasal interface as defined in any one of items 1f-7f, wherein the nasal interface bends in more than one dimension.

Item 9f. The nasal interface as defined in any one of items 1f-8f, wherein the one or more hinges comprises a notch.

Item 10f. The nasal interface as defined in any one of items 1f-9f, wherein the one or more hinges comprises a variable cross-sectional area.

Item 11f. The nasal interface as defined in any one of items 1f-10f, wherein the one or more hinges comprises a variable thickness.

Item 12f. The nasal interface as defined in any one or more of items 1f-11f, wherein the one or more hinges comprises two or more materials with different flexibilities.

Item 13f. The nasal interface as defined in any one or more of items 1f-12f, wherein the one or more hinges comprises an elastic hinge that is configured to be pre-stressed before application to a patient.

Item 14f. The nasal interface as defined in any one of items if-13f, wherein the one or more hinges comprises a barrel and pin.

Item 15f. The nasal interface as defined in any one of items 1f-13f, wherein the one or more hinges comprises a ball and socket.

Item 16f. A nasal interface comprising:

an elongate body comprising at least one lumen extending at least partially through the body, the body configured to be coupled to a gases flow source;

one or more prongs extending from the body and in fluid communication with the at least one lumen; and one or more hinges that are predisposed to bend in predefined directions;

wherein the one or more hinges are configured to stabilize a position of the one or more prongs on a patient's face when forces are exerted on the nasal interface.

Item 17f. The nasal interface as defined in item 16f, further comprising one or more facial pads configured to rest on a patient's face.

Item 18f. The nasal interface as defined in item 16f or 17f, wherein at least one of the one or more hinges is located adjacent to or between the one or more prongs.

Item 19f. The nasal interface as defined in any one of items 16f-18f, wherein at least one of the one or more hinges is configured to bend inward towards the patient's face.

Item 20f. The nasal interface as defined in any one of items 16f-18f, wherein at least one of the one or more hinges is configured to bend downward.

Item 21f. The nasal interface as defined in any one of items 16f-20f, wherein the nasal interface has a generally gullwing shape.

Item 22f. The nasal interface as defined in any one of items 16f-20f, wherein the nasal interface has a wavy shape.

Item 23f. The nasal interface as defined in any one of items 16f-20f, wherein the nasal interface has a curved space frame-like support structure.

Item 24f. The nasal interface as defined in any one of items 16f-23f, wherein the nasal interface bends in more than one dimension.

Item 25f. The nasal interface as defined in any one of claims 16f-24f, wherein the nasal interface comprises two separate sides that are coupled by an over-strap bridge.

Item 26f. The nasal interface as defined in any one of items 16f-25f, wherein the one or more hinges comprises a notch.

Item 27f. The nasal interface as defined in any one of items 16f-26f, wherein the one or more hinges comprises a variable cross-sectional area.

Item 28f. The nasal interface as defined in any one of items 16f-27f, wherein the one or more hinges comprises a variable thickness.

Item 29f. The nasal interface as defined in any one of items 16f-28f, wherein the one or more hinges comprises two or more materials with different flexibilities.

Item 30f. The nasal interface as defined in any one of items 16f-29f, wherein the one or more hinges comprises an elastic hinge that is configured to be pre-stressed before application to a patient.

Item 31f. The nasal interface as defined in any one of items 16f-30f, wherein the one or more hinges comprises a barrel and pin.

Item 32f. The nasal interface as defined in any one of items 16f-30f, wherein the one or more hinges comprises a ball and socket.

Item 33f. A nasal interface comprising:

an elongate body comprising at least one lumen extending at least partially through the body, the body configured to be coupled to a gases flow source; and one or more prongs coupled to the body and in fluid communication with the at least one lumen;

wherein the elongate body has a shape that generally corresponds to an anatomical contour of a patient's or a group of patients' facial profile.

Item 34f. The nasal interface as defined in item 33f, wherein the group of patients is one of premature babies, neonates, infant, paediatrics or adults.

Item 35f. The nasal interface as defined in item 33f or 34f, wherein the tubular body is initially malleable.

Item 36f. The nasal interface as defined in any one of items 33f-35f, wherein the shape of the tubular body is set through a hardening process.

Item 37f. The nasal interface as defined in any one of items 1f-36f, wherein at least one of the one or more hinges is predisposed to bend in a pre-defined direction.

The invention claimed is:

1. A nasal interface comprising:

an elongate body configured to extend across at least a portion of a face of a patient;

a first nasal prong and a second nasal prong extending from the elongate body and configured to be positioned in at least one nare of the patient and to direct a flow of a gas into the at least one nare of the patient;

a plurality of lumens,
wherein a first portion of the elongate body is disposed about a first end of a first lumen of the plurality of lumens,
wherein a second portion of the elongate body is disposed about a first end of a second lumen of the plurality of lumens, and
wherein the first end of the first lumen is in fluid communication with the first nasal prong and a second end of the first lumen is configured to be coupled to a gases supply source, wherein the first end of the first lumen is received by a first end of the elongate body and the first end of the second lumen is received by a second end of the elongate body, wherein the second end of the elongate body is positioned opposite from the first end of the elongate body, wherein the plurality of lumens are separate structures from the elongate body; and one or more hinging regions positioned between the first end of the elongate body and the second end of the elongate body, wherein the one or more hinging regions comprise a first bend positioned between the first nasal prong and the first end of the elongate body that is closer to the first nasal prong than the second nasal prong and a second bend positioned between the second nasal prong and the second end of the elongate body that is closer to the second nasal prong than the first nasal prong, wherein the first bend and the second bend are configured to bend when a force is applied to the nasal interface by facial movements and to stabilize a position of the first and second nasal prongs in order to abate displacement of at least one of the first and second nasal prongs out of the at least one nare of the patient.

2. The nasal interface of claim 1 further comprising at least one facial pad configured to rest on the face of the patient.

3. The nasal interface of claim 2, wherein a portion of the nasal interface is anatomically shaped to fit at least a portion of the face of the patient.

4. The nasal interface of claim 3, wherein the portion of the nasal interface comprises at least one of a size, a shape, and a curvature that matches a facial geometry of at least a portion of the face of the patient.

5. The nasal interface of claim 1, wherein the one or more hinging regions is configured to bend in a direction comprising at least one of: an inward direction, toward a philtrum of the patient; an outward direction, away from the philtrum of the patient; a downward direction, away from a nose of the patient; and an upward direction, toward the nose of the patient.

6. The nasal interface of claim 5, wherein the one or more hinging regions comprises a third bend that is located between the first nasal prong and the second nasal prong, and wherein the elongate body comprises a first elongate body and a second elongate body, wherein the first elongate body and the second elongate body are connected by a bridge comprising the third bend of the one or more hinging regions.

7. The nasal interface of claim 1, wherein the elongate body and the one or more hinging regions comprise at least one of a gullwing shape and a wavy shape.

8. A nasal interface comprising:
an elongate body comprising a first elongate body, a second elongate body, and a force absorbing bridge:
the first elongate body configured to extend across at least a portion of a face of a patient when in use, and the second elongate body configured to extend across at least a portion of the face of the patient when in use;
a first nasal prong positioned proximate the first elongate body and a second nasal prong positioned proximate an end of the second elongate body and configured to direct a flow of a gas into at least one nare of the patient when in use;
a plurality of lumens comprising a first lumen configured to be received within a first end of the first elongate body and a second lumen configured to be received with a first end of the second elongate body, wherein a first end of one of the plurality of lumens is in fluid communication with the at least one of the first and second nasal prongs and a second end of one of the plurality of lumens is configured to be coupled to a gases supply source, wherein the first end of the first elongate body is positioned opposite from the first end of the second elongate body, wherein the plurality of lumens are separate structures from the elongate body;
the force-absorbing bridge coupled to and extending between the first elongate body and the second elongate body, wherein the force-absorbing bridge is configured to absorb a force applied to the nasal interface and stabilize at least a portion of the nasal interface with respect to at least a portion of the face of the patient; and
one or more hinging regions positioned between an end of the first elongate body and an end of the second elongate body, wherein the one or more hinging regions comprises a first bend positioned between the first nasal prong and the first end of the first elongate body that is closer to the first nasal prong than the second nasal prong and a second bend positioned between the second nasal prong and the first end of the second elongate body that is closer to the second nasal prong than the first nasal prong, wherein the first bend and the second bend are configured to bend when a force is applied to the nasal interface by facial movements and to stabilize a position of the first and second nasal prongs in order to abate displacement of at least one of the first and second nasal prongs out of the at least one nare of the patient.

9. The nasal interface of claim 8, wherein the force-absorbing bridge comprises one or more bridge hinging regions configured to bend.

10. The nasal interface of claim 9, wherein at least one of the one or more hinging regions or the one or more bridge hinging regions is configured to bend inward, toward the face of the patient.

11. The nasal interface of claim 9, wherein at least one of the one or more hinging regions or the one or more bridge hinging regions is configured to bend outward, away from the face of the patient.

12. The nasal interface of claim 9, wherein at least one of the one or more hinging regions or the one or more hinging regions is configured to bend downward, away from a nose of the patient.

13. The nasal interface of claim 9, wherein at least one of the one or more hinging region or the one or more hinging regions is configured to bend upward, toward a nose of the patient.

14. The nasal interface of claim 8, wherein the first elongate body, the second elongate body, and the force-absorbing bridge comprise at least one of a gullwing shape and a wavy shape.

15. The nasal interface of claim 8, wherein the force-absorbing bridge is configured to bend in more than one dimension to stabilize at least a portion of the nasal interface with respect to at least a portion of the face of the patient.

16. The nasal interface of claim 8, wherein the force-absorbing bridge comprises a first material and a second material, wherein the second material is less flexible than the first material.

17. The nasal interface of claim 8, further comprising at least one elastic region configured to be pre-stressed before application of the nasal interface to the face of the patient.

18. The nasal interface of claim 8, further comprising at least one elastic support having a stressed configuration and a relaxed configuration, wherein the at least one elastic support is configured to be pre-stressed before application of the nasal interface to the face of the patient.

19. The nasal interface of claim 18, wherein the stressed configuration corresponds to a feature of the face of the patient absent a deforming force and wherein the relaxed configuration corresponds to a feature of the face of the patient when subject to a deforming force.

20. The nasal interface of claim 8, wherein the force-absorbing bridge is curved toward a rear of the nasal interface and forms a convex shape that bends towards the patient.

21. The nasal interface of claim 20, wherein the one or more hinging regions are positioned on either side of the force-absorbing bridge such that the nasal interface is configured to bend in at least three different locations.

* * * * *

UNITED STATES PATENT AND TRADEMARK OFFICE
CERTIFICATE OF CORRECTION

Page 1 of 1

PATENT NO. : 11,110,242 B2
APPLICATION NO. : 15/028924
DATED : September 7, 2021
INVENTOR(S) : Michael Paul Ronayne It is certified that error appears in the above-identified patent and that said Letters Patent is hereby corrected as shown below:

On the Title Page

In Column 2, item (74), Attorney, Agent, or Firm, Lines 1-2, delete "Knobbe, Martens, Olsen & Bear" and insert --Knobbe, Martens, Olson & Bear LLP--.

In the Specification

In Column 11, Line 8, delete "FIG." and insert --FIGS.--.

In Column 32, Line 21, delete "in-use" and insert --in-use,--.

In Column 33, Line 18, delete "movements)" and insert --movement(s)--.

In Column 33, Line 21, delete "nad" and insert --and--.

In Column 37, Line 30, delete "movements)" and insert --movement(s)--.

In Column 39, Line 12, delete "if" and insert --1f--.

In Column 39, Line 46, delete "if-13f," and insert --1f-13f,--.

In Column 40, Line 19, delete "claims" and insert --items--.

In Column 40, Line 62, delete "pre-defined" and insert --predefined--.

In the Claims

In Column 42, Line 3, Claim 8, delete "force absorbing" and insert --force-absorbing--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*